(12) United States Patent
Geijtenbeek et al.

(10) Patent No.: US 8,309,097 B2
(45) Date of Patent: Nov. 13, 2012

(54) C-TYPE LECTIN BINDING MOLECULES, IDENTIFICATION AND USES THEREOF

(75) Inventors: Teunis Bernard Herman Geijtenbeek, Amstelveen (NL); Yvette van Kooyk, Amsterdam (NL)

(73) Assignee: Vereniging voor Christelijk Wetenschappelijk Onderwijs, Amsterdam (NL)

( * ) Notice: Subject to any disclaimer, the term of this patent is extended or adjusted under 35 U.S.C. 154(b) by 410 days.

(21) Appl. No.: 10/533,981

(22) PCT Filed: Nov. 7, 2003

(86) PCT No.: PCT/NL03/00781
§ 371 (c)(1),
(2), (4) Date: Oct. 5, 2005

(87) PCT Pub. No.: WO2004/041292
PCT Pub. Date: May 21, 2004

(65) Prior Publication Data
US 2006/0104975 A1    May 18, 2006

(30) Foreign Application Priority Data
Nov. 7, 2002    (EP) .................................... 02079665

(51) Int. Cl.
*A61K 39/385*    (2006.01)
(52) U.S. Cl. .................................................. 424/193.1
(58) Field of Classification Search ........................ None
See application file for complete search history.

(56) References Cited

U.S. PATENT DOCUMENTS 6,949,629 B2 *   9/2005   Newman et al. ............... 530/412
7,285,642 B2 *  10/2007   Figdor et al. ................ 530/387.1

FOREIGN PATENT DOCUMENTS

| WO | WO 9727872 A1 | * | 8/1997 |
| WO | WO 9839027 A2 | * | 9/1998 |
| WO | WO 98/43677 | * | 10/1998 |
| WO | WO 00/63251 | * | 10/2000 |
| WO | WO 0154716 A2 | * | 8/2001 |

OTHER PUBLICATIONS

Ragupathi et al., Jan. 2002, vol. 20: 1030-1038.*
Wang et al., 2006, Carbohydrate Research, vol. 341: 705-716.*
Marcaurelle et al., 2002, Cur. Opin. Chem. Biol. vol. 6: 289-296.*
Sabbatini et al., 2000, Int. J. Canc. vol. 87: 79-85.*
Hovius et al., 2008, PLOS pathogens, vol. 4: 1-14.*
Coombs et al., 2005, J.Biol. Chem. vol. 24: 22993-22999.*
Piccotti et al., 1996, J. Immunol. vol. 157: 1951-1957.*
Nonaka et al., 2008, J. Immunol. vol. 180: 3347-3356.*
Boros et al., 1973, J. Immunol. vol. 110: 1118-1125.*
Appelmelk et al., 1996, Inf. and Immun. vol. 64: 2031-2040.*
van Gisbergen et al., 2005, Canc. Res. vol. 65: 5935-5944.*
Samsen et al., 2010, Eur. J. Cell. Biol. vol. 89: 87-94.*
Feinberg, et al., "Structural Basis for Selective Recognition of Oligosaccharides by DC-SIGN and DC-SIGNR", Science 2001, 294:2163-2166.
Claudius, et al., "Kinetic and equilibrium characterization of interactions between glycopeptide antibiotics and sodium carboxymethyl starch", International Journal of Pharmaceutics 1996, 144:71-79.
Schofield, et al., "Synthetic GPI as a candidate antitoxic vaccine in a model of malaria", Nature 2002, 418:785-789.
Yamamoto, et al., "Interaction of Immobilized Recombinant Mouse C-type Macrophage Lectin with Glycopeptides and Oligosaccharides", Biochemistry 1994, 33:8159-8166.
Muto, et al., "Biological activities of human mannose-binding lectin bound to two different ligand sugar structures, Lewis A and Lewis B antigens and high-mannose type oligosaccharides", Biochimica et Biophysica Acta 2001, 1527:39-46.

* cited by examiner

*Primary Examiner* — Amy Juedes
(74) *Attorney, Agent, or Firm* — TraskBritt

(57) ABSTRACT

C-type lectins are involved in the binding of many different types of carbohydrates. Considering their diversity in kind and expression of different types of cells, the influence of such binding is very diverse and dependent among others on the type of cell, the environment of the cell and the type of carbohydrate bound. In the present invention new carbohydrate specificities of C-type lectins are disclosed. Interference with this binding property has uses in the prevention of pathogen binding and also in influencing signaling pathways in the C-type lectin containing cell, particularly in Toll like receptor expressing cells such as dendritic cells. Also provided is the use of the carbohydrate specificity to enhance antigen presentation by antigen presenting cells and to manipulate migration of C-type lectin containing cells and the interaction of C-type lectin expressing cells with cellular ligands on neighboring cells.

4 Claims, 77 Drawing Sheets

Fig. 1
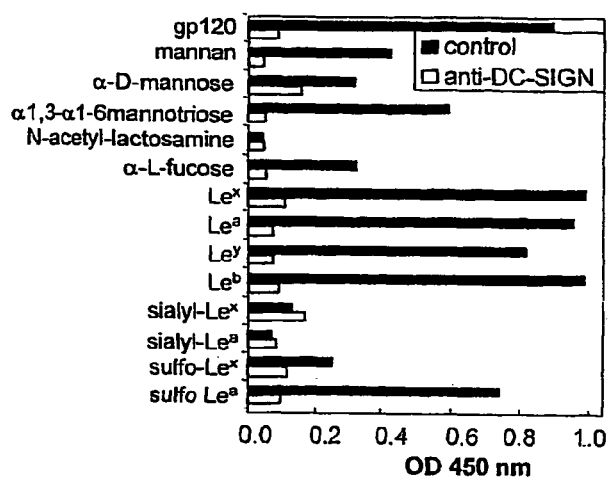
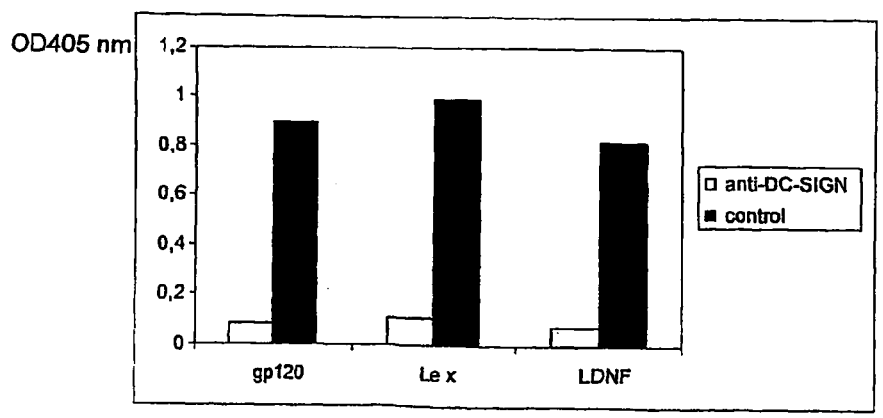
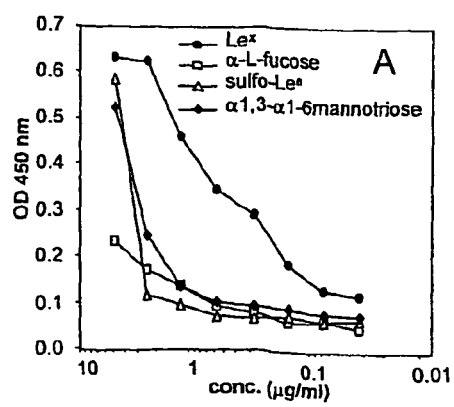

Fig. 9
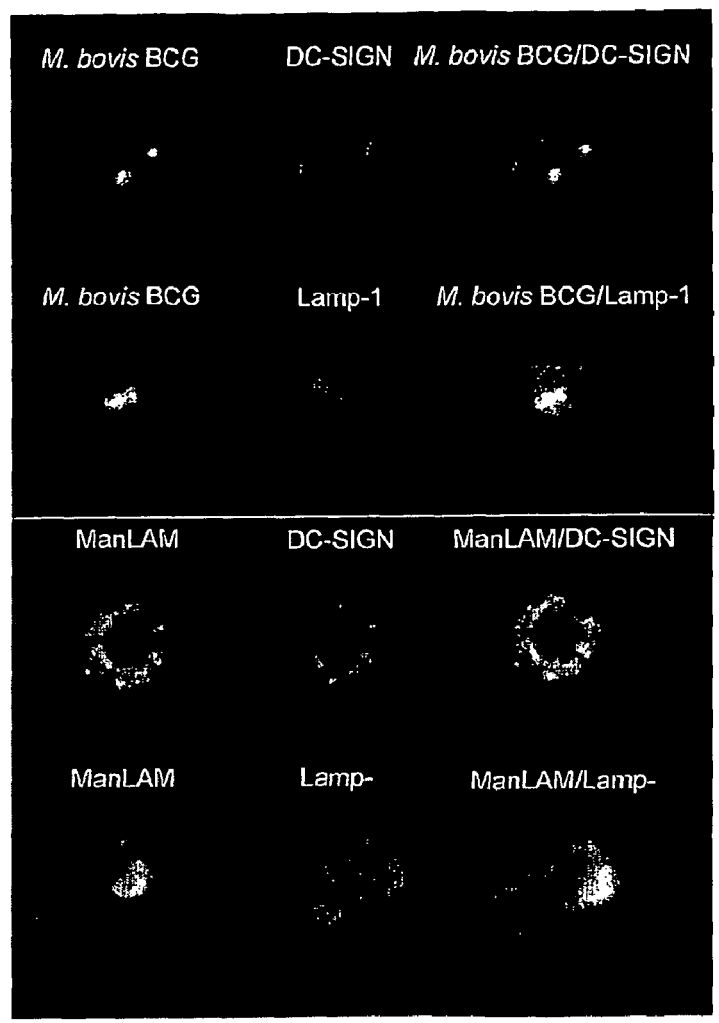
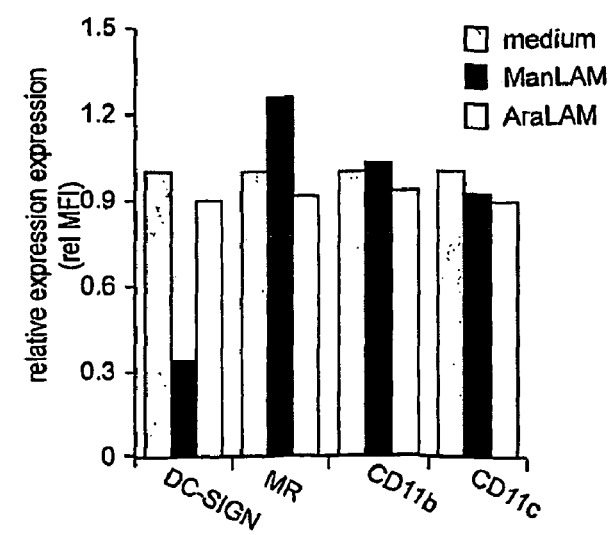

Fig. 10
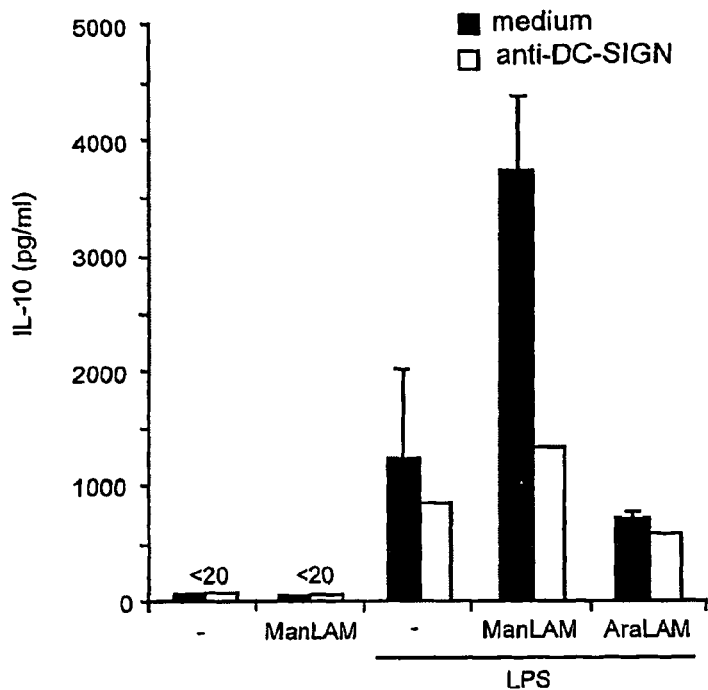
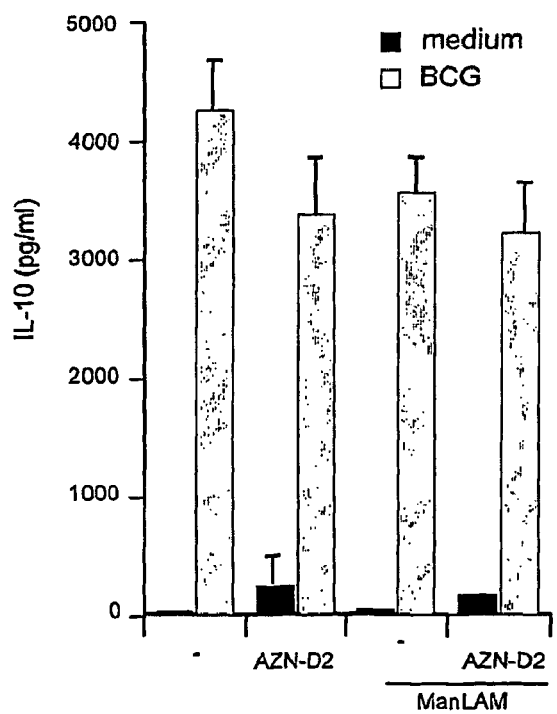

Fig. 18
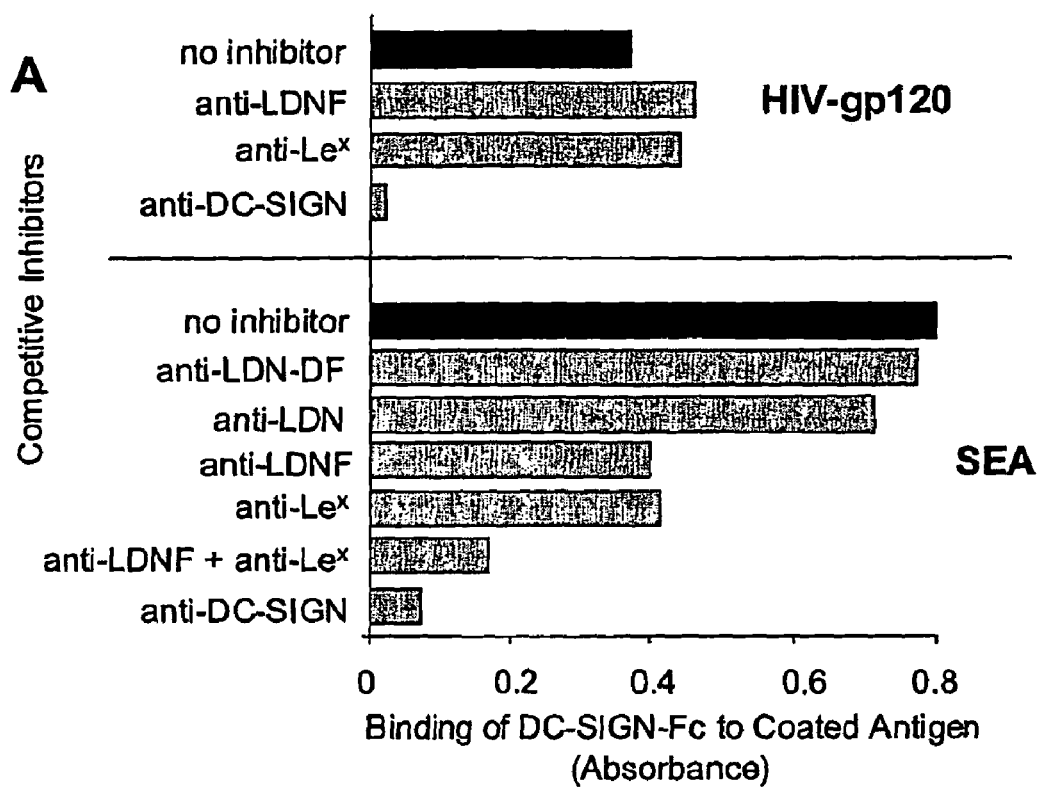
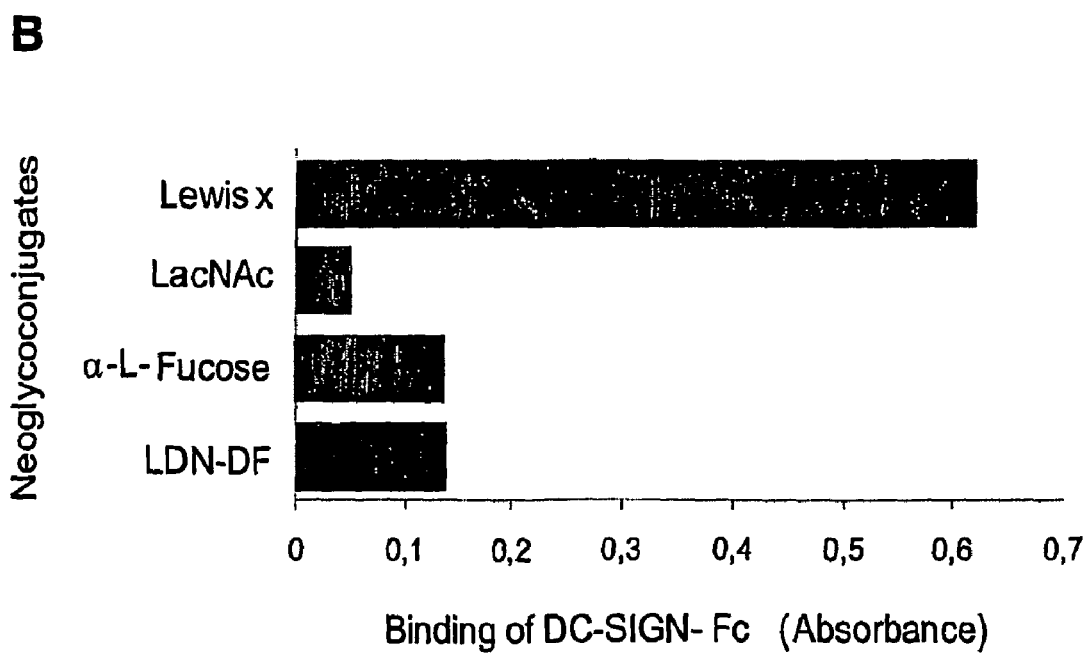

Fig. 21
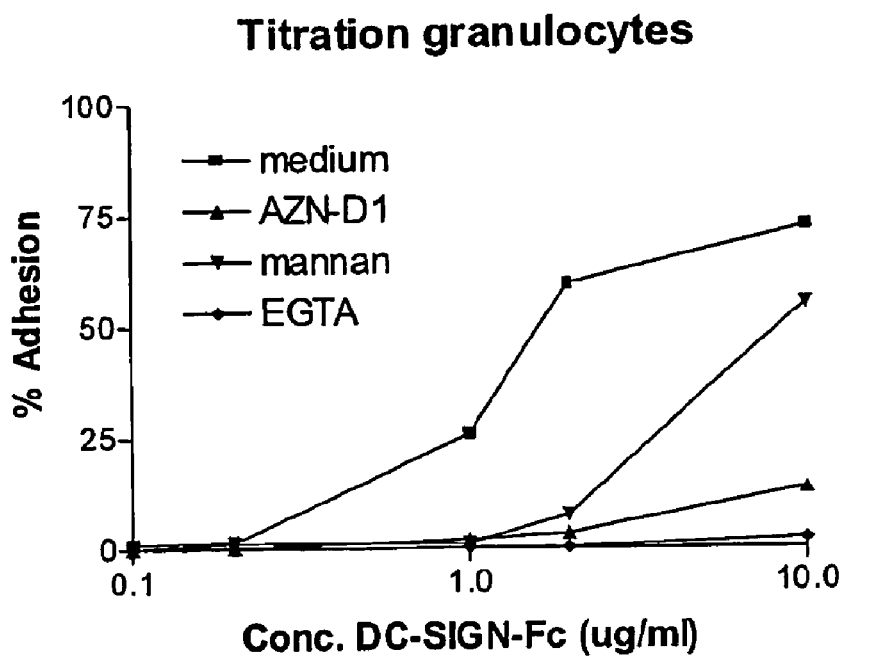
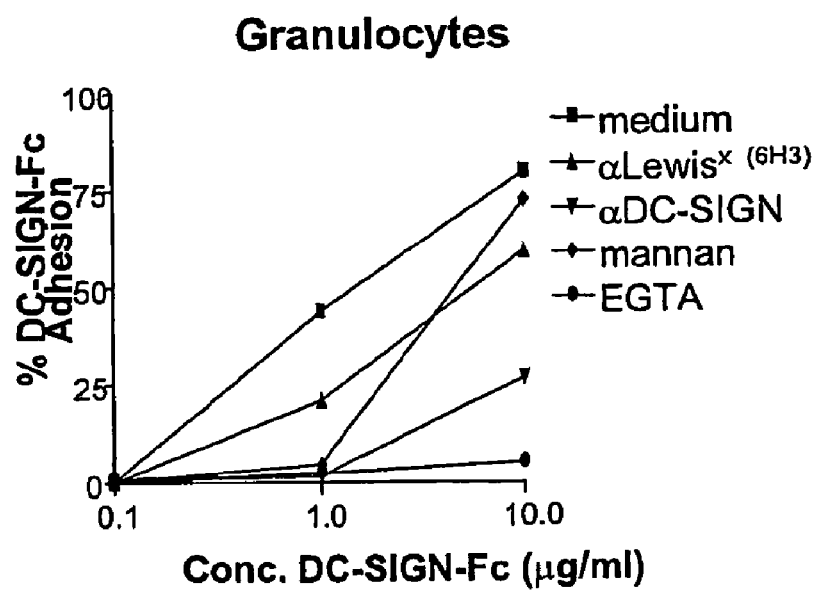

1. control
2. ICAM-2
3. ICAM-3
4. DC-SIGN ligand
5. LFA-1

→ DC-SIGN binds ICAM-2? and 75 kD ligand on NK cells

Fig. 31
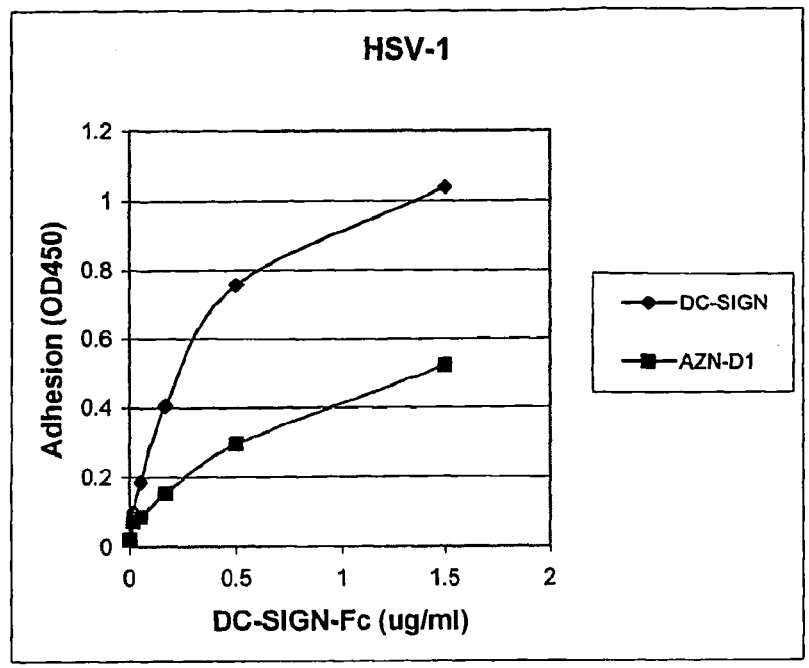
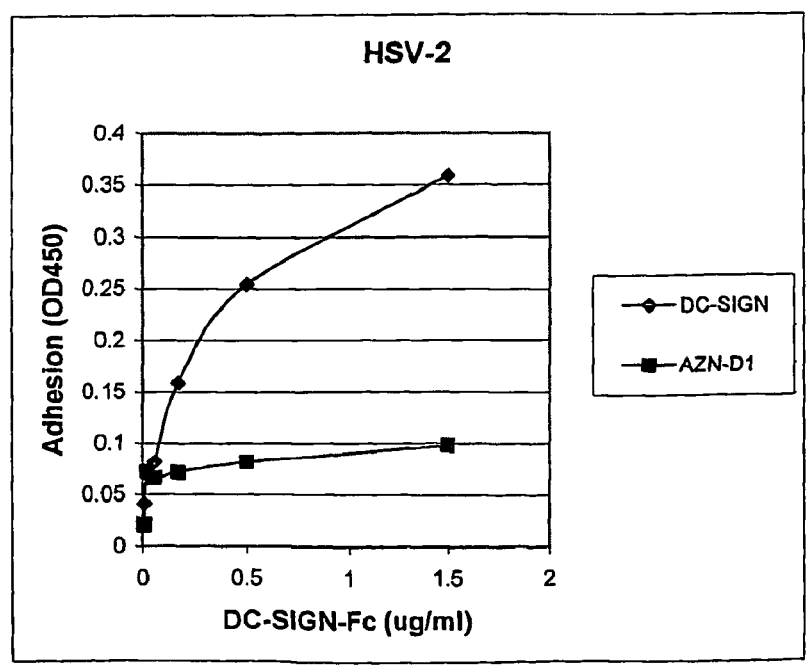

Fig. 32
A
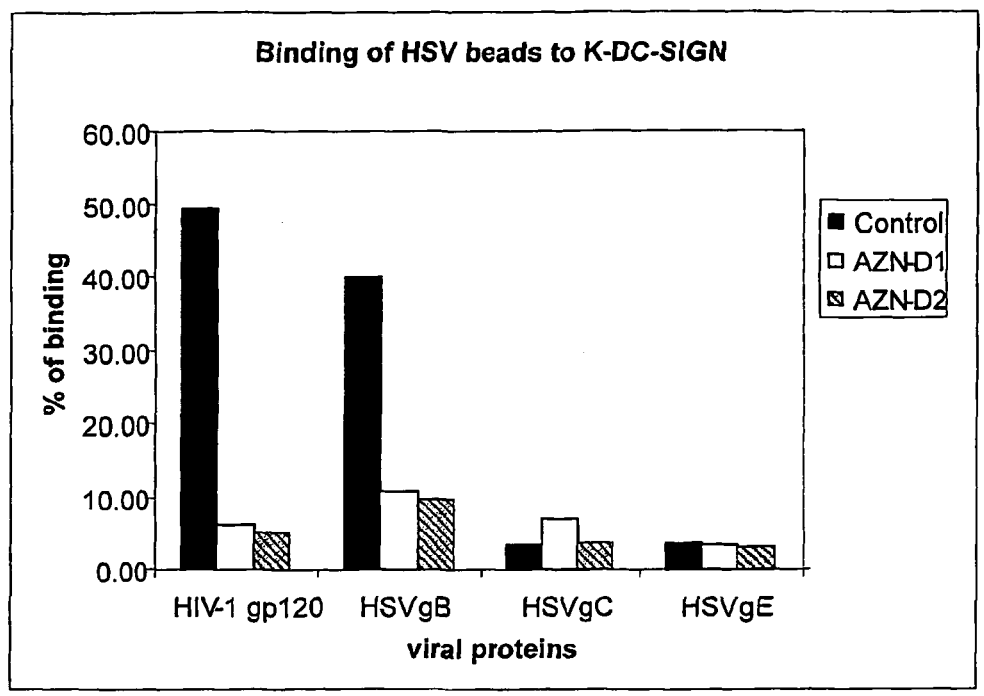
B
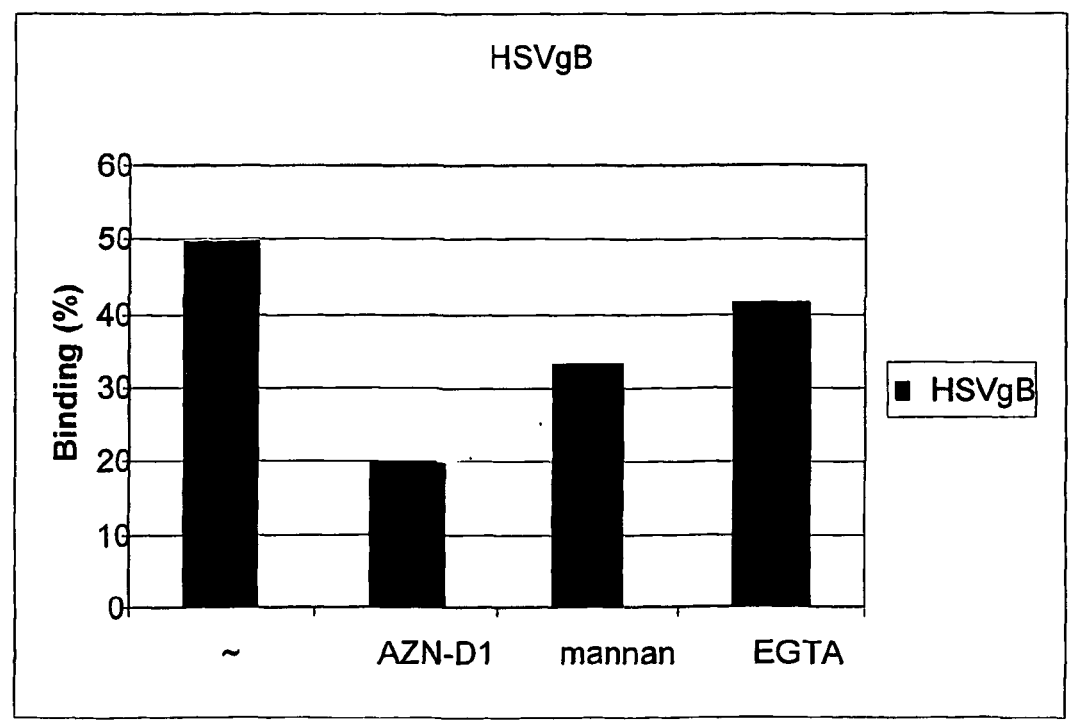

mSIGNR1 binds mannose-containing carbohydrates, similar to DC-SIGN and L-SIGN

Fig. 33C

Carbohydrate specificity of DC-SIGN, L-SIGN and mSIGNR1

| | DC-SIGN | L-SIGN | mSIGNR1 |
|---|---|---|---|
| LewisX | + | - | + |
| sialyl LewisX | - | - | + |
| sulfo LewisX | + | - | + |
| LewisY | + | + | + |
| LewisA | + | + | + |
| sialyl LewisA | - | - | + |
| sulfo LewisA | + | + | + |
| LewisB | + | + | + | pathogens with mannose-containing
carbohydrates bind mSIGNR1

Cellular DC-SIGN and L-SIGN bind HCV E1 and E2 proteins

DC-SIGN has similar binding site for
gp120 and HCV

Fig. 36D

Essential amino acid residues in DC-SIGN binding to its ligands gp120 and HCV envelope proteins

| DC-SIGN mutant | Adhesion | | | |
|---|---|---|---|---|
| | gp120 | HCV E1 | HCV E2 | HCV E1/E2 |
| | % | % | % | % |
| Wild type | 45 | 50 | 45 | 50 |
| E347Q | 4 | 3 | 7 | 7 |
| N349D | 0 | 5 | 9 | 7 |
| N365D | 0 | 5 | 9 | 9 |
| D366A | 3 | 4 | 5 | 6 |
| D320A | 7 | 4 | 6 | 5 |
| E324A | 0 | 4 | 7 | 6 |
| N350A | 1 | 4 | 8 | 5 |
| D355A | 2 | 4 | 8 | 7 |

E347Q, N349D, N365D: Ligand binding
D366A: $Ca^{2+}$ site 2
D320A, E324A, N350A, D355A: $Ca^{2+}$ site 1

Stable K562 transfectamts

HCV is internalized by DC-SIGN and L-SIGN; internalization pathway depends on cell-line Fig. 38
Immature and mature DC bind HCV via DC-SIGN
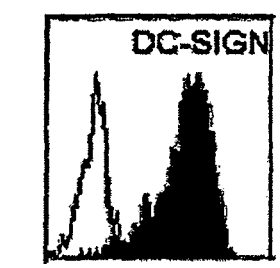
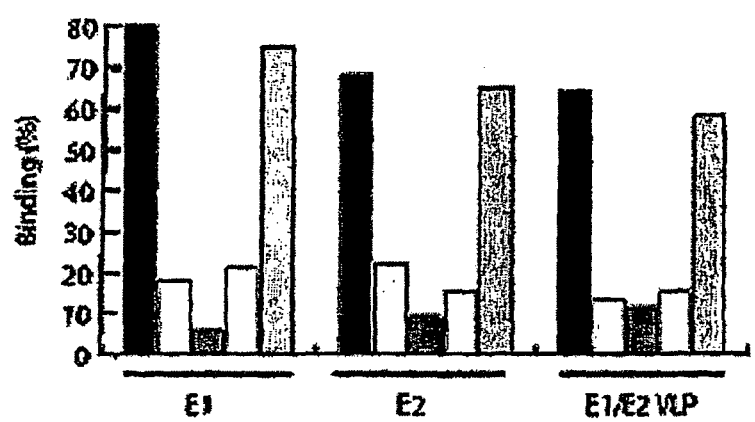
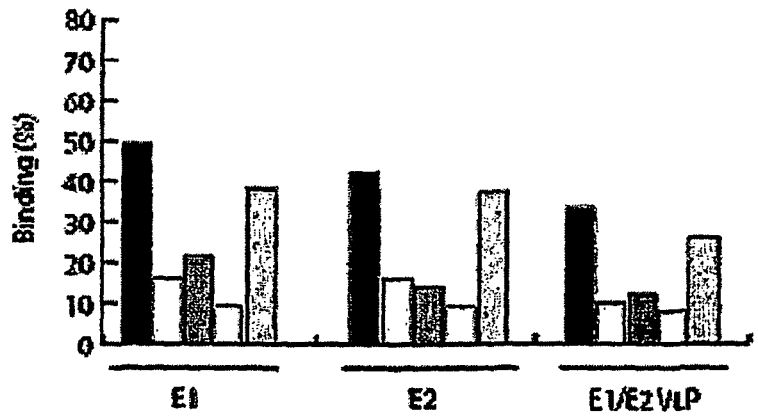

Immature DC capture and internalize HCV through DC-SIGN; HCV is targeted to the early endosomes Immature DC internalize carbohydrates via DC-SIGN HCV binding to Liver sections Fig. 42
Lewis blood group antigens and some of
their substructures bind to DC-SIGN.
a
| Structure | Antigen |
|---|---|
| Fucα1→ 2Galβ1→3GlcNAc | H type 1 |
| Fucα1→ 2Galβ1→4GlcNAc | H type 2 |
| →3 (Galβ1→4GlcNAcβ1→)ₙ | I-antigen |
| Galβ1→ 4GlcNAc<br>3<br>↑<br>Fucα1 | Lewis x (Le$^x$) |
| Fucα1 → 2Galβ1→ 4GlcNAc<br>3<br>↑<br>Fucα1 | Lewis y (Le$^y$) |
b 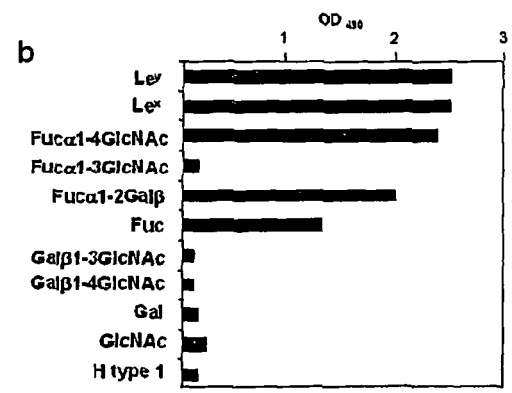
c 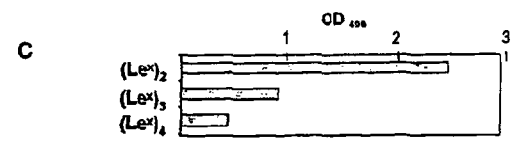

Binding of *H. pylori* is dependent on Lewis antigen expression.

Fig. 44

LPS phase variation in *H. pylori* occurs in vivo.

a

| Strain | Number of colonies (%) | Serotype | | | | |
|---|---|---|---|---|---|---|
| | | Le$^y$ | mono-Le$^x$ | (Le$^x$)$_n$ | i-antigen | H type 1 |
| J223.3 | 6/30 (20) | +++ | - | ++ | ++ | +++ |
| J223.8 | 24/30 (80) | - | - | - | +++ | +++ | b

| Strain | Length of C-tract in gene | | Serotype | | | | |
|---|---|---|---|---|---|---|---|
| | futA | futB | Le$^y$ | mono-Le$^x$ | (Le$^x$)$_n$ | i-antigen | H type 1 |
| J223.3 | n=9 ("off") | n=10 ("on") | +++ | - | ++ | ++ | +++ |
| J223.8 | n=9 ("off") | n=9 ("off") | - | - | - | +++ | +++ |
| J223.3 ΔfutB | N.D. | N.D | - | - | - | +++ | +++ | c

```
J223.3                                futA
1   ATGTTCCAAC CCCTATTAGA CGCCTTCATA
    GAAAGCGCTT CCATTGAAAA AATGGCCTCT
61  AAATCTCCCC CCCCCTAA (STOP)
                              (SEQ ID NO: 5)
J223.8

1   ATGTTCCAAC CCCTATTAGA CGCCTTCATA
    GAAAGCGCTT CCATTGAAAA AATGGCCTCT
61  AAATCTCCCC CCCCCTAA (STOP)
                              (SEQ ID NO: 5)
```

```
J223.3                                futB
1   ATGTTCCAAC CCCTATTAGA CGCCTTCATA
    GAAAGCGCTT CCATTGAAAA AATGGCCTCT
61  AAATCTCCCC CCCCCCTAAA AATC etc.
                              (SEQ ID NO: 5)
J223.8

1   ATGTTCCAAC CCCTATTAGA CGCCTTCATA
    GAAAGCGCTT CCATTGAAAA AATGGCCTCT
61  AAATCTCCCC CCCCCTAA (STOP)
                              (SEQ ID NO: 6)
```

DC-SIGN is expressed on gastric DCs and is the major receptor for Le positive *H. pylori*.

Fig. 46
Binding of *H. pylori* to induces DC-SIGN-dependent increase of IL-10 and IL-12 production, but no changes in IL12p70.
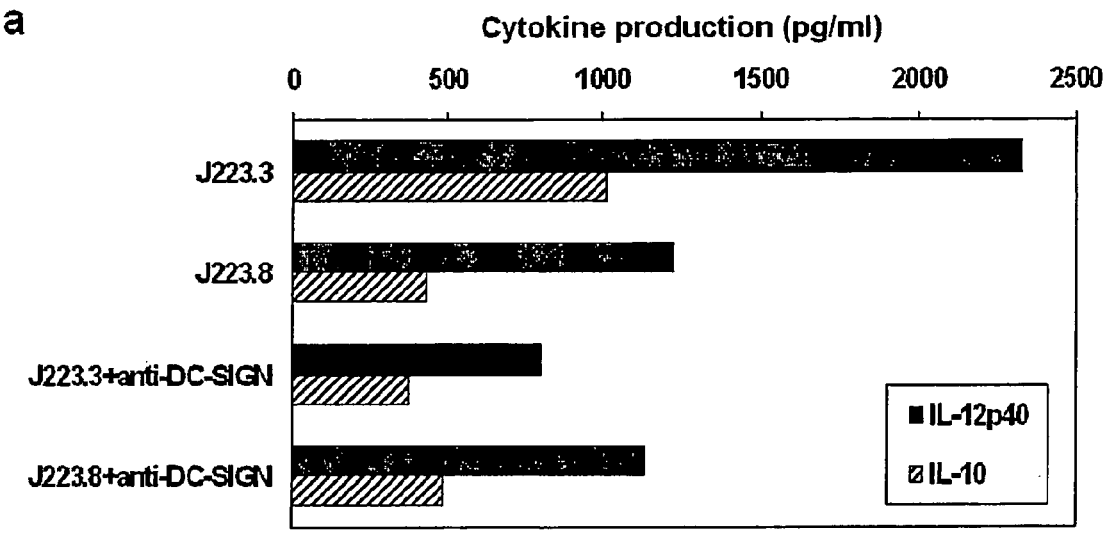
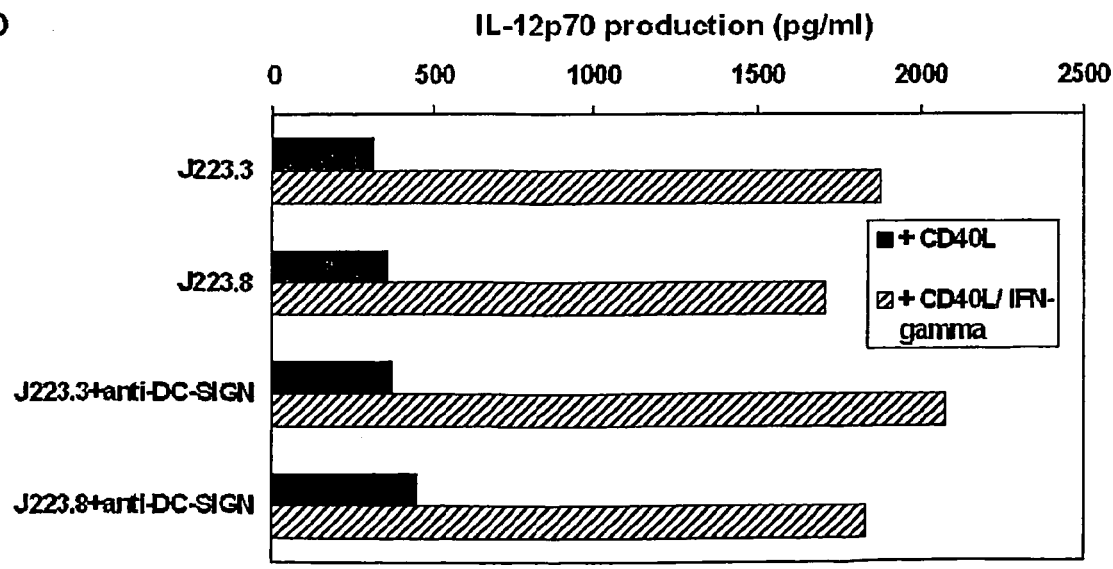

Binding of *H. pylori* to DC-SIGN induces skewing of naïve T cells to Th2.

PMN express the DC-SIGN ligand Lewis$^x$ and bind with high affinity to recombinant DC-SIGN.

CEACAM1 expressed on PMN is a ligand of DC-SIGN and binds through its Lewis$^x$ moieties.

Fig. 55
Cellular DC-SIGN expressed on K562 transfectants and immature DC binds native CEACAM1 from PMN.
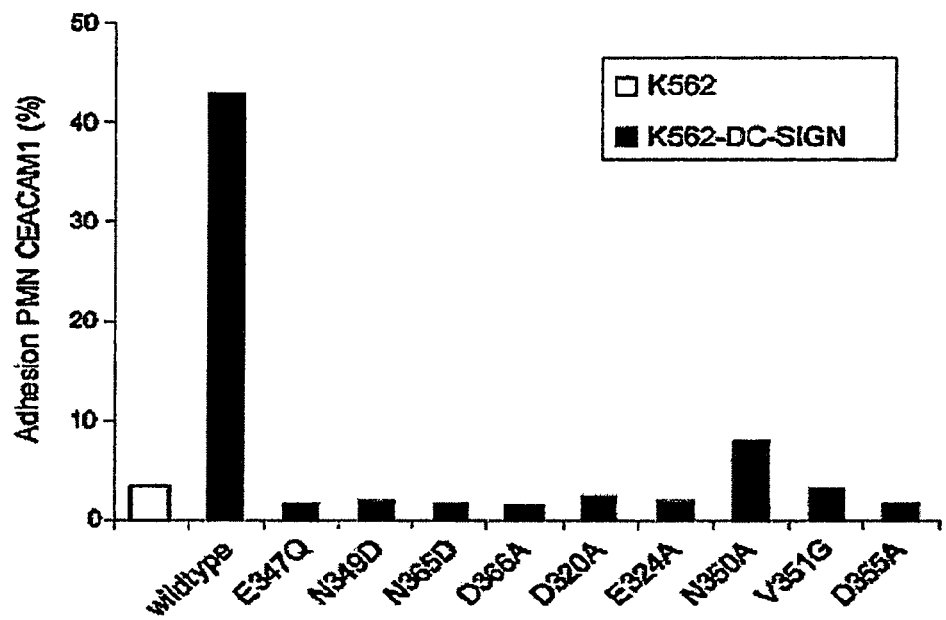
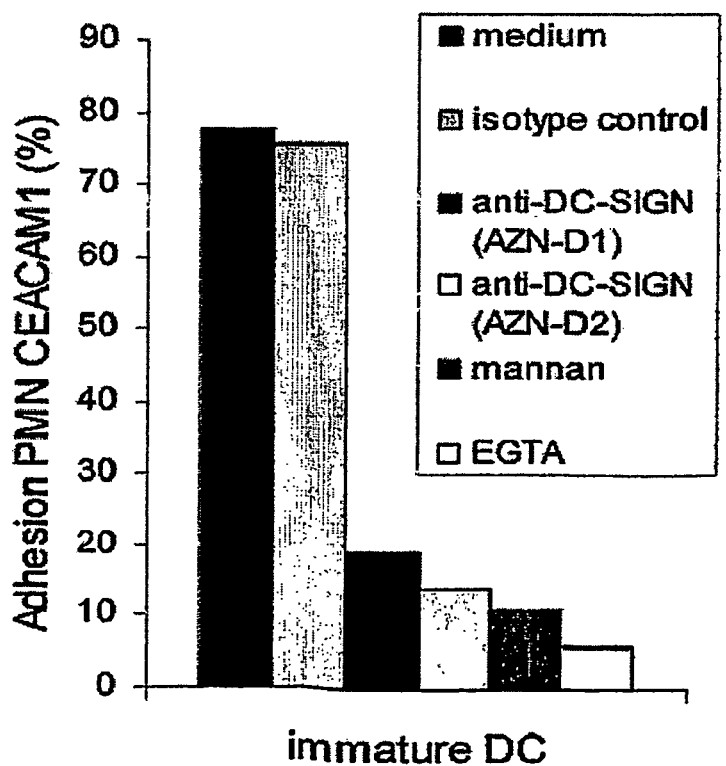
immature DC Fig. 56
DC-SIGN is involved in clustering of DC and PMN.
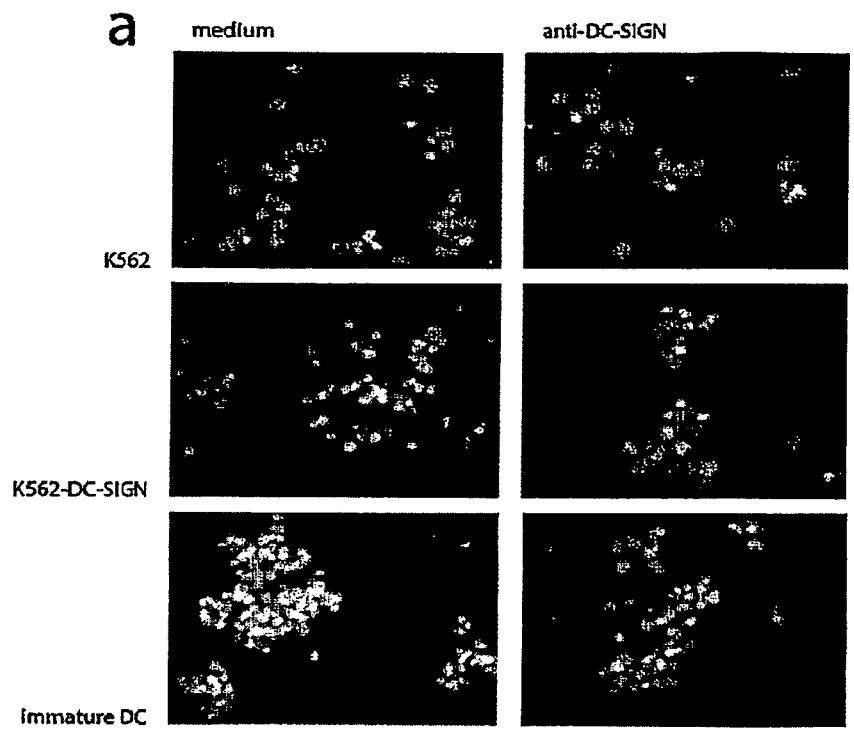
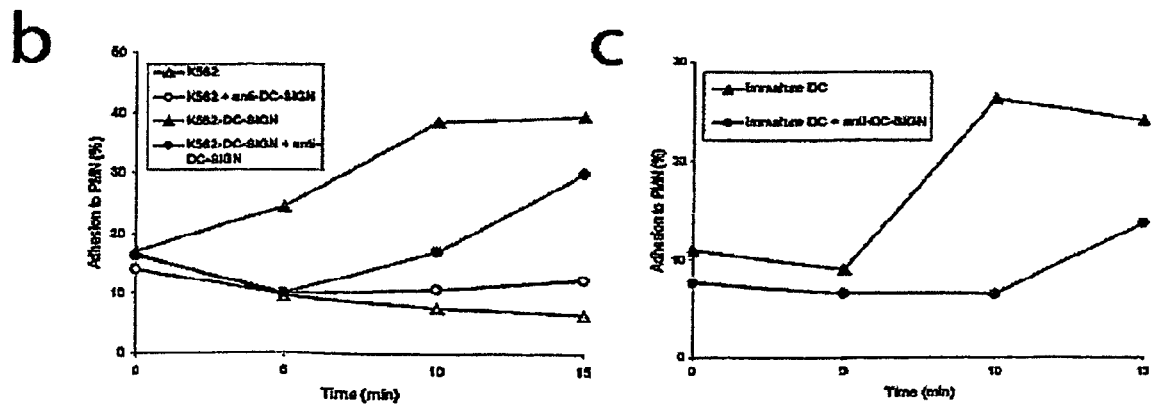

Localization of PMN and DC in colonic mucosa of patients with Crohn's disease.

Fig. 58
PMN activate immature DC through binding DC-SIGN.
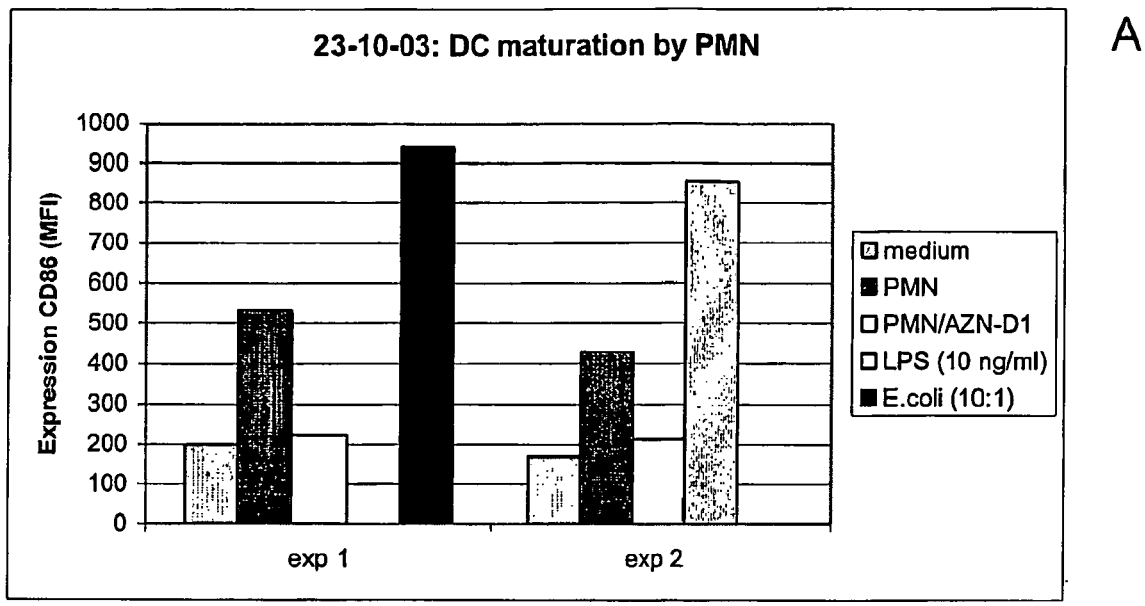
PMN induce upreguation of co-stimulatory CD86 on DC, which is dependent on DC-SIGN binding
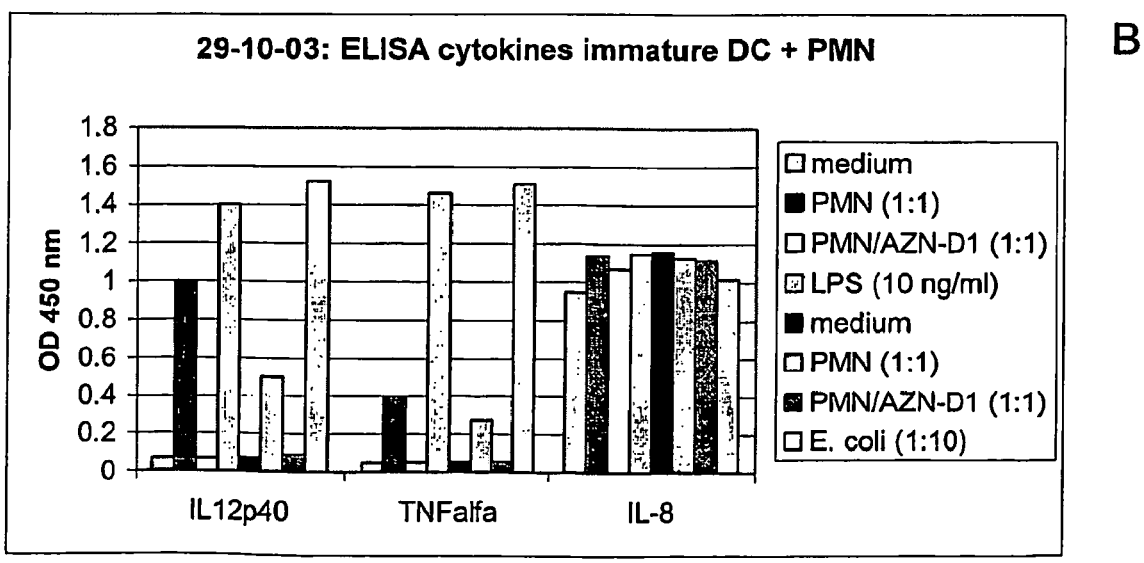
PMN induce secretion of inflammatory cytokines by DC, which is dependent on DC-SIGN binding Fig. 59
DC-SIGN binds Lex expressing CD11b present on neutroph
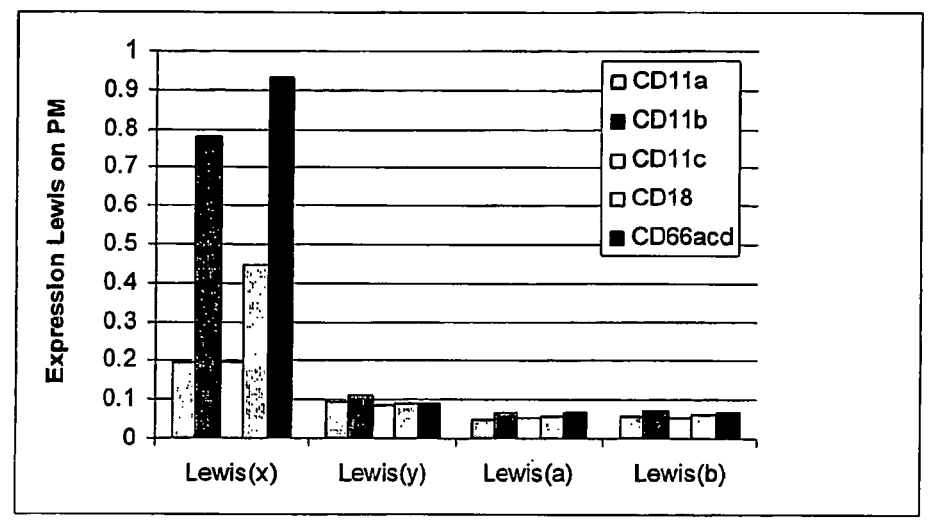
A
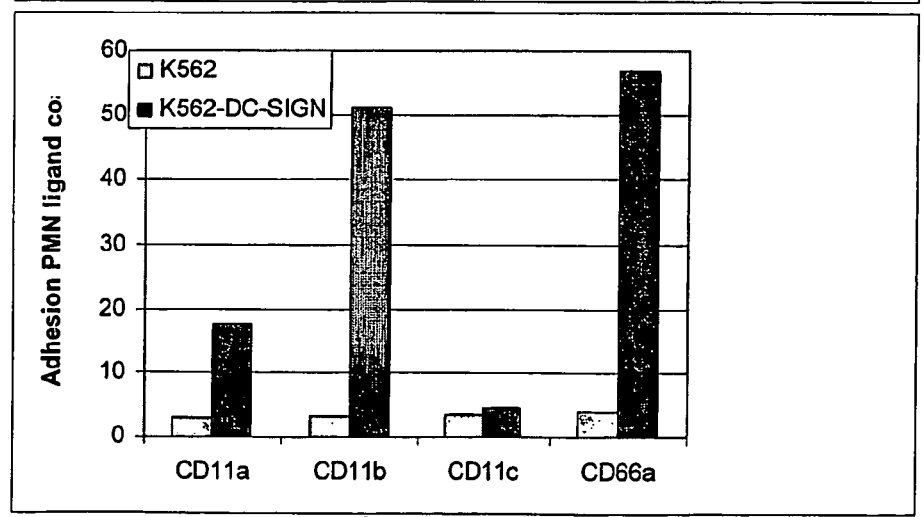
B
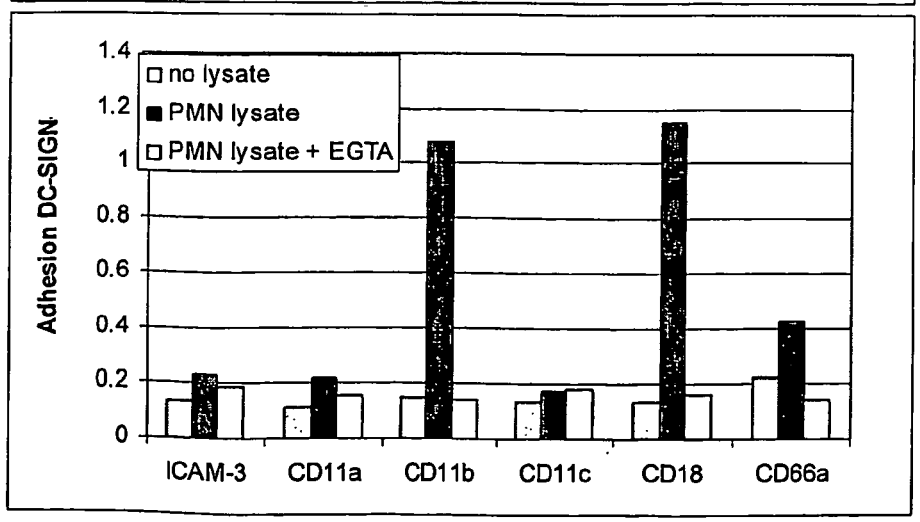
C

Fig. 59D

DC-SIGN bindsCD66acd and CD11b on PMN

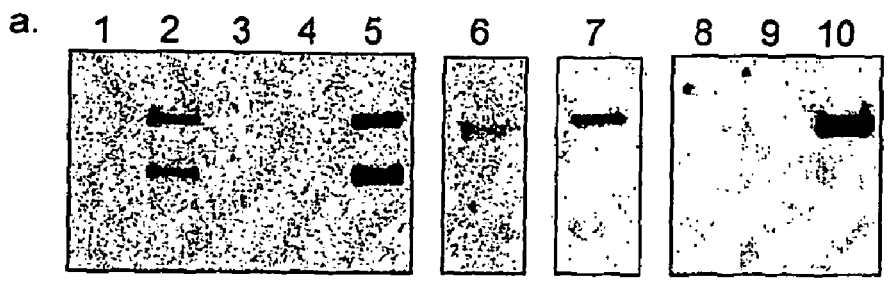

Biotinylated PMN:
1. IP ICAM-3-Fc, IB streptavidin,
2. IP DC-SIGN-Fc, IB streptavidin,
3. IP anti-DC-SIGN, IB streptavidin,
4. IP anti-CD66acd, IB streptavidin,
5. IP anti-CD11b, IB streptavidin,
6. IP DC-SIGN-Fc, IB anti-CD66acd,
7. IP DC-SIGN-Fc, IB anti-CD11b,
8 IP anti-DC-SIGN, IB DC-SIGN-Fc,
9. IP anti-CD66acd, IB DC-SIGN-Fc,
10. IP anti-CD11b, IB DC-SIGN-Fc.

IB, immunoblotting (detection/binding)
IP, immunoprecipitation (capture)

DC-SIGN binds Lewis on CD11b

Biotinylated PMN, IP anti-CD11b, IB streptavidin:
1. control
2. PNGaseF

Biotinylated SW948, IP anti-CD11b, IB DC-SIGN-Fc
3. control
4. PNGaseF

Biotinylated PMN, IP anti-CD11b, IB streptavidin:
5. control
6. α-1,3/4-Fucosidase

Biotinylated PMN, IP anti-CD11b, IB DC-SIGN-Fc
7. control
8. α-1,3/4-Fucosidase IB, immunoblotting (detection/binding)
IP, immunoprecipitation (capture)

Fig. 61
DC-SIGN binds tumor cells expressing CD66e
DC-SIGN binds the tumor antigen CD66e=CEA
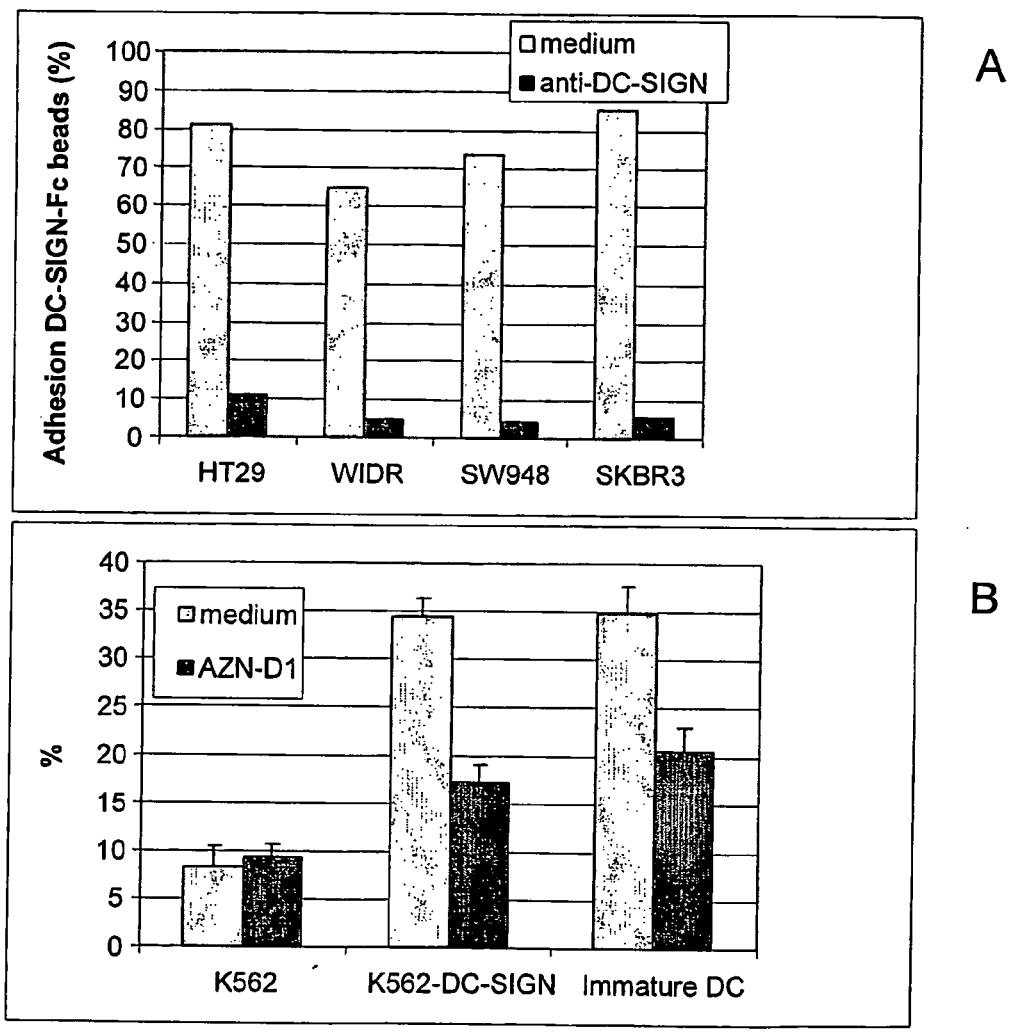
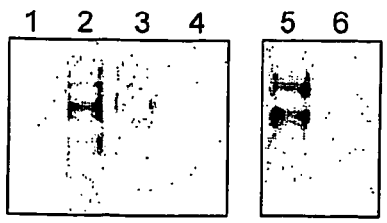
b. Biotinylated SW948:
1. IP ICAM-3-Fc, IB streptavidin,
2. IP DC-SIGN-Fc, IB streptavidin
3. IP anti-CD66ae, IB streptavidin
4. IP anti-CD11b, IB streptavidin
5. IP anti-CD66ae, IB DC-SIGN-Fc
6. IP anti-CD11b, IB DC-SIGN-Fc
IB, immunoblotting (detection/binding)
IP, immunoprecipitation (capture)

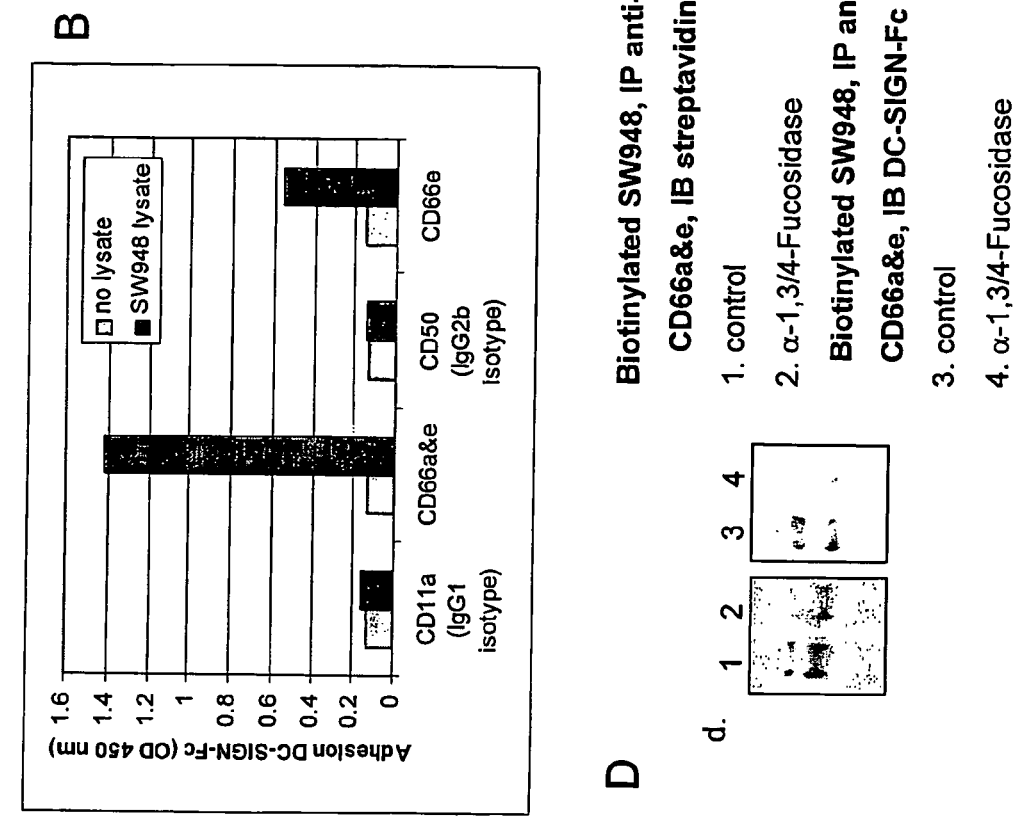
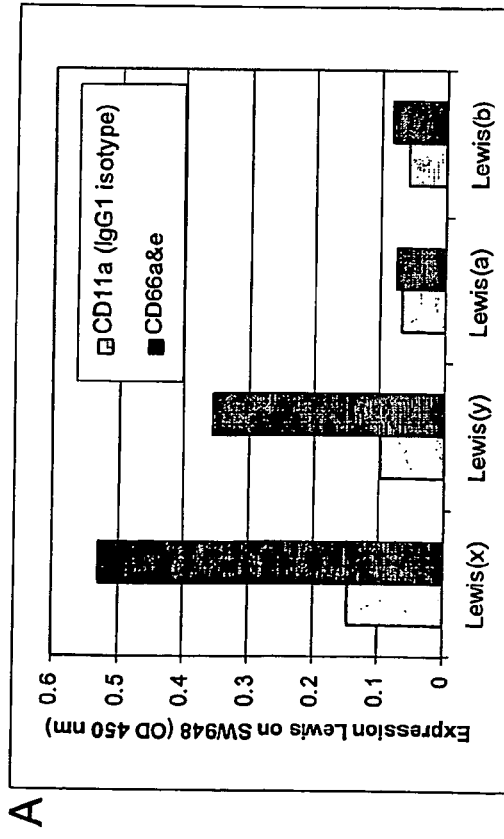
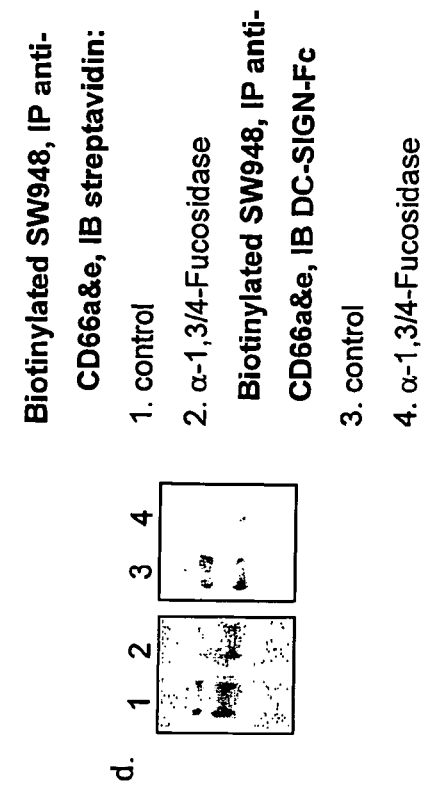
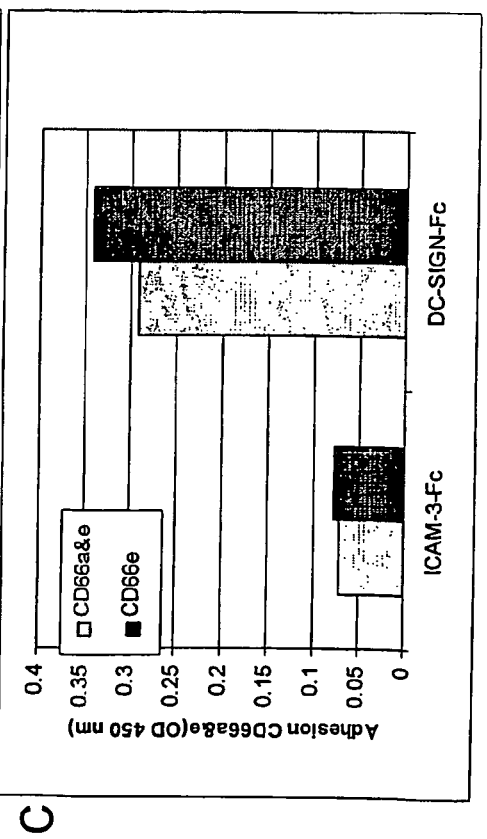
Fig. 62

Fig. 63

C-TYPE LECTIN BINDING MOLECULES, IDENTIFICATION AND USES THEREOF

This application is the U.S. National Phase of International Application Number PCT/NL2003/000781 filed on 7 Nov. 2003, which is incorporated herein by reference.

BACKGROUND OF THE INVENTION

The invention relates to the field of immunology. The invention in particular relates to the role of dendritic cells in immune responses and to pathogens that are able to capitalize thereon.

Dendritic cells (DC) are professional antigen presenting cells (APC) that induce cellular immunity upon pathogen recognition. These cells are therefore important in the defense against many pathogens[1;2;3]. Immature DC are seeded throughout peripheral tissues to act as sentinels against invading pathogens[4]. Upon pathogen capture, DC are activated, process pathogens for antigen presentation on Major Histocompatability Complex (MHC) class II molecules, and migrate to the secondary lymphoid organs where they activate naive T cells to initiate adaptive immune responses[1;3;4]. Depending on the pathogen that is recognized by the DC, differentiation of naive T cells into Th1 cells is triggered by DC in response to intracellular microbes, whereas Th2-mediated responses are generated by DC to eliminate pathogens residing extracellularly[3]. Thus DC play an important role in both innate and cellular immune responses against tumors antigens as well as pathogens such as viral, bacterial, fungal and parasitic infections[1;5]. Knowledge about cell-surface receptors on DC that are involved in recognition of pathogens is only starting to emerge, and include Toll-like receptors (TLR)[6;7] and C-type lectins[8]. TLR recognize specific pathogen-derived components, such as lipoproteins, lipopolysaccharides and bacterial DNA, and relay this information through intracellular signaling cascades leading to the production of regulatory cytokines and upregulation of MHC and costimulatory molecules that lead to activation/maturation of DC[6]. In contrast, C-type lectins recognize pathogen-derived carbohydrate structures and upon binding internalize pathogens for antigen processing and presentation to T cells[8-10]. In classical calcium-dependent lectins, conserved amino acid residues in the carbohydrate recognition domain (CRD) are involved in calcium binding and sugar specificity[11]. A growing number of C-type lectins are described to be specifically expressed by DC. For most of these lectins detailed knowledge about pathogen-targets as well as cellular ligands if any, including the identity of the carbohydrate structure they recognize, is lacking[8]. The DC-specific C-type lectin DC-SIGN (dendritic-cell specific ICAM-3 grabbing nonintegrin, CD209) is involved in binding of the HIV-1 envelope glycoprotein by DC to enhance infection of T cells[12], while the mannose receptor (MR) is involved in recognition of mycobacteria and Fungi/Protozoa[13], Some C-type lectins like DC-SIGN can interact with carbohydrate-bearing self glycoproteins (ICAM-2 and ICAM-3) to mediate cellular adhesion processes[14;15].

DESCRIPTION OF THE INVENTION

In one aspect of the present invention it was found that a C-type lectin can comprise specificity for more than one type of glycoconjugate. This knowledge is useful for a variety of purposes. For instance, lectins are instrumental in mediating pathogen binding and the presentation of antigens thereof in dendritic cells. This binding property of C-type lectins is utilized by a number of pathogens to at least in part facilitate infection of an individual. Knowledge of glycoconjugate specificity of such lectins therefore provides an entrance to the development of medicaments capable of interfering with the capacity of carbohydrates present on pathogens to interact with the lectin and thereby at least in part interfere with the infection or the severity thereof in the exposed individual. In one embodiment the invention therefore provides a method for at least in part inhibiting the binding of a ligand to a C-type lectin or a carbohydrate binding part thereof, comprising contacting said C-type lectin with an isolated and/or recombinant glycoconjugate comprising at least two mannose residues in α1,2 linkage or a glycoconjugate comprising a fucose residue or a glycoconjugate comprising at least one end standing N-acetylglucosamine or a derivative or multimer thereof. Also provided is the use of a glycoconjugate comprising at least two mannose residues in α1,2 linkage or a glycoconjugate comprising a fucose residue or a glycoconjugate comprising at least one end standing N-acetylglucosamine or a derivative or multimer thereof for at least in part inhibiting the binding of a ligand to a C-type lectin or a carbohydrate-binding part thereof. This method may be used for instance to study the exact binding properties of the lectin. The method is also of use in identifying compounds capable of interfering with an ability of said C-type lectin to bind to pathogens. In a preferred embodiment said method further comprises a cell comprising said C-type lectin. Preferably said cell is an antigen presenting cell, more preferably a dendritic cell or macrophage. In the presence of such cell, the effect of such inhibition may be compared to the function of the antigen presenting cell, for instance on its capacity to present antigen and/or the production of lymphokines and/or cytokines. In a preferred embodiment said C-type lectin comprises DC-SIGN, mSIGNR1, L-SIGN and/or DC-SIGNR. Whereas DC-SIGNR and L-SIGN are predominantly expressed on macrophage/endothelial cells, on lymph node and on liver sinusoidal endothelial cells and DC-SIGN is expressed predominantly on dendritic cells. DC-SIGNR and L-SIGN share the remarkable binding and signaling effects that ManLAM has upon binding to dendritic cells via DC-SIGN. However, whereas DC-SIGN further comprises a particular specificity for glycoconjugates comprising a fucose residue or a derivative or multimer thereof, DC-SIGNR and L-SIGN are lacking such particular specificity. In the present invention there is thus a preference for the C-type lectin DC-SIGN.

With the term "glycoconjugate comprising a fucose residue" is meant a glycoconjugate comprising at least one fucose residue that is α1,3 or α-1,4-linked to the glycoconjugate. The linking moiety preferably consists of N-acetylglucosamine. The linking moiety is preferably coupled to an oligosaccharide or glycan, which in turn may be part of a larger structure (or carrier molecule) comprising subsequent glycoconjugates comprising a fucose residues, or other compounds such as mannose in any configuration. A derivative of said glycoconjugate comprising a fucose residue comprises the same C-type lectin binding activity in kind not necessarily in amount. A derivative may be generated through modification of the fucose residue. Such modifications may be generated in various ways. Preferably, said fucose is a terminal fucose, i.e. linked via only one α1,3 or α-1,4 linkage to another molecule or fucose. Preferred examples of glycoconjugates comprising a fucose residue are Lewis bloodgroup antigens Le$^x$, Le$^y$, Le$^a$, Le$^b$ and/or LDNF. C-type lectin binding parts, derivatives and/or analogous of the lewis bloodgroup antigens are of course also within the scope of the invention. Different modifications have different effects on the lectin binding properties. Sialylation of Le$^x$ (yielding sialyl-Le$^x$, a L-, E- and P-selectin ligand) completely abrogates the recognition by DC-SIGN, indicating that DC-SIGN has a carbohydrate specificity that is distinct from that of the selectins that mediate leukocyte rolling. Sulfation reduces the binding affinity of DC-SIGN for Le$^x$, as well as Le$^a$ (FIG. 2a). A derivative of a glycoconjugate comprising a fucose residue thus comprises a modification wherein said modification allows binding of said glycoconjugate to said C-type lectin. Glycoconjugates comprising multiple fucose residues in the configuration of a lewis bloodgroup antigen typically have a higher binding affinity than a glycoconjugate comprising a single fucose residue.

With the term "glycoconjugate comprising at least two mannose residues in α1,2 linkage" is meant a glycoconjugate comprising at least two mannose residues wherein said mannose residues are linked to each other via an α1,2 linkage and wherein one of the mannose residues is linked to the glycoconjugate. The linking moiety preferably but not necessarily comprises mannose in α-1,5 linkage and arabinan or β-D-arabinose. The linking moiety is preferably coupled to an oligosaccharide or glycan, which in turn may be part of a larger structure (or carrier molecule) comprising subsequent glycoconjugates comprising at least two mannose residues in α1,2 linkage, or other compounds such as fucose in any configuration. A derivative of said glycoconjugate comprising at least two mannose residues in α1,2 linkage comprises the same C-type lectin binding activity in kind not necessarily in amount. A derivative may be generated through modification of one or both of the mannose residues. Such modifications may be generated in various ways. Preferably, said at least two mannose residues in α1,2 linkage are terminal residues, i.e. linked via only linkage to another molecule or mannose. In a preferred embodiment said glycoconjugate comprising at least two mannose residues in α1,2 linkage, comprises two or three mannose residues linked to each other via respectively one and two α1,2 linkages. A particularly preferred example of a of glycoconjugates comprising at least two mannose residues in α1,2 linkage is ManLAM. ManLAM comprises a mannose-capped lipoarabinomannan, such as derivable from the cell wall component of Mycobacterium. The mannose-capped lipoarabinomannan is preferably linked to an oligosaccharide or glycan, which in turn may be part of a larger structure (or carrier molecule) comprising subsequent mannose-capped lipoarabinomannans or other compounds such as fucose in any configuration. C-type lectin binding parts, derivatives and/or analogous of ManLAM are of course also within the scope of the invention. Different modifications have different effects on the lectin binding properties. Glycoconjugates comprising two or more sets of at least two mannose residues in α1,2 linkage typically have a higher binding affinity than a glycoconjugate comprising only one set of at least two mannose residues in α1,2 linkage.

With the term "glycoconjugate comprising a N-acetylglucosamine residue" is meant a glycoconjugate comprising at least one end-standing N-acetylglucosamine residue that is linked to the glycoconjugate. The N-acetylglucosamine is preferably directly linked to an asparagin of the glycoconjugate. The glycoconjugate can in turn be part of a larger structure (or carrier molecule) comprising subsequent glycoconjugates comprising N-acetylglucosamine residues, or other compounds such as mannose or fucose in any configuration. A derivative of said glycoconjugate comprising a N-acetylglucosamine residue comprises the same C-type lectin binding activity in kind not necessarily in amount. A derivative may be generated through modification of the N-acetylglucosamine residue. Such modifications may be generated in various ways. Preferably, said N-acetylglucosamine is a terminal N-acetylglucosamine, i.e. linked to the asparagin. Preferred examples of glycoconjugates comprising a N-acetylglucosamine residue. A derivative of a glycoconjugate comprising a N-acetylglucosamine residue thus comprises a modification wherein said modification allows binding of said glycoconjugate to said C-type lectin. Glycoconjugates comprising multiple N-acetylglucosamine residues typically have a higher binding affinity than a glycoconjugate comprising a single N-acetylglucosamine residue.

A glycoconjugate can be mono- or polyvalent for the respective mannose, fucose or N-acetylglucosamine residues. A polyvalent glycoconjugate comprises at least two separate antennae wherein at least two said antennae comprise said residues. In a preferred embodiment a polyvalent glycoconjugate comprises at least two antennae having a terminal fucose, i.e. linked via only one α1,3 or α-1,4 linkage to the glycoconjugate or to another fucose residue. In a preferred embodiment a polyvalent glycoconjugate comprises at least two antennae having at least two mannose residues in α1,2 linkage. In yet another embodiment a polyvalent glycoconjugate comprises at least two antennae having a terminal N-acetylglucosamine, i.e. linked via only one linkage to the glycoconjugate. A multimer is preferably a polyvalent glycoconjugate A binding molecule can be specific for a monovalent or a polyvalent glycoconjugate. Binding of the binding molecule is typically stronger to the polyvalent glycoconjugate.

Binding of the C-type lectin and more in particular, subsequent action of the cell carrying the C-type lectin is typically significantly higher in case of binding of a polyvalent glycoconjugate. This is in particular so for glycoconjugates comprising at least one end standing N-acetylglucosamine residue.

Carrier molecules may further comprise a large variety of different molecules including peptide, protein, lipid, polysaccharide and also synthetic molecules not expressly mentioned here. The carrier molecule(s) may of course be part of an even larger structure such as a biological or artificial surface, a virus, a bacterium or a eukaryotic cell.

Binding of the ligand to the C-type lectin can be inhibited by interfering with binding site on the ligand, with binding site of the C-type lectin or both. Interference with the binding site of the ligand can be done using a ligand binding molecule capable of specifically binding to the C-type lectin binding part on the ligand. This is preferably done with a proteinaceous molecule such as a carbohydrate specific antibody preferably specific for a glycoconjugate comprising at least two mannose residues in α1,2 linkage or a glycoconjugate comprising a fucose residue or a glycoconjugate comprising at least one end standing N-acetylglucosamine or a derivative or multimer thereof. The experimental part describes non-limiting examples of such antibodies. Non-limiting examples of antibodies comprising a specificity for a glycoconjugate comprising a fucose residue or a derivative or multimer thereof are SMLDN1.1 or SMFG4.1, 6H3, Hp151, 4D2, 54.1F6A, NAM61-1A2 or SMLDN1.1. The ligand binding molecule can also be a C-type lectin, preferably a soluble derivative thereof, comprising specificity for a glycoconjugate comprising at least two mannose residues in α1,2 linkage or a glycoconjugate comprising a fucose residue or a glycoconjugate comprising at least one end standing N-acetylglucosamine or a derivative or multimer thereof. A non-limiting example of a soluble C-type lectin of the invention is a soluble DC-SIGN-Fc chimeric molecule comprising amino acid residues 64-404 fused at the C-terminus to a human IgG1-Fc fragment as described for instance in Geijtenbeek et al (Geijtenbeek et al 2002, J. Biol. Chem. 277:11314-11320). However, soluble C-type lectins comprising one or more of the provided specificities can be generated in various ways (for instance by derivation from DC-SIGNR or L-SIGN). Now that the present invention describes one chimeric molecule others can be generated, for instance as described in Fawcett J et al (Fawcett J et al 1992, Nature 360:481-4).

Interference with the binding site on the C-type lectin can of course also be done in various ways. Interference with the binding site on the C-type lectin can be done using a C-type lectin binding molecule capable of specifically binding to the ligand binding part on the C-type lectin. This is preferably done with a proteinaceous molecule such as a C-type lectin specific antibody or with a glycoconjugate comprising at least two mannose residues in α1,2 linkage or a glycoconjugate comprising a fucose residue or a glycoconjugate comprising at least one end standing N-acetylglucosamine or a derivative or multimer thereof, wherein said glycoconjugate or both may be part of a larger structure. Binding can of course further be inhibited by sterically hindering the binding of the ligand to the C-type lectin. For this it is not absolutely required that the interfering molecule itself binds to the association site of the carbohydrate and the C-type lectin. Binding can also be interfered with successfully steric hindrance by binding of the interfering molecule in the vicinity of the site of association.

The ligand may be any type of structure capable of binding to said C-type lectin. Usually this will comprise a proteinaceous molecule or a carbohydrate. The ligand may be an antibody. It is preferred, but not strictly necessary, that the ligand comprises mannosilated glycans such as cell wall component of Mycobacterium ManLAM, or a mannose derivative, lipophosphoglycan such as derived from *Leishmania*, or a glycoconjugate comprising at least two mannose residues in α1,2 linkage or a glycoconjugate comprising at least one end standing N-acetylglucosamine or a glycoconjugate comprising a fucose residue such as SEA or CD66 or a derivative or multimer thereof The ligand can have instead of, or in addition to, a glycoconjugate comprising at least two mannose residues in α1,2 linkage or a glycoconjugate comprising a fucose or a glycoconjugate comprising at least one end standing N-acetylglucosamine or a derivative or multimer thereof, different glycoconjugates capable of binding to the same on the C-type lectin.

The ligand preferably comprises an antigen. The ligand can, as mentioned above, comprise a glycoconjugate comprising a fucose residue, at least two mannose residues or at least one end standing N-acetylglucosamine. In this embodiment the antigen does or does not comprises said glycoconjugate. In a preferred embodiment the antigen comprises said glycoconjugate. The ligand preferably comprises a (tumor) antigen, a pathogen and/or a cell associated receptor. An antigen is here used to include peptides or glycolipids and derivatives thereof capable of being presented in the context of MHC class I or class II, or CD1b. At least some C-type lectins, and particularly those expressed on dendritic cells are involved in the process of antigen uptake and presentation thereof by antigen presenting cells. An early step in this process is the capture of the antigen by such lectins. With a method of the invention it is possible to at least in part interfere with this initial step in the process of antigen presentation. Considering the importance of antigen presentation in the initiation and maintenance of antigen specific immune responses, it is clear that the method of the invention can be favorably used to at least in part diminish the potency of an immune response against said antigen.

In a particularly preferred embodiment the ligand comprises a pathogen or a C-type lectin binding part thereof. It has been found that many different pathogens comprise carbohydrates capable of binding to C-type lectins of the invention. In particular it has been found that pathogens or parts thereof can bind to said C-type lectins through a mannose containing glycoconjugate such as a glycoconjugate comprising at least two mannose residues in α1,2 linkage or a glycoconjugate comprising a fucose or a glycoconjugate comprising at least one end standing N-acetylglucosamine or derivative or multimer thereof This binding at least in part facilitates infection of an individual with said pathogen. Interference with the binding of the pathogen or part thereof to the C-type lectin can thus at least in part aid an individual in combating an infection by the pathogen and in cases even prevent the establishment of a clinically visible symptoms thereof. The latter is useful in (passive or active) vaccination strategies. The pathogen can be a virus, a fungus, a (myco)bacterium and/or a parasite. The pathogen preferably comprises a glycoconjugate comprising at least two mannose residues in α1,2 linkage or a glycoconjugate comprising a fucose residue or a glycoconjugate comprising at least one end standing N-acetylglucosamine or a derivative or multimer thereof Examples of preferred pathogens are human immunodeficiency virus, a *helicobacter*, a *neisseria meningitidis*, a *leishmania*, a *schistosoma*, a *klebsiella*, a probiotic *lactobacillus*, hepatitis C virus, a herpes simplex virus or an ebola virus. Inhibition of binding of the specifically mentioned pathogens can be achieved using a glycoconjugate comprising at least two mannose residues in α1,2 linkage or a glycoconjugate comprising a fucose residue or a glycoconjugate comprising at least one end standing N-acetylglucosamine or a derivative or multimer thereof In a particularly preferred embodiment inhibition of binding is achieved using a ligand (pathogen or part thereof) binding molecule capable of specifically binding to the C-type lectin binding part on the ligand. This is preferably done with a proteinaceous molecule such as a carbohydrate specific antibody preferably specific for a mannose carbohydrate such as a glycoconjugate comprising at least two mannose residues in α1,2 linkage or a glycoconjugate comprising a fucose residue or a glycoconjugate comprising at least one end standing N-acetylglucosamine or a derivative or multimer thereof The experimental part describes non-limiting examples of such antibodies. The ligand binding molecule can also be a C-type lectin, preferably a soluble derivative thereof, comprising specificity for a mannose carbohydrate such as a glycoconjugate comprising at least two mannose residues in α1,2 linkage or a glycoconjugate comprising a fucose residue or a glycoconjugate comprising at least one end standing N-acetylglucosamine or a derivative or multimer thereof A non-limiting example of a soluble C-type lectin of the invention is a soluble DC-SIGN-Fc as mentioned above. Thus infections of an individual with said pathogens can at least in part be prevented or treated by administering to said individual a mannose carbohydrate such as a glycoconjugate comprising at least two mannose residues in α1,2 linkage or a glycoconjugate comprising a fucose residue or a glycoconjugate comprising at least one end standing N-acetylglucosamine or a derivative or multimer thereof. In a preferred embodiment a ligand binding molecule of the invention is administered to said individual. This embodiment can also be used to at least in part inhibit the binding of the pathogen to a C-type lectin expressing cell thereby at least in part inhibiting the contamination or spread of the pathogen in the body of a patient, as well as inhibiting DC maturation and cell adhesion, as is also described below.

C-type lectins not only recognize carbohydrate profiles on pathogens but also interact with self glycoproteins to mediate cellular processes such as differentation and migration. A method of the invention can therefore also be used to interfere with the interaction with one or more self-glycoproteins and thereby be used to at least in part inhibit the cellular processes that the mentioned C-type lectins are involved in. This can be done by providing the carbohydrates structures provided by the invention (i.e. mannose containing glycojugate such as a glycoconjugate comprising at least two mannose residues in α1,2 linkage or a glycoconjugate comprising a fucose residue or a glycoconjugate comprising at least one end standing N-acetylglucosamine or derivative or multimer thereof). Preferably, this is achieved using a ligand binding molecule of the invention. Thus in another preferred embodiment the method is used to at least in part inhibit binding of said C-type lectin to a self-glycoprotein preferably a receptor present on the outer membrane of a cell. Preferably said receptor comprises ICAM-2, ICAM-3, CD11b, CD166 or CD66 or a functional part, derivative and/or analogue thereof CD166 and CD66 are present on a subset of NK cells and granulocytes. Within the subset of CD66 variants the receptor preferably comprises CD66a and/or CD66e. Thus interaction of these cells with a cell comprising a mentioned C-type lectin can be at least in part inhibited using a specific binding partner for a C-type lectin mentioned above. Thus interaction of preferably dendritic cells and said subset of NK cells and granulocytes can be interfered with. Through this interaction it is possible to modify an immune response. For instance, by at least in part inhibiting binding of a granulocyte to a dendritic cell, through providing a binding molecule of the invention, the C-type lectin of the invention, it is possible to at least in part inhibit the mounting of an effective immune response against antigens carried by the granulocyte. On the other hand it is possible to augment or induce an effective antigen specific immune response by providing the antigen presenting cell with a ligand comprising said antigen and a glycoconjugate comprising at least two mannose residues, a fucose residue and/or an end standing N-acetylglucosamine. Preferably, said C-type lectin comprises DC-SIGN. As specific binding partner of said C-type lectin a mannose containing glycoconjugate such as a glycoconjugate comprising at least two mannose residues in α1,2 linkage or a glycoconjugate comprising a fucose residue or a glycoconjugate comprising at least one end standing N-acetylglucosamine or a derivative or multimer thereof, can be advantageously used. The cellular interaction of DC with granulocytes or NK cells is essential in the innate immune response. In particular granulocytes are involved early ingestion of pathogens and may attract and stimulate DC to participate in pathogen recognition and presentation to T cells. In contrast NK cells are well know to be involved in killing of infected cells. NK cells can kill or activate DC that allow lysis of pathogen captured DC or maturation of pathogen captured DC to enhance T cell stimulation and immune response. The cellular interaction of granulocytes and NK cells with DC is to enhance immunity against pathogens or eliminate pathogen infected DC.

In another aspect the invention provides a method for at least in part inhibiting maturation or activation of an antigen presenting cell comprising providing said antigen presenting cell with a DC-sign binding glycoconjugate comprising at least two mannose residues, a fucose residue and/or an N-acetylglucosamine residue. Using this technique it is possible to for instance dampen an immune response. It is further possible to induce antigen tolerance through this method, one can for instance provide antigen together with the glycoconjugate. In case the antigen present cell is activated through a toll-like receptor pathway the balance between the level of activation/inhibition determines the maturation or activation of the antigen presenting cell. When the TLR pathway is activated strongly whereas the C-type lectin pathway is not, the balance is shifted toward activation of the antigen presenting cell whereas in the reverse situation the balance is shifted toward to tolerazing and inhibition of maturation or activation.

In another aspect the invention provides a method for modulating the stimulating immune effect of a dendritic cell that is preferably activated via a Toll-like receptor signaling pathway, said method comprising contacting said dendritic cell with an isolated and/or recombinant specific C-type lectin binding molecule. Preferably, said C-type lectin comprises DC-SIGN and said specific C-type lectin binding compound comprises a glycoconjugate comprising at least two mannose residues in α1,2 linkage or a glycoconjugate comprising a fucose residue or a glycoconjugate comprising at least one end standing N-acetylglucosamine or a derivative, a combination or multimer thereof and preferably, a glycoconjugate comprising at least two mannose residues in α1,2 linkage, preferably ManLAM. In combination with Toll-like receptor signaling ManLAM binding to DC-SIGN on a dendritic cell induces the production of significant amounts of IL-10 and reduces DC-activation/maturation. The production of IL-10 and reduction of activation/maturation of DC lead to a dampening of immune responses. Thus by providing a glycoconjugate comprising at least two mannose residues in α1,2 linkage or an analogously acting glycoconjugate to a dendritic cell, this cell can be induced to dampen the immune response at least in its direct vicinity. Thus an active immune system comprising a number of dendritic cells participating in the activity can be dampened through by providing the dendritic cell with a glycoconjugate comprising at least two mannose residues in α1,2 linkage or an analogously acting glycoconjugate. This embodiment is useful in situations where an individual is suffering from or at risk of suffering from an over-active immune system. Preferably, said over-active immune system involves graft versus host disease, host versus graft disease and the various auto-immune diseases. Alternatively, an immune system dampened through the discussed mechanism can be stimulated by providing dendritic cells with a specific C-type lectin binding molecule capable of interfering with the binding of a glycoconjugate comprising at least two mannose residues in α1,2 linkage or analogously acting glycoconjugate. ManLAM, at least in amounts active locally, is tolerated by individuals considering that active amounts of ManLAM are secreted by mycobacterium infected cells in the body. Alternatively, the dampened system can be stimulated by using a ligand binding molecule of the invention, preferably a proteinaceous molecule such as a carbohydrate specific antibody preferably specific for any mannose containing glycoconjugate such as ManLAM or a glycoconjugate comprising a fucose residue or a derivative or multimer thereof. Preferably, said antibody comprises a specificity for a mannose residue in α1,2 linkage with another mannose. The experimental part describes non-limiting examples of such antibodies. The ligand binding molecule can also be a C-type lectin, preferably a soluble derivative thereof, comprising specificity for a glycoconjugate comprising at least two mannose residues in α1,2 linkage or a glycoconjugate comprising a fucose residue or a glycoconjugate comprising at least one end standing N-acetylglucosamine or a derivative or multimer thereof Another non-limiting example of such an interfering molecule is AraLAM. This embodiment is useful to combat (chronic) diseases wherein at least part of the phenotype of the disease is due to dampening of the immune system through the mentioned C-type lectin pathway. Preferred examples of such diseases are infections by a human immunodeficiency virus, a *helicobacter*, a *neis-* seria meningitidis, a *leishmania*, a *schistosoma*, a *klebsiella*, a probiotic *lactobacillus*, hepatitis C virus, a herpes simplex virus or an ebola virus Human immunodeficiency virus binds to DC-SIGN through a glycoconjugate having at least two mannose residues. *Helicobacter* and particularly *helicobacter pylori* binds to DC-SIGN through a glycoconjugate having a lewis$^x$ antigen. *Neisseria meningitidis* binds to DC-SIGN through a glycoconjugate having N-acetylglucosamine residue. *Leishmania mexicana* binds to DC-SIGN through a glycoconjugate having at least two mannose residues. *Schistosoma mansoni* binds to DC-SIGN through a glycoconjugate having a lewis antigen. *Klebsiella pneumonea* binds to DC-SIGN through a glycoconjugate having at least two mannose residues. Hepatitis C virus binds to DC-SIGN through a glycoconjugate having at least two mannose residues. Herpes simplex virus binds to DC-SIGN through a glycoconjugate having at least two mannose residues. Ebola virus binds to DC-SIGN through a glycoconjugate having at least two mannose residues.

To alter the immune response in a body against the mentioned pathogens, a binding molecule of the invention thus preferably at least in part inhibits the binding of the respective glycoconjugates to the c-type lectin.

Immature DC are highly efficient in antigen capture and processing, whereas mature DC are specialized in the naïve T cell activation necessary for cellular immune responses. Immature DC mature in response to specific 'danger' signals such as bacterial components (LPS) or inflammatory cytokines TNFa, PGE2). In the present invention it was found that a glycoconjugate comprising a mannose, a fucose residue or a derivative, a combination or multimer thereof, does not induce DC maturation. In contrast to LPS that triggers TLR4, no up-regulated expression of the activation markers CD80, CD83, CD86 or HLA-DR was observed. However, when the maturation of immature dendritic cells was studied in the situation when the cells are also activated via a Toll-like receptor pathway, a strong inhibition of Toll-like receptor induced maturation was observed, particularly when the dendritic cells were exposed to ManLAM. Such inhibition thus dampens the response of Toll-like receptor pathway stimulated dendritic cells and thereby the capacity of an individual to cope with pathogens that are combated via activation of the Toll-like receptor pathway. This dampening of DC-activation can be at least in part prevented by at least in part inhibiting binding of particularly a glycoconjugate comprising at least two mannose residues in $\alpha 1,2$ linkage, but also analogously acting glycoconjugates to C-type lectins on the immature dendritic cells. The invention thus provides a method for determining whether a compound is capable of modulating an activation state of a dendritic cell comprising providing said dendritic cell with a compound capable of specifically binding to a C-type lectin and determining whether a Toll-like receptor signaling pathway in said dendritic cell is modulated. Further provided is a method for modulating the activity of a Toll-like receptor signaling pathway in a cell, wherein said cell comprises a Toll-like receptor and a C-type lectin, said method comprising contacting said cell with an isolated and/or recombinant C-type lectin binding molecule. Preferably said C-type binding molecule comprises a glycoconjugate comprising a mannose, a fucose residue or a derivative, a combination or multimer thereof. Activity can be modulated upward by at least in part preventing simultaneous stimulation of C-type lectin with a glycoconjugate comprising at least two mannose residues in $\alpha 1,2$ linkage or analogously acting compound. Activity is modulated downward by simultaneously providing said a glycoconjugate comprising at least two mannose residues in $\alpha 1,2$ linkage or analogously acting compound. Analogously acting compounds comprise the same Toll-like receptor signaling interfering capacity as ManLAM in kind not necessarily in amount. A preferred analogously acting compound comprises a glycoconjugate comprising a fucose residue or a derivative or multimer thereof. A further level of control is possible using C-type lectin binding compounds that at least in part interfere with the binding capacity of a glycoconjugate comprising at least two mannose residues in $\alpha 1,2$ linkage or an analogously acting compound. In this way activity of the Toll-like receptor pathway can be modulated upward (in the presence of the proper Toll-like receptor ligand) even in the presence of a glycoconjugate comprising at least two mannose residues in $\alpha 1,2$ linkage or analogously acting compound. The latter feature is of importance in cases where the immune system has problems combating an infection via the Toll-like receptor pathway, particularly when said infection is accompanied with secretion of a glycoconjugate comprising at least two mannose residues in $\alpha 1,2$ linkage or analogously acting compounds, such as mycobacteria and in particular *M. tuberculosis* and *M. Bovis*. Thus the invention further provides a method for stimulating maturation of a dendritic cell that is contacted with a Toll-like receptor ligand and a glycoconjugate comprising at least two mannose residues in $\alpha 1,2$ linkage or analogously acting compound, said method comprising providing said dendritic cell with a C-type lectin binding molecule capable of blocking the binding of said glycoconjugate to said C-type lectin. C-type lectin binding molecules capable of at least in part inhibiting the binding of a glycoconjugate comprising at least two mannose residues in $\alpha 1,2$ linkage or analogously acting compounds are for instance C-type lectin binding antibody or a functional part, derivative and/or analogue thereof, with a binding specificity that blocks or covers the ManLAM binding site on said C-type lectin. Preferable said C-type lectin comprises DC-SIGN. Thus in a preferred embodiment said antibody is a DC-SIGN specific antibody. A suitable example of such an antibody is AZN-D1, AZN-D2 or AZN-D3 or a human or humanized analogue comprising the same binding specificity in kind not necessarily in amount. In a preferred embodiment the invention provides a method for stimulating maturation of a dendritic cell that is contacted with a Toll-like receptor ligand and a glycoconjugate comprising at least two mannose residues in $\alpha 1,2$ linkage or analogously acting compound, said method comprising providing said dendritic cell with a ligand binding molecule of the invention, thereby at least in part preventing binding of said a glycoconjugate comprising at least two mannose residues in $\alpha 1,2$ linkage or analogously acting compound to the dendritic cell.

An important aspect of the invention is concerned with the use of a glycoconjugate comprising at least two mannose residues in $\alpha 1,2$ linkage or a glycoconjugate comprising a fucose residue or a glycoconjugate comprising at least one end standing N-acetylglucosamine or a derivative or multimer thereof, a ligand binding molecule of the invention and/or a C-type lectin binding molecule of the invention for the preparation of a medicament. Such medicaments may be used for the treatment of an immune system associated disease or the treatment of an acquired disease. Preferably, said acquired disease comprises an infection with human immunodeficiency virus, a *helicobacter*, a *neisseria meningitidis*, a *leishmcnia*, a *schistosoma*, a *klebsiella*, a probiotic *lactobacillus*, hepatitis C virus, a herpes simplex virus or an ebola virus.

Considering the natural role of C-type lectins on antigen presenting cells it is within the scope of the present invention to stimulate immune responses in an individual by providing antigen through a C-type lectin receptor on the antigen presenting cell. This can of course be achieved when the antigen comprises a glycoconjugate comprising at least two mannose residues in α1,2 linkage or glycoconjugate comprising a fucose residue or a glycoconjugate comprising at least one end standing N-acetylglucosamine or derivative or multimer thereof In this embodiment it is preferred that simultaneous activation of the Toll-like receptor signaling pathway is at least in part prevented. Provided is thus a glycoconjugate comprising an antigen and a glycoconjugate comprising at least two mannose residues in α1,2 linkage and/or a fucose residue and/or at least one end standing N-acetylglucosamine or a derivative or multimer thereof for use for the preparation of a vaccine. The vaccine may be preventive or curative. The antigen may be derived from any source as long as it is capable of being presented through major histocompatibility complex I, complex II or C1b. In a preferred embodiment said antigen comprises a tumor antigen. The presence of the mentioned carbohydrates on tumor cells facilitates antigen capture by DC to enhance antigen presentation and as a result immune activation. On the other hand, the immune response against tumor antigen lacking the mentioned carbohydrates can stimulated significantly by providing the antigen with one or more of the mentioned carbohydrates thereby stimulating DC uptake and thus the immune response against the antigen. This aspect is useful in the preparation of vaccines.

DC-SIGN has been demonstrated to have a carbohydrate specificity for mannose-containing carbohydrates, Lewis antigens and GlcNAc-containing structures (FIGS. 33, 34, 63-66). We have demonstrated that the carbohydrate specificity of L-SIGN is different since it does not recognize Lewis antigen carbohydrate structures whereas it does recognize high mannose structures (FIGS. 33 and 34). The murine homologue mSIGNR1 recognizes similar to DC-SIGN high mannose and Lewis antigens, but has also specificity for sialylated Lewis antigens in contrast to DC-SIGN and L-SIGN (FIGS. 33 and 34).

DC-SIGN is a C-type lectin in particular highly expressed on Dendritic cells. Its function is to recognize antigen and process and present this very efficiently into MHC class I and II molecules.

It has long been thought that DC-SIGN is a pathogen recognition receptor that recognizes pathogens to activate the immune system, but as it seems now, the long list of pathogens that target DC-SIGN all persist and escape immunity by different mechanisms. We have now four examples of pathogens that target DC-SIGN to survive in the host.
1. HIV-1 and HCV target DC-SIGN to 'hide' within DC and escape the intracellular routing to the lysosomal compartment.
2. Secretion of ManLam by mycobacteria targets DC-SIGN to induce downmodulation of TLR induced DC maturation, and induction of IL-10.
3. the human gastric pathogen *Helicobacter pylori* persists: Lipopolysaccharide phase variants modulate the Th1/Th2 balance through interaction with the dendritic cell lectin DC-SIGN.
4. *Lactobacillus* target DC-SIGN on DC and induce regulatory T cells, inhibition of recognition of *Lactobacillus* by DC-SIGN reduces the regulatory state of T cells.

DC-SIGN is thus a receptor that 'normally' recognize self-antigen to tolerize (Annual Review Immunology, 2004). We here demonstrate that targeting of DC-SIGN by lactobacilli can indeed induce regulatory T cells. Furthermore it seems that DC-SIGN can also recognize the tumor antigen CEA (CD66e) in particular Lewis X and Y. These tumor antigens can be secreted and suppress DC activation in a similar way as ManLam of mycobacteria tuberculosis. The interaction of DC with granulocytes is elucidated by the fact that DC-SIGN recognizes CD66a and CD11b on granulocytes. In particular Lewis X antigen on these molecules is recognized. In that way DC-SIGN functions as a cell adhesion receptor that mediates cellular interactions of granulocytes with DC. This cellular adhesive function between granulocytes and dendritic cells has never been reported but it is likely that the granulocyte DC interaction is essential to form a bridge between the innate immune response and the adaptive immune response in such a way that the granulocyte passes the infectious agents to the DC mounting an adequate immune response. In particular the granulocyte activates and matures the DC, inducing upregulation of cytokines and costimulatory molecules which is necessary for DC migration and initiation of the adaptive immune response. The interaction of DC with granulocytes is also seen in vivo in the situation of Crohns disease. A new pathogen that interacts with DC-SIGN on DC is *Neisseria Meningitidis*. Strain variants demonstrate that in particular one strain mutant IgtB interacts which contains endstending GlcNAc residue. Other experiments (FIG. 66) demonstrate the DC-SIGN also recognizes GlcNac.

In another embodiment the invention provides the use of ligand binding molecule and/or a c-type lectin binding molecule of the invention for the preparation of a vaccine. A dampening of the immune system due to the effect of a glycoconjugate comprising at least two mannose residues in α1,2 linkage or analogously acting compounds is reduced by providing a glycoconjugate or antibody capable of at least in part inhibiting the binding of a glycoconjugate comprising at least two mannose residues in α1,2 linkage or analogously acting compound to their C-type lectin receptor. The antibody preferably comprises SMLDN1.1, SMFG4.1, 6H3 or SMLDN1.1. Thus antigen present in said vaccine or provided separately is more effective in stimulating or boosting an immune response in the presence of a glycoconjugate comprising at least two mannose residues in α1,2 linkage or analogously acting compound. This is particularly important in patients suffering from a mycobacterial infection, such as but not limited to *M. tuberculosis* or *M. bovis*. Preferably, said vaccine is used to stimulate an antigen specific immune response in said individual. In a preferred embodiment the medicament or vaccine is used for the treatment of an individual suffering from a cancer, an autoimmune disease or a transplantation related disease.

As used herein the term "antibody" refers to antibodies derived from humans or other animals. The antibody is preferably produced outside the body. The antibody can also be generated or selected using artificial systems such as phage display selection. An antibody having no natural counterpart is therefore well within the scope of the present invention. Antibodies as used herein also include fragments thereof capable of binding to the same target, such as FAB fragments or even smaller parts. The antigen binding part of an antibody of the invention may also be grafted onto another type of molecule to provide that molecule with a binding specificity as provided for in the invention. Modification of the antibody to include human or humanized versions thereof with the same binding specificity in kind not necessarily in amount are of course also in the scope of the invention. Also included are single chain fragments and variants thereof.

As used herein the term proteinaceous molecule refers to a peptide, a poly-peptide, protein and the like with or without modifications. Such modifications may be synthetic and/or provided for by a biological system. The latter including for instance post-translation modification such as glycosylation.

Where the invention is described for use in humans, the invention is also functional in other animals for instance farm-animals and pets. These medical and vaccine uses and methods of treatment are therefore also part of the invention.

BRIEF DESCRIPTION OF THE DRAWINGS

FIG. 1. $Le^x$-neoglycoconjugates bind with high affinity to DC-SIGN.
a. Schematic diagram of the covalent structures of the glycan chains of synthetic glycoconjugates used in the DC-SIGN binding assay. b and c. Glycoconjugates were coated and binding of recombinant DC-SIGN-Fc was measured after incubation with peroxidase-labeled goat-anti-human Fc. Anti-DC-SIGN monoclonal antibody AZN-D1 were used to block binding. c. Titration of the glycoconjugates revealed that DC-SIGN binds with high affinity to $Le^x$, $Le^y$, $Le^a$, $Le^b$, or LDNF-glycoconjugates and □1,3,□□1,6 mannotriose, sulfo-Lea, whereas it has a lower binding affinity for □-mannose and □-L-fucose, and sialyl-$Le^x$.

Figure 2:
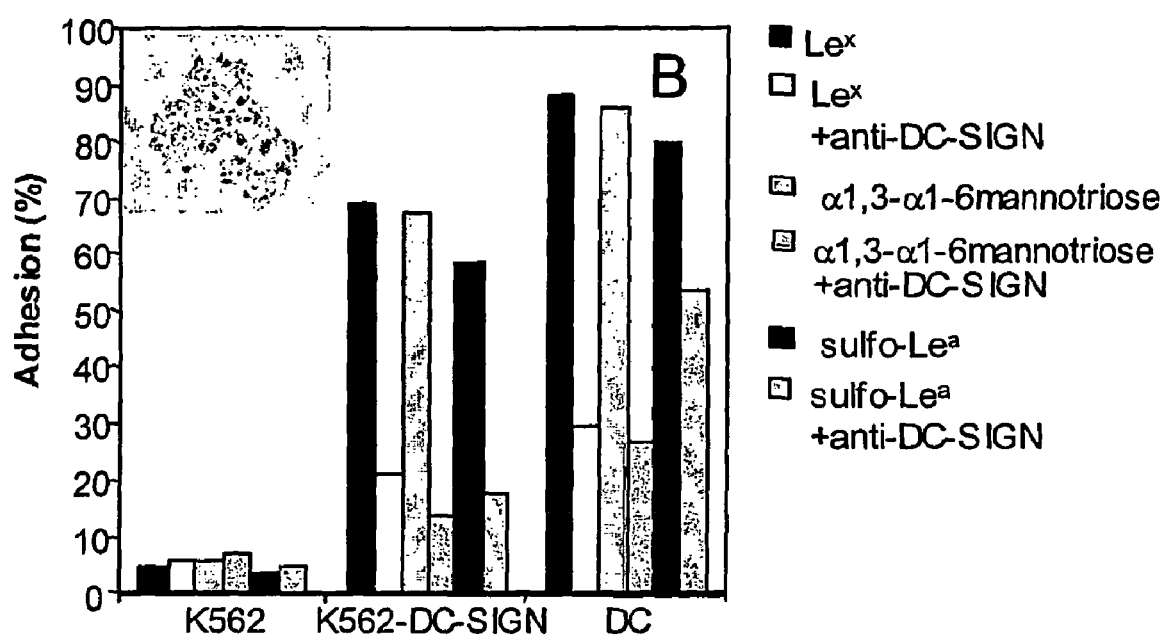
FIG. 2. Cellular DC-SIGN displays a binding specificity similar to that of soluble DC-SIGN-Fc. Binding of DC-SIGN expressing K562 transfectants and immature monocyte derived DC to glycoconjugate-coated fluorescent beads was measured by FACscan analysis. Binding was inhibited by anti-DC-SIGN monoclonal antibody AZN-D2. One representative experiments out of three is shown. SD is less than 2%. Inlay: Picture of $Le^x$-coupled fluorescent beads that bind to DC-SIGN expressing DC.

Open histograms represent isotype control and filled histograms indicate specific antibody staining.

b) Immature DC bind strongly to ManLAM via DC-SIGN. Binding was determined using the fluorescent bead adhesion assay. Specificity was determined by measuring binding in the presence of mannan, EGTA or blocking antibodies against DC-SIGN (AZN-D2), MR (Clone 19), CD11b (bear-1) or CD11c (SHCL3). Standard deviation<5%. One representative experiment out of three is shown.

c) DC-SIGN mediates capture of *M. bovis* BCG by immature DC. Binding was determined by flow cytometry using FITC-conjugated mycobacteria. Specificity was determined by measuring binding in the presence of antibodies against DC-SIGN (AZN-D1, AZN-D2 and AZN-D3), MR (Clone 19), CD11b (bear-1) and CD11c (SHCL3). Binding was also measured in the presence of the C-type lectin inhibitors mannan and EGTA, whereas a known MR ligand, mannose-BSA, was used to determine the contribution of the MR receptor. Standard deviation<2%. One representative experiment out of three is shown.

d) DC-SIGN mediates capture and internalization of *M. bovis* BCG by K562 cells. K562 transfectants were incubated with FITC-conjugated *M. bovis* BCG (MOI 20). Cells were washed, and surface FITC was quenched by exposure to trypan blue. Phagocytosis was determined by comparing the FITC labeling before and after quenching using flow cytometry. Surface bound bacteria are represented by open bars, internalized by closed bars. Standard deviation<4%. One representative experiment out of three is shown.

e) Immature DC rapidly phagocytose mycobacteria through DC-SIGN. The internalization was determined as described in FIG. 3b. Surface bound bacteria are represented by open bars, internalized by closed bars. Standard deviation<5%. One representative experiment-out of three is shown.

FIG. 9. DC-SIGN mediates internalization of captured mycobacteria and ManLAM.

a) *M. bovis* BCG and ManLAM are internalized by DC-SIGN on immature DC and targeted to the lysosomes. The fate of captured mycobacteria was followed by analyzing immature DC pulsed with FITC-conjugated *M. bovis* BCG (MOI 20) for 2 hours using immuno-fluorescence microscopy (magnification 200×). ManLAM was followed by incubating DC with ManLAM (10 mg/ml) for 1 hour. DC-SIGN, ManLAM and CD207a/Lamp-1 were stained with AZN-D1, F30.5 and H4A3, respectively. One representative experiment out of three is shown.

b) ManLAM induces down-regulation of DC-SIGN, but not of MR, CD11b and CD11c. Immature DC were incubated with 15 mg/ml of ManLAM or AraLAM for 18 hours, and then DC-SIGN expression was determined by flow cytometry. One representative experiment out of three is shown.

Figure 5:
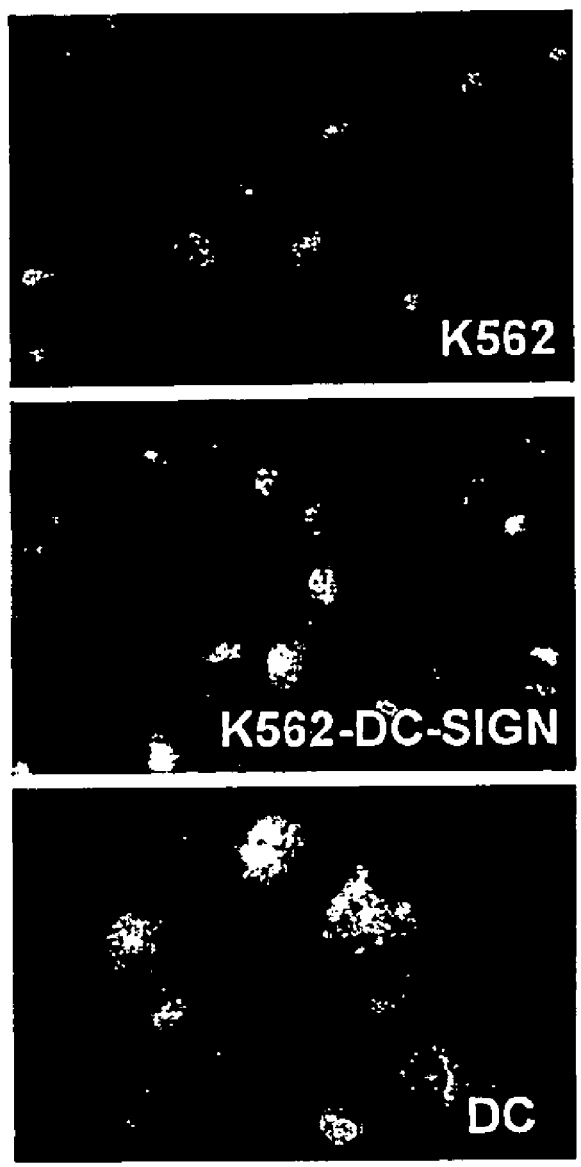
FIG. 5. DC-SIGN rapidly internalizes $Le^x$ glycans to lysosomal compartments. Synthetic biotinylated $Le^x$-PAA were added to DC-SIGN-expressing K562 cells or immature monocyte derived DC for 30 min incubation at 37° C. Cells were stained with anti-CD107a (LAMP-1, green) as a lysosomal marker and avidine-Alexa 594 for localization of $Le^x$ after permeabilization of the cells. Co-localization of LAMP-1 and $Le^x$ results in a yellow staining.

FIG. 10. Mycobacteria induce IL-10 production by DC through ManLAM and direct infection.

a) ManLAM induces IL-10 production of LPS-matured DC. Immature DC were incubated with 15 mg/ml of either ManLAM or AraLAM in the presence of LPS (10 ng/ml). The specificity was determined in the presence of blocking antibodies against DC-SIGN (AZN-D2; 20 µg/ml). Supernatants were harvested after 18 hours and the IL-10 production was measured by ELISA Values are the means±standard deviations of triplicate determinations. One representative experiment out of three is shown.

b) *M. bovis* BCG infection of immature DC induces I-L10 production. Immature DC were infected with *M. bovis* BCG (MOI 4), and the experiment was performed as described in FIG. 5a. Values are the means±standard deviations of triplicate determinations. One representative experiment out of three is shown.

Figure 11:
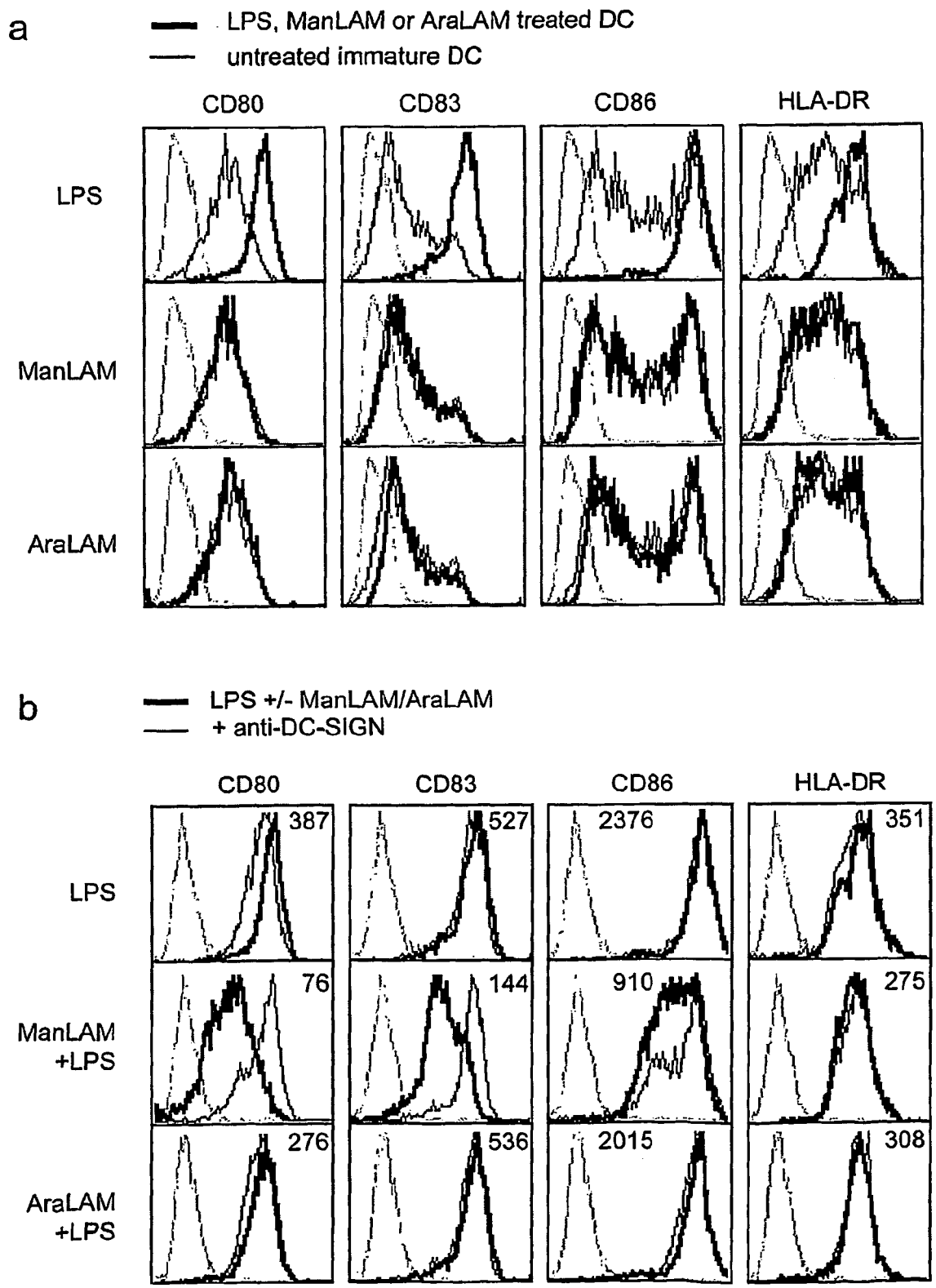

FIG. 11. ManLAM inhibits LPS-induced DC activation through DC-SIGN binding.

a) ManLAM does not induce activation of immature DC. Immature DC were incubated with ManLAM, AraLAM or LPS for 18 hours, and activation was determined by measuring the expression of CD80, CD86, CD83 and HLA-DR. Dotted lines represent isotype controls, the thin lines indicate expression levels of immature DC, and the thick line represents immature DC that have been treated with either LPS (10 ng/ml), ManLAM (15 µg/ml) or AraLAM (15 µg/ml). One representative experiment out of three is shown.

b) LPS-induced activation of DC is blocked by ManLAM. Immature DC were co-cultured with LPS alone, or together with either ManLAM or AraLAM for 18 hours. Dotted lines represent isotype controls. Thick lines, and the mean fluorescence values in the histograms, represent the expression levels after treatment with LPS alone, or in combination with either ManLAM or AraLAM. Thin lines indicate the presence of antibodies against DC-SIGN throughout the incubation. One representative experiment out of three is shown.

Figure 12:
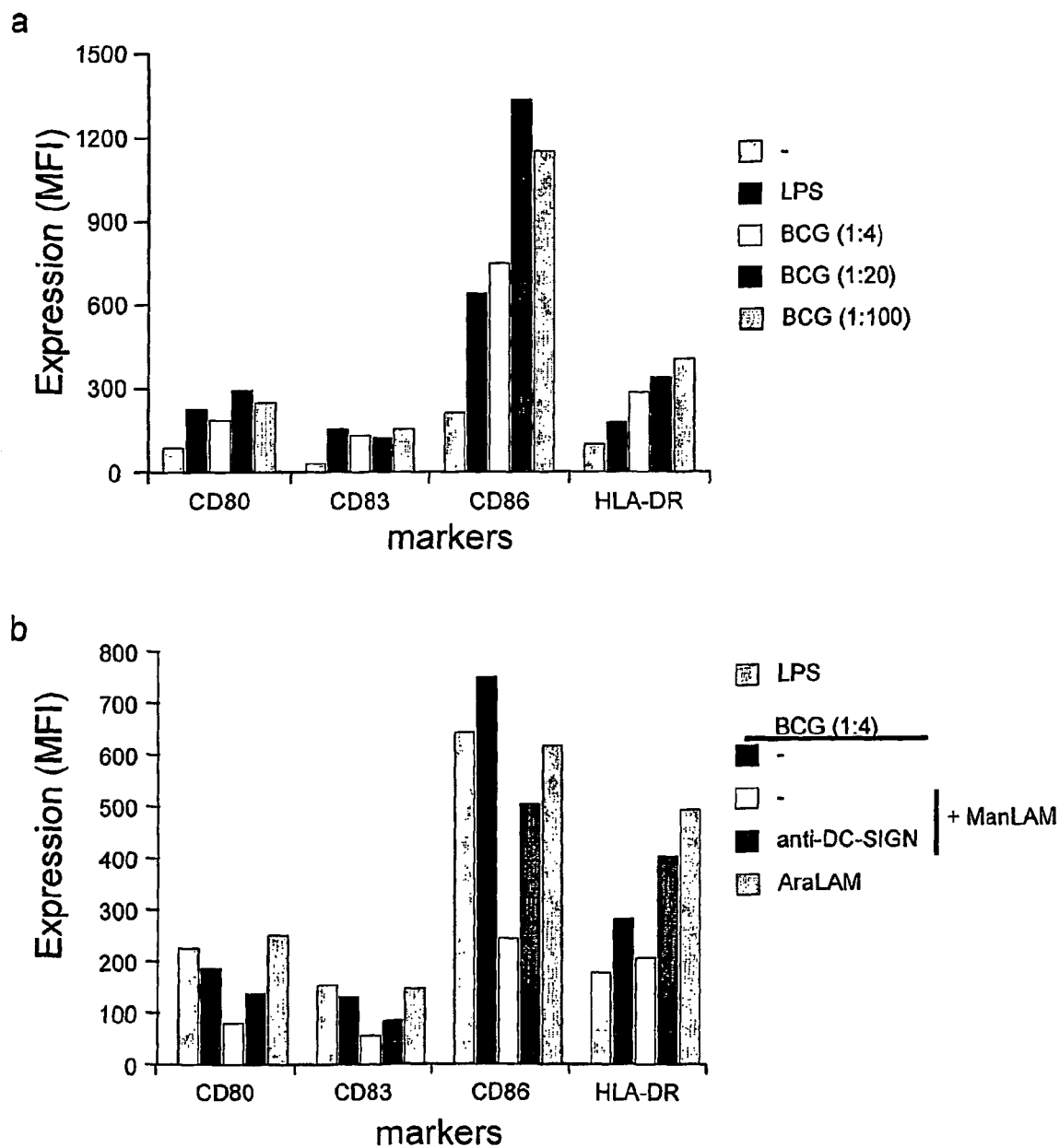

FIG. 12. *M. bovis* BCG induces maturation and ManLAM inhibits the induced DC activation through DC-SIGN binding.

a) *M. bovis* BCG induces maturation of immature DC. Immature DC were incubated with LPS or viable *M. bovis* BCG (MOI 4, 20 and 100) for 18 hours, and activation was determined by measuring the expression of CD80, CD86, CD83 and HLA-DR. The mean fluorescence intensity is depicted. One representative experiment out of three is shown.

b) *M. bovis* BCG-induced activation of DC is blocked by ManLAM. Immature DC were infected with *M. bovis* BCG (MOI 4). Cells were pre-incubated with 15 µg/ml of either ManLAM or AraLAM and the expression of the markers was measured after 18 hours as described in FIG. 7a. Specificity was determined by pre-incubating cells with blocking antibodies against DC-SIGN (AZN-D2; 20 µg/ml). One representative experiment out of three is shown.

Figure 13:
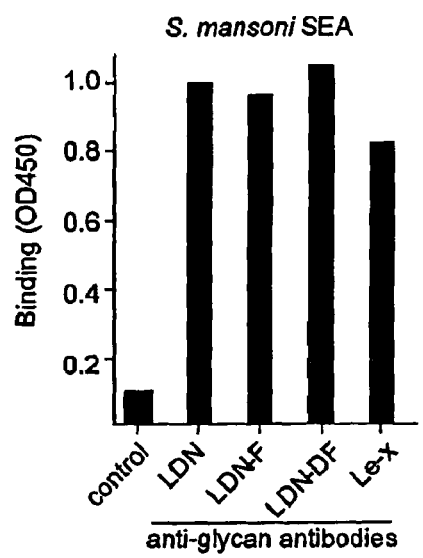

FIG. 13. Structures of *S. mansoni* SEA carbohydrate antigens, monoclonal antibodies (Mabs) recognizing them, and reactivity of these Mabs with SEA. The reactivity of the MAbs was measured by ELISA, using SEA coated at a concentration of 1 µg/ml. The antibodies, incubated at a concentration of 1 µg/ml all showed a strong reaction with SEA.

Figure 14:
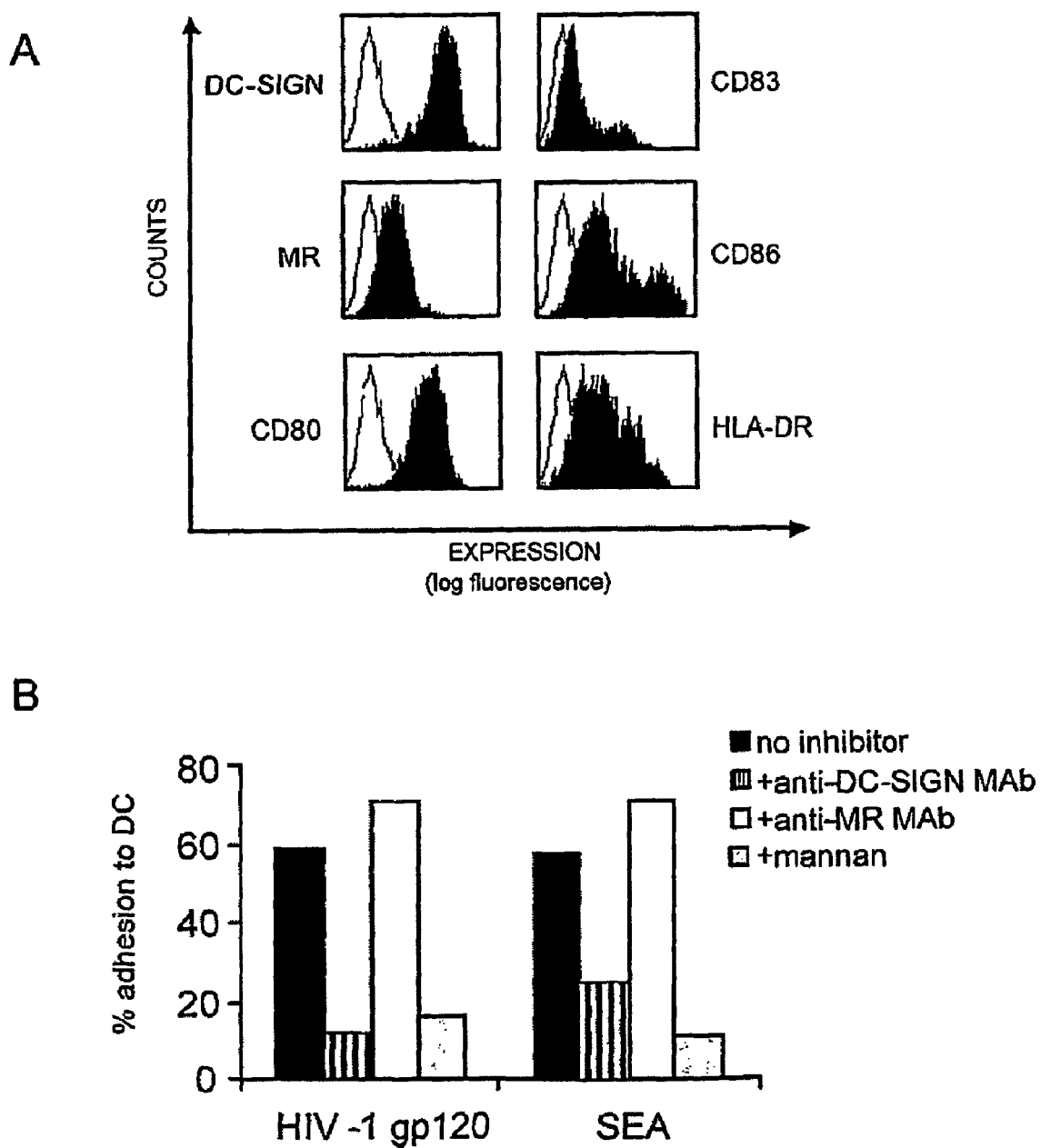

FIG. 14. Interaction of SEA with immature human DC.

a) Immature human DC were cultured from monocytes in the presence of GM-CSF and IL-4. The DC express next to high levels of DC-SIGN, the MR, CD83, CD86, CD80 and HLA-DR as determined by FACSscan analysis b) DC-SIGN, expressed by immature DC, shows a similar binding to SEA as to HIV-1 gp120, a previously defined ligand of DC-SIGN. The adhesion to both SEA and HIV-1 gp120 was determined using the fluorescent bead adhesion assay. Mannan and anti-DC-SIGN MAb AZN-D1 (20 µg/ml), but not anti-MR MAb clone 19, block adhesion of SEA to the DC. One representative experiment out of three is shown, using anti-LDN antibodies to couple SEA to the fluorescent beads. Similar results are obtained using anti-LDN-DF antibodies (not shown).

Figure 15:
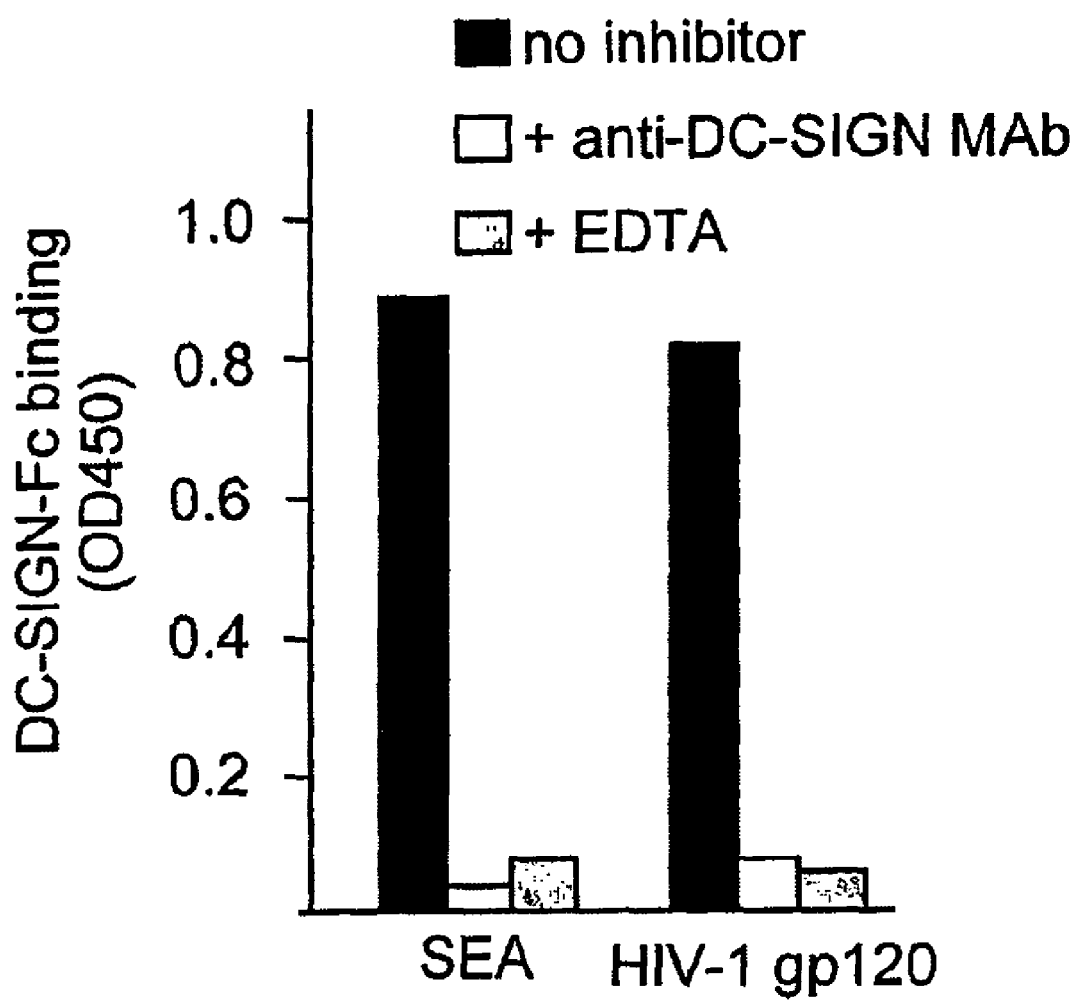

FIG. 15. Binding of DC-SIGN to S. mansoni SEA.

DC-SIGN binds as strongly to SEA as to HIV-1 gp120, as was determined by an ELISA based assay using soluble DC- SIGN-Fc. SEA were coated at a concentration of 5 µg/ml, and HIV-1 gp120 at a concentration of 1 µg/ml. Specificity was determined by measuring binding in the presence of the anti-DC-SIGN blocking antibody AZN-D1 (20 µg/ml), or EDTA (5 mM).

Figure 16:
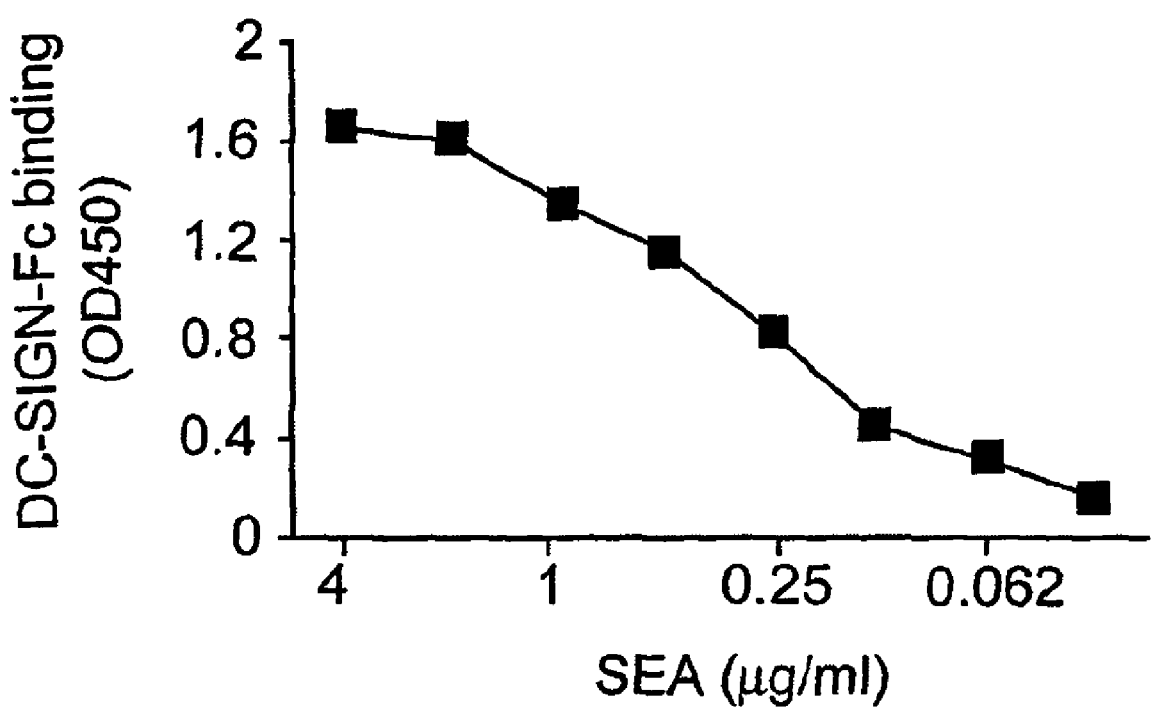

FIG. 16. DC-SIGN strongly binds SEA

Binding of soluble DC-SIGN-Fc to different concentrations SEA was measured by an anti-IgG-Fc ELISA.

Figure 17:
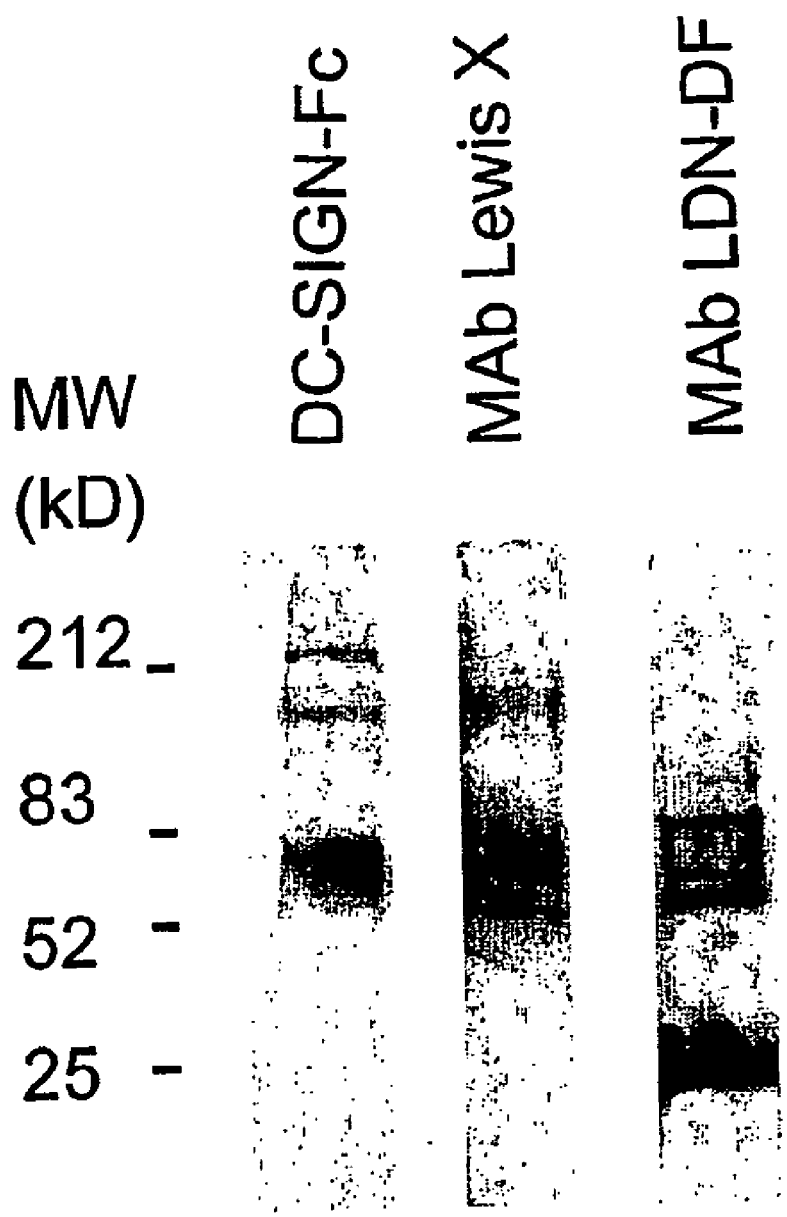

FIG. 17. DC-SIGN binds a subfraction of SEA

SEA were separated by SDS-PAGE gelelectrophoresis on a 12.5% polyacrylamide gel.
a) polyacrylamide gel with SEA (15 µg) silver-stained to detect all proteins
b) Western blot of polyacrylamide gel after SDS-PAGE of SEA (2 µg), using soluble DC-SIGN-Fc to detect DC-SIGN binding glycoproteins.

FIG. 18. DC-SIGN binds to fucosylated SEA and the α1,3-fucosylated trisaccharide $Le^x$
a) SEA were defucosylated by mild acid treatment or α3,4-fucosidase. Binding of soluble DC-SIGN-Fc to defucosylated SEA (coated at 1 µg/ml) was measured by an anti-IgG-Fc ELISA. The degree of defucosylation, and the integrity of non-fucosylated glycans after the treatments was established using different anti-glycan MAbs, and goat-anti-mouse IgM-peroxidase for detection.
b) Competitive inhibition of the binding of soluble DC-SIGNFc to SEA and HIV gp120 by anti-glycan mAbs in ELISA. Coated antigens were preincubated with anti-glycan mAbs before adding DC-SIGNFc. Binding of DC-SIGN Fc was measured by an anti-IgGFc ELISA. Antibodies used preferably SMLDN1.1 or SMFG4.1 (anti-$Le^x$) or SMLDN1.1 (anti-LDNF) or anti-DC-SIGN (AZN-D1, D2, AZN-D3),
c) DC-SIGN strongly binds to neoglycoproteins carrying α1,3-fucosylated oligosaccharides $Le^x$ and LDN-F but poorly to neoglycoconjugates carrying a single a-linked fucose or to LDN-DF. Neoglycoproteins were coated at a concentration of 5 µg/ml. No binding was observed to neoglycoproteins carrying Galb1,4GlcNAc or GalNAcb1,4GlcNAc (LDN) (not shown).

Figure 19:
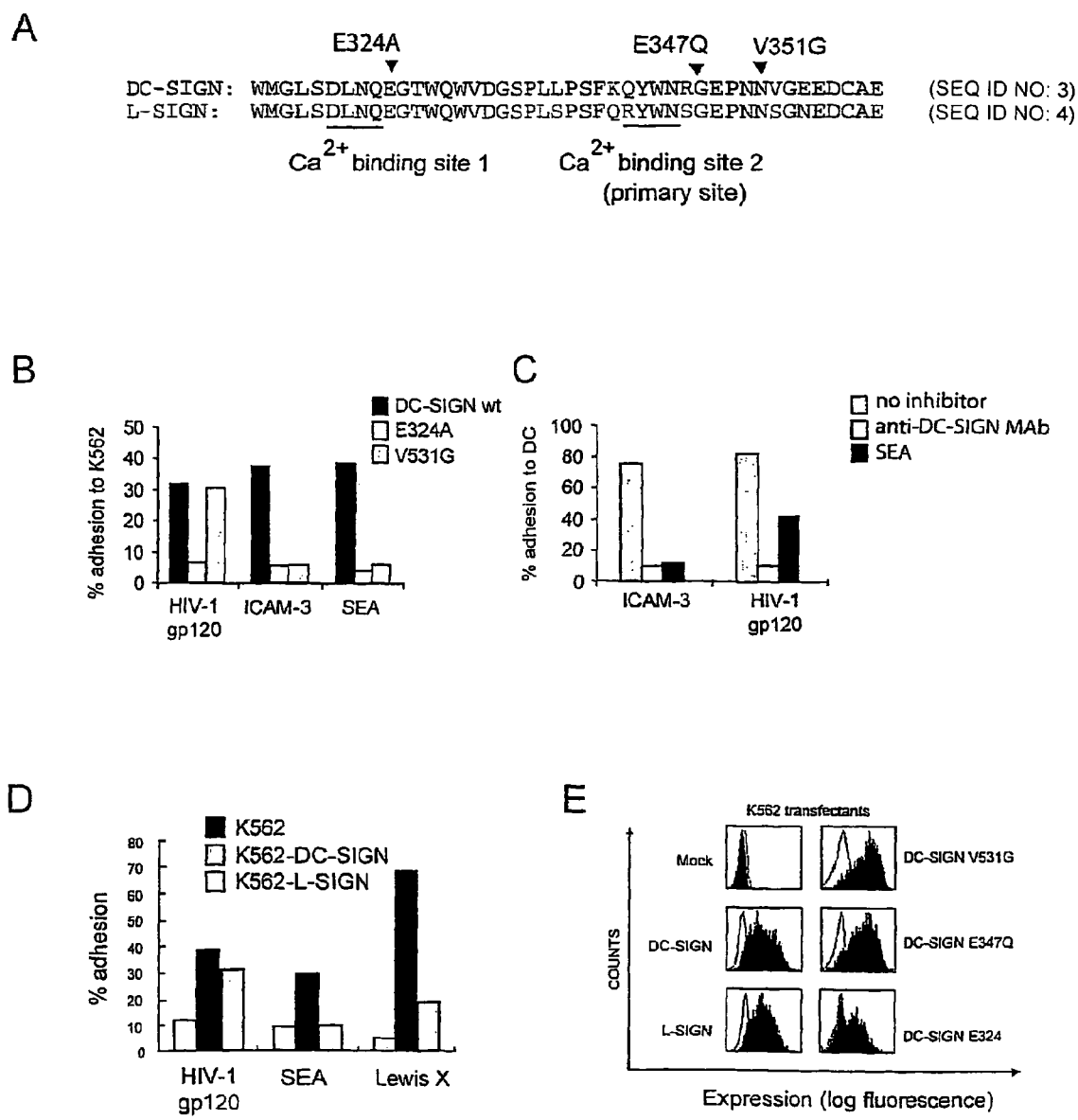

FIG. 19. Binding of SEA and $Le^x$ to mutant DC-SIGN and L-SIGN
a) Amino acid sequence alignment of part of the CRDs of DC-SIGN (AAK20997) with that of the highly homologous C-type lectin L-SIGN (AAK20998). The position of the E324A, E347Q and V351G mutations in DC-SIGN are indicated by an arrow.
b) Binding of SEA and $Le^x$-PAA coated beads to K562 transfectants expressing wild-type DC-SIGN and the E324A, E347Q and V351G DC-SIGN mutants, was measured using the fluorescent bead adhesion assay. To detect SEA, fluorescent beads coupled to the LDN-DF MAb were used. One representative experiment out of two is shown.
c) SEA blocks binding of DC-SIGN, expressed by human immature DC, to ICAM-3 and HIV-1-gp120. In contrast, RNAseB does not block this binding. The adhesion of both ICAM-3 and HIV-1 gp120 to DC was determined using the fluorescent bead adhesion assay. Inhibitors were present at a concentration of 20 µg/ml.
d) DC-SIGN, expressed by K562 transfectants, binds strongly to both SEA and HIV-1 gp120, whereas L-SIGN, expressed by K562 transfectants only recognizes HIV-1 gp120. The adhesion was determined using the fluorescent beads adhesion assay. To detect SEA, both anti-LDN and anti-LDN-DF coated fluorescent beads were used with similar results. One representative experiment out of two is shown, using anti-LDN-DF fluorescent beads.
e) K562 transfectants efficiently express DC-SIGN, L-SIGN and the different mutant DC-SIGNs, as determined by FACSscan analysis FIG. 20. Granulocytes strongly interact with DC-SIGN-coated beads, partly through $Le^x$-containing ligands.
A. Both mannose as well as Lewis-X epitopes are highly expressed on glycans expressed by granulocytes
B. DC-SIGN binds strongly to freshly isolated granulocytes. Freshly isolated granulocytes are incubated with DC-SIGN-Fc-coated fluorescent beads. The adhesion is determined by the fluorescent bead adhesion assay. Specificity is determined by measuring the adhesion in the presence of mannan, EGTA and antibodies against DC-SIGN (AZN-D1, D2 or D3), b2 integrins (NKI-L19) and $Le^x$ (6H3)

FIG. 21. DC-SIGN-Fc has a high affinity for granulocytes. The interaction of DC-SIGN with granulocytes is further investigated by titration of DC-SIGN-FC and determining the binding by measuring the bound DC-SIGN-Fc using FITC-conjugated Goat-anti-human Fc antibodies. The interaction is blocked by antibodies against DC-SIGN (AZN-D1), and mannan and EGTA (A) and by anti-$Le^x$ antibodies (3H3, B).

Figure 22A:
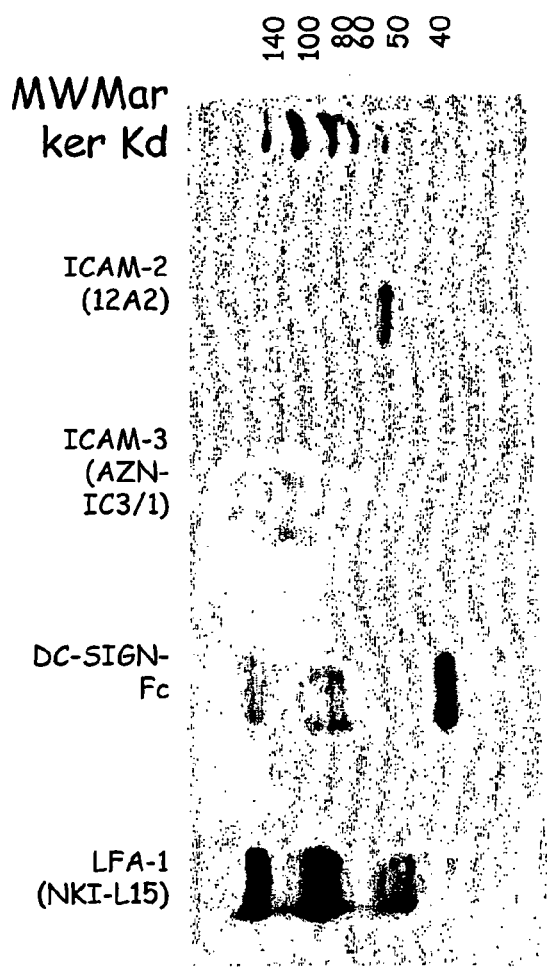
Figure 22B:
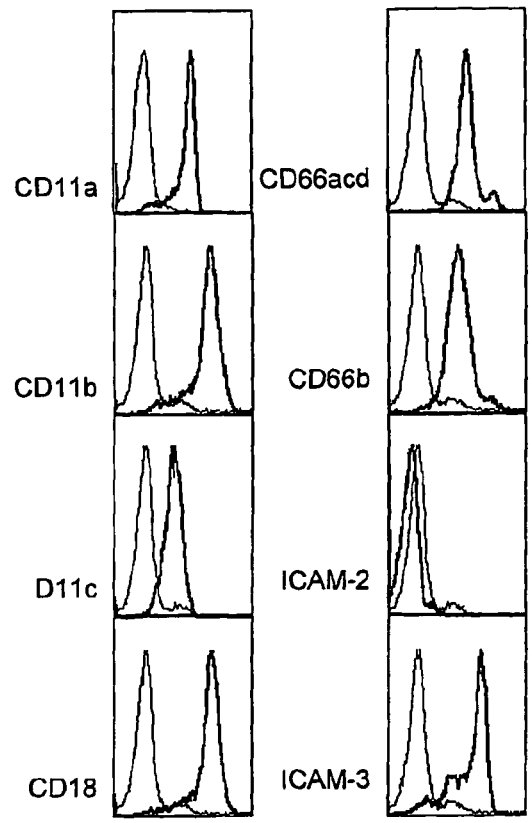
Figure 22C:
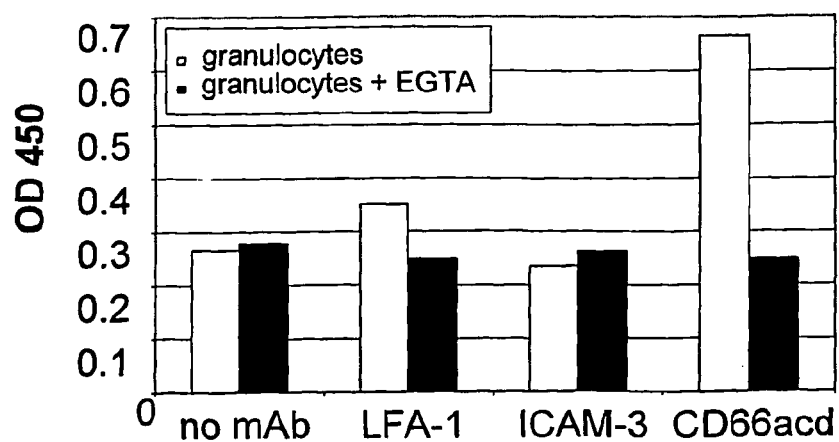

FIG. 22. A 66 kDa protein (CD66) is the high affinity ligand of DC-SIGN on granulocytes.
A. Granulocytes are surface labelled with biotine. The cell lysate is incubated over night at 4° C. with Protein A beads coated with DC-SIGN-Fc or control antibodies against ICAM-2, ICAM-3 and LFA-1. The beads are washed and the immuno-precipitated product is analysed on SDS-PAGE and visualised by autoradiograph. In particular a protein size 66 kD is immuno-precipitated. B. Granulocytes highly express the $Le^x$ containing CD66acd and CD66d antigen, do not express the DC-SIGN ligand ICAM-2 and express ICAM-3. C. Immuno-precipitation of CD66acd demonstrates strong binding activity for DC-SIGNFc. Anti-CD66acd mAbs coated on an ELISA plate were incubated with a lysate of granulocytes. After washing off non-specific proteins DC-SIGNFc was incubated to demonstrate high affinity ligands. DC-SIGNFc does not recognize ICAM-3 from granulocytes demonstrating that on granulocytes not ICAM-3 but CD66acd is the high affinity ligand for DC-SIGN. Binding of CD66acd to DC-SIGNFc is completely inhibited by removal of cations by EDTA.

Figure 23:
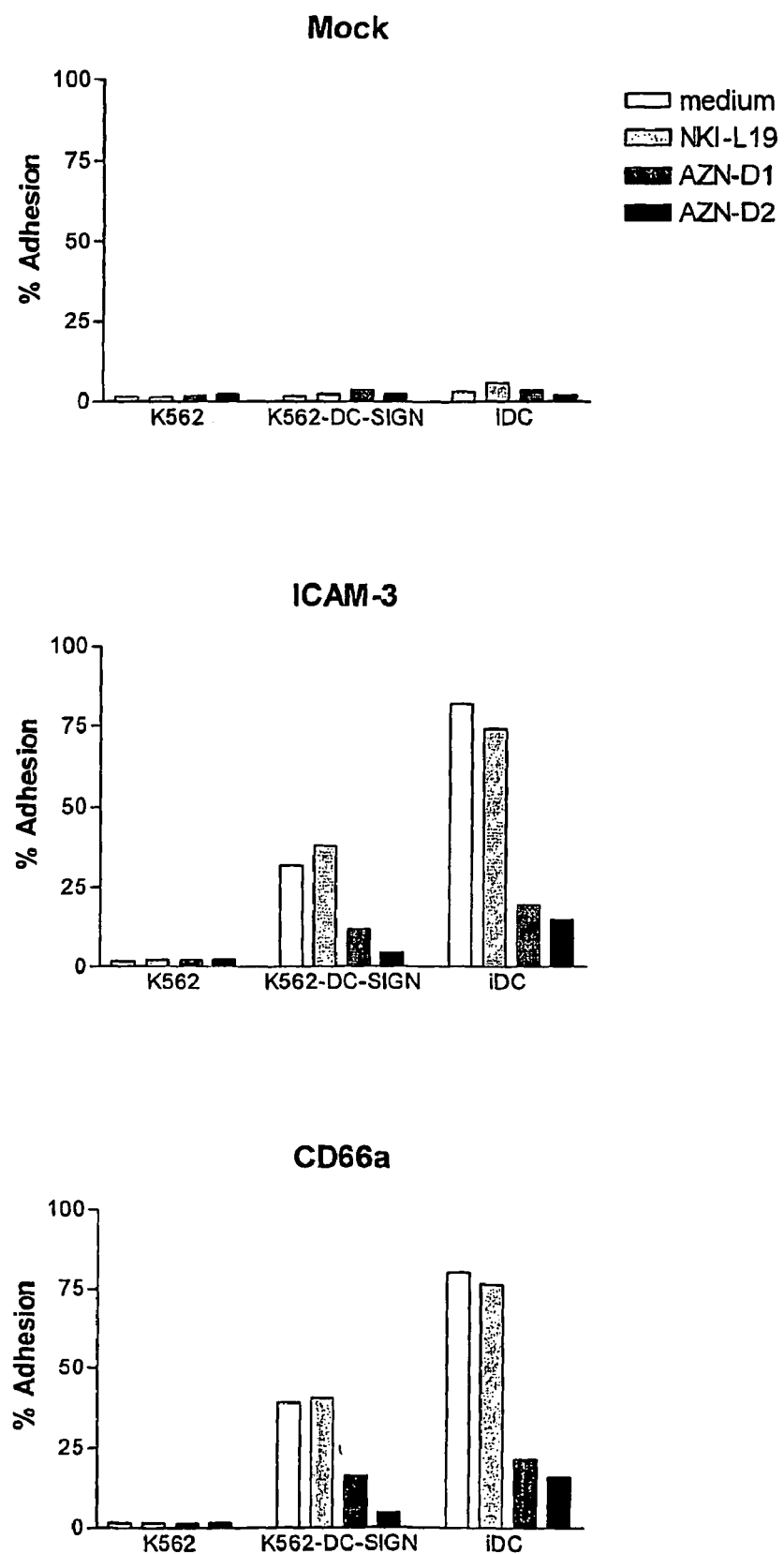

FIG. 23. Cellular DC-SIGN strongly binds to the granulocyte-specific protein CD66a.

293T cells are transfected with pIG-CD66a-Fc, pIG-ICAM-3-Fc and pIG (mock). Supernatants are harvested and beads are coated with the Fc chimeras (CD66a-Fc, ICAM-3-Fc and mock). Immature DC and DC-SIGN-transfected K562 cells are incubated with beads and the adhesion is determined in the presence of antibodies against DC-SIGN and β2 integrins, and mannan and EGTA.

Figure 24:
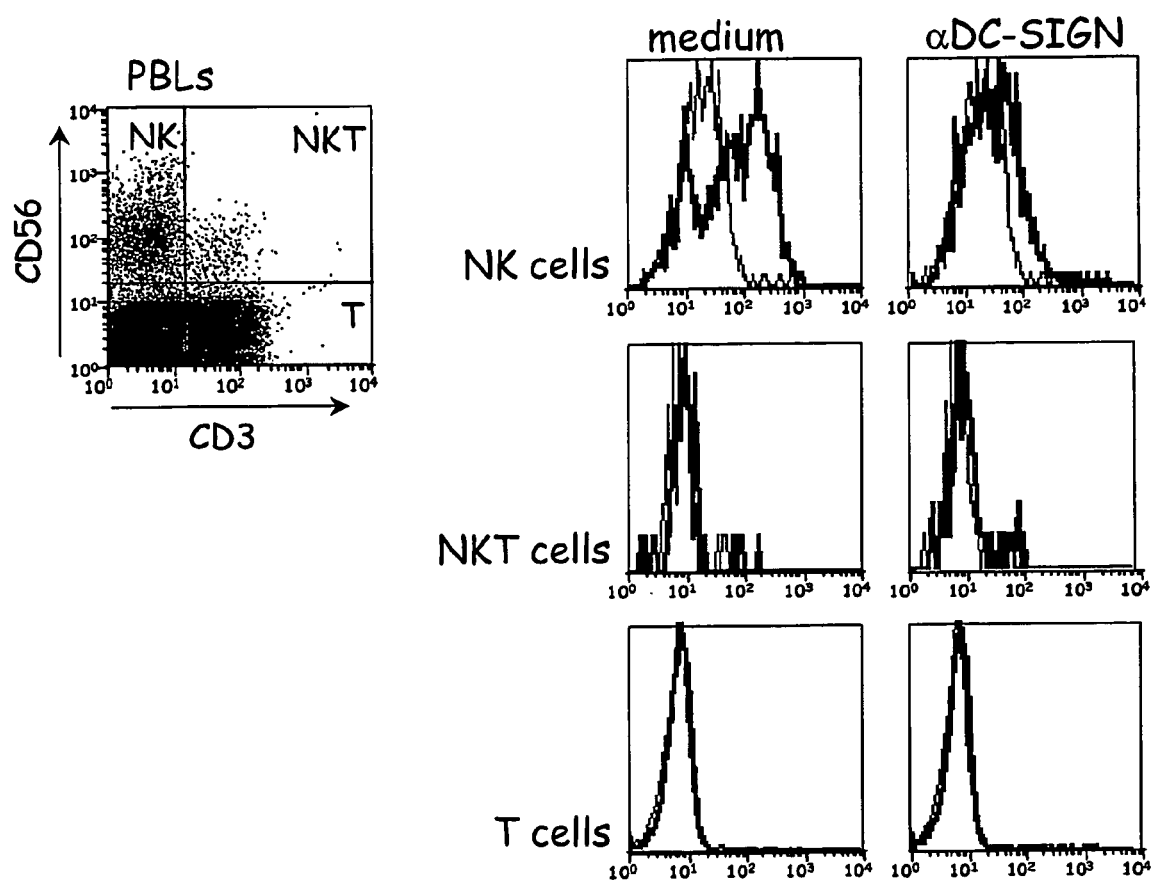

FIG. 24. NK cells specifically interact with DC-SIGN-Fc. The binding of DC-SIGN-Fc to peripheral blood lymphocyte (PBL) subsets is determined by flow cytometry in the presence of antibodies against DC-SIGN. PBL subsets are distinguished by staining with CD3 and CD56, and adhesion is determined by triple staining with DC-SIGN-Fc.

Figure 25:
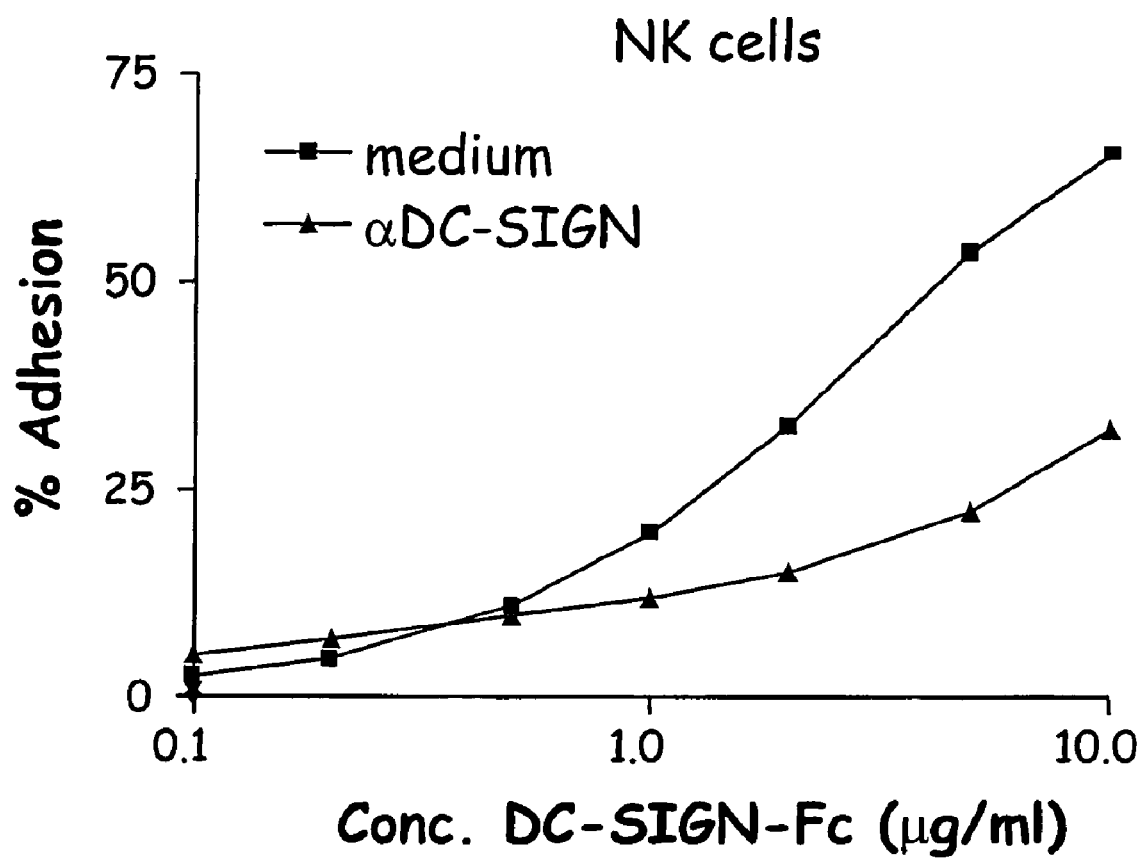

FIG. 25. NK cells specifically interact with DC-SIGN-Fc in a concentration-dependent manner. The binding of DC-SIGN-Fc to peripheral blood lymphocyte (PBL) subsets is determined by flow cytometry in the presence of antibodies against DC-SIGN. NK cells are detected by triple staining with CD3, CD56 and DC-SIGN-Fc. The CD56 dim and bright cells do not differ in ICAM-2 or ICAM-3 expression demonstrating that differential glycosylation is the result of the high affinity binding of DC-SIGNFc to CD56 dim NK cells.

Figure 26:
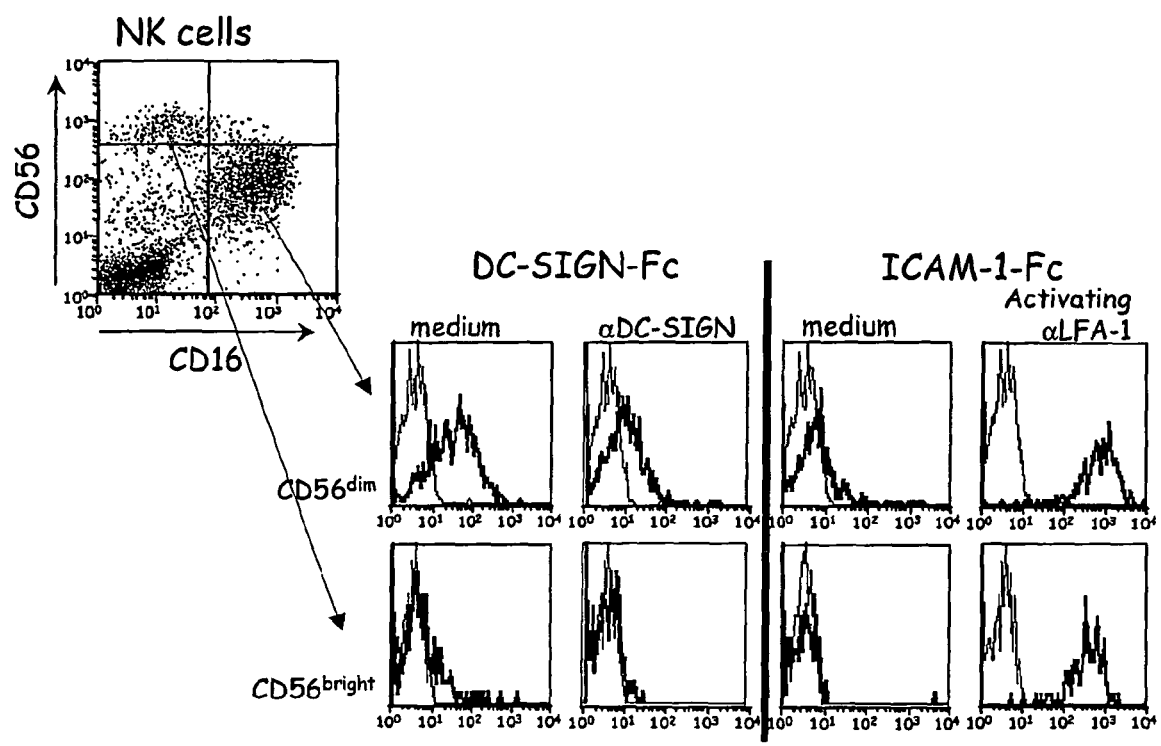

FIG. 26. CD56$^{dim}$CD16$^+$ NK subset specifically interacts with DC-SIGN-Fc.

The binding of DC-SIGN-Fe to NK subsets is determined by flow cytometry in the presence of antibodies against DC-SIGN. NK subsets are distinguished by staining with CD16 and CD56, and the adhesion is determined by triple staining with DC-SIGN-Fc.

Figure 27:
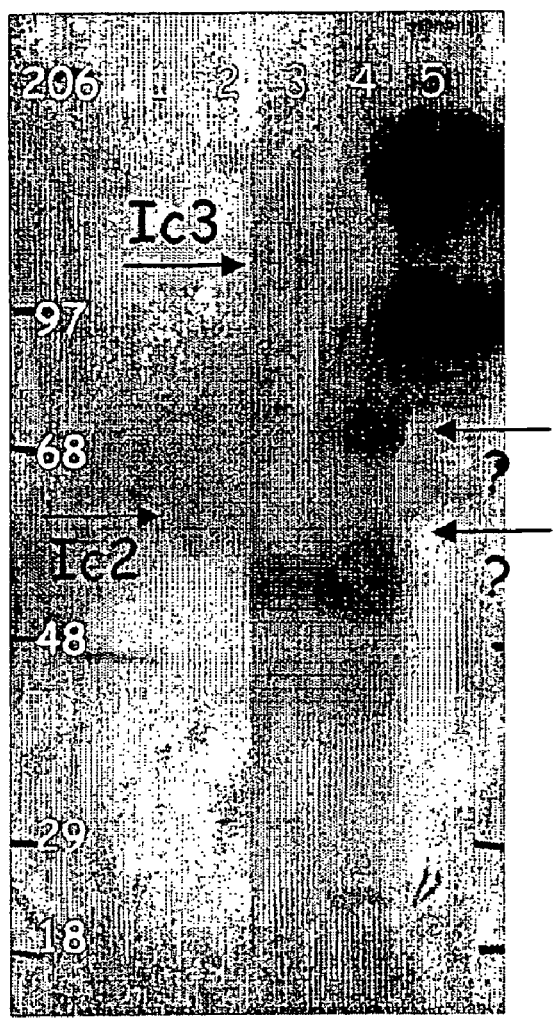

FIG. 27. A 166 kDa protein and ICAM-2 is recognized by DC-SIGN-Fc on NK cells.

NK cells are surface labelled with radioactive iodine. The cell lysate is incubated over night at 4° C. with Protein A beads coated with DC-SIGN-FC or control antibodies against ICAM-2, ICAM-3 and LFA-1. The beads are washed and the immuno-precipitated product is analysed on SDS-PAGE and visualised by autoradiography.

Figure 28:
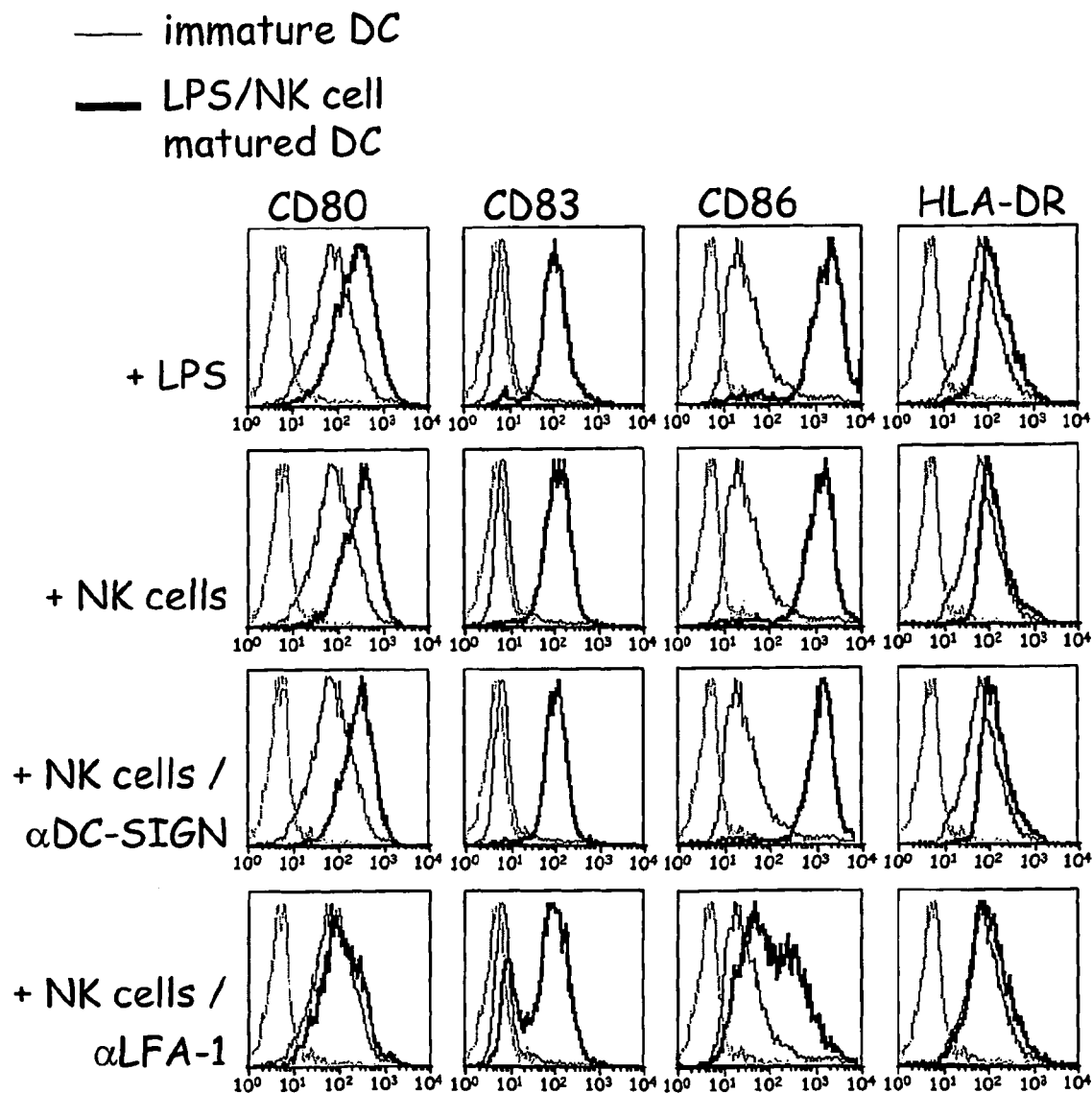

FIG. 28. Maturation of DC by NK cells is mediated by LFA-1.

Immature DC are co-cultured with NK cells for 24 hours in the presence of antibodies against DC-SIGN (AZN-D1) and LFA-1 (NKI-L19). The maturation is determined by measuring the expression of CD80, CD83, CD86 and HLA-DR. with NK cells O/N at 37° C. As a control, DC are matured with LPS (10 ng/ml).

Figure 29:
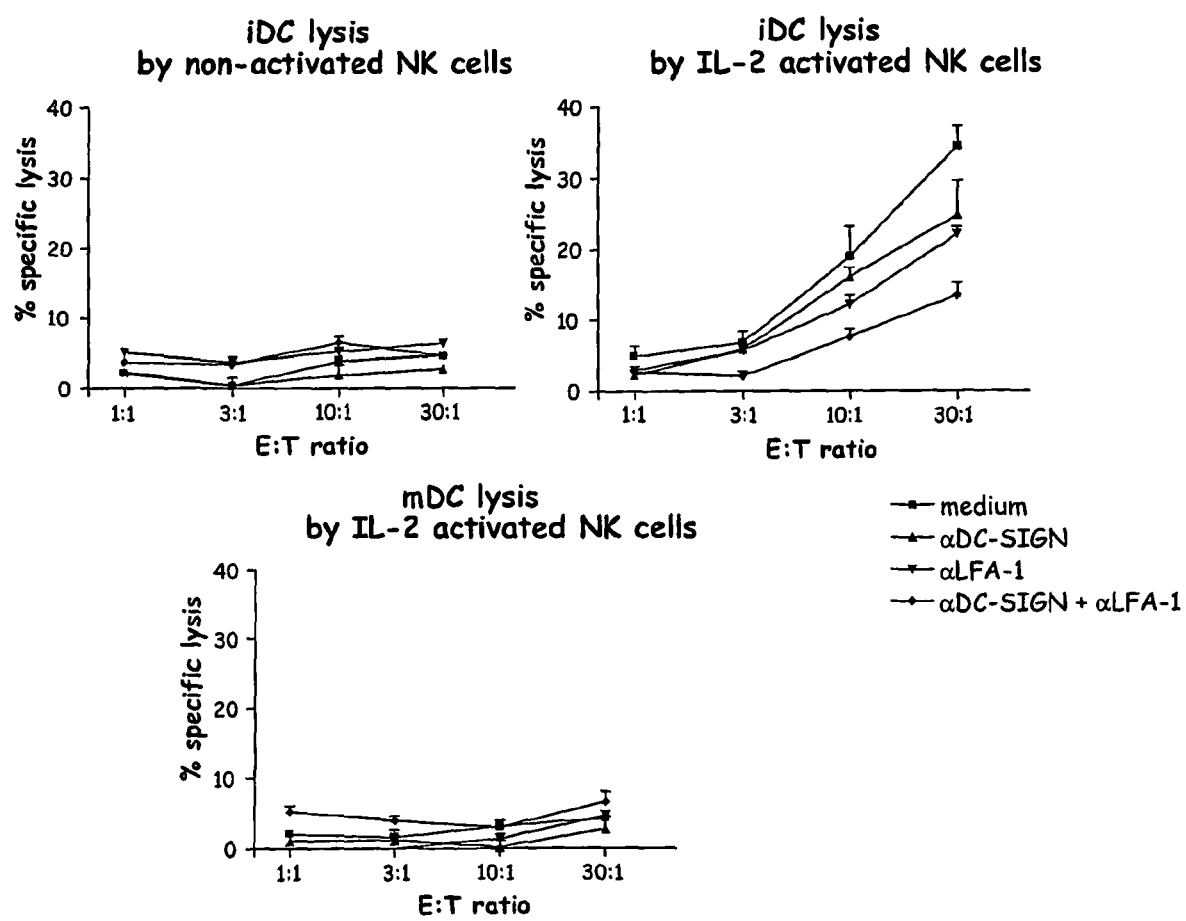

FIG. 29. NK-mediated lysis of immature DC is dependent on DC-SIGN.

Chromium$^{52}$-labeled immature or LPS-matured DC are co-cultured with IL-2-activated or non-activated NK cells for 4 hours in the presence of antibodies against DC-SIGN (AZN-D1) and LFA-1 (NKI-L19). The lysis is determined by measuring the Cr$^{52}$ release.

Figure 30:
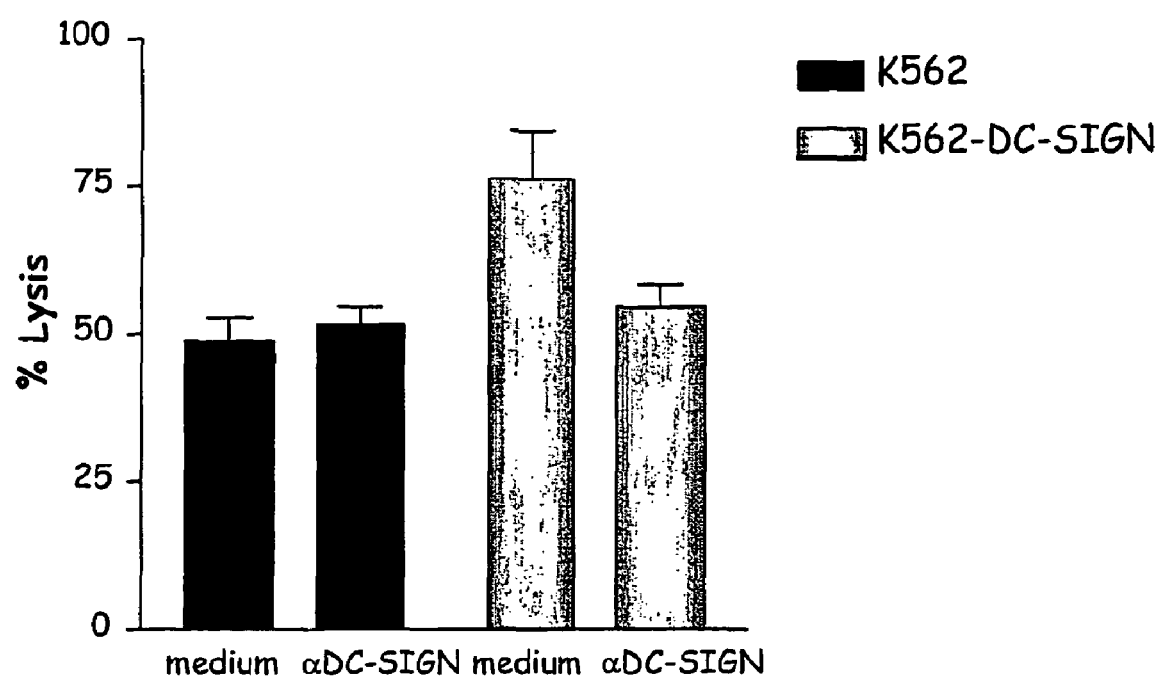

FIG. 30. NK-mediated lysis of K562 transfectants is enhanced by DC-SIGN.

Chromium$^{52}$-labeled K562 cells are co-cultured with IL-2-activated or non-activated NK cells for 4 hours in the presence of antibodies against DC-SIGN. The lysis is determined by measuring the Cr$^{52}$ release.

FIG. 31. DC-SIGN has a high affinity for HSV-1 and HSV-2.

HSV is coated in ELISA plates and DC-SIGN-Fc binding is determined in the presence of antibodies against DC-SIGN.

FIG. 32. DC-SIGN strongly binds HSV envelope glycoprotein gB.
A. DC-SIGN transfectants are incubated with HSV envelope glycoprotein-coated beads and DC-SIGN binding is determined in the presence of antibodies against DC-SIGN.
B. L-SIGN strongly binds HSV envelope glycoprotein gB.

L-SIGN transfectants are incubated with HCV envelope glycoprotein-coated beads and DC-SIGN binding is determined in the presence of antibodies against DC-SIGN.

Figure 33A:
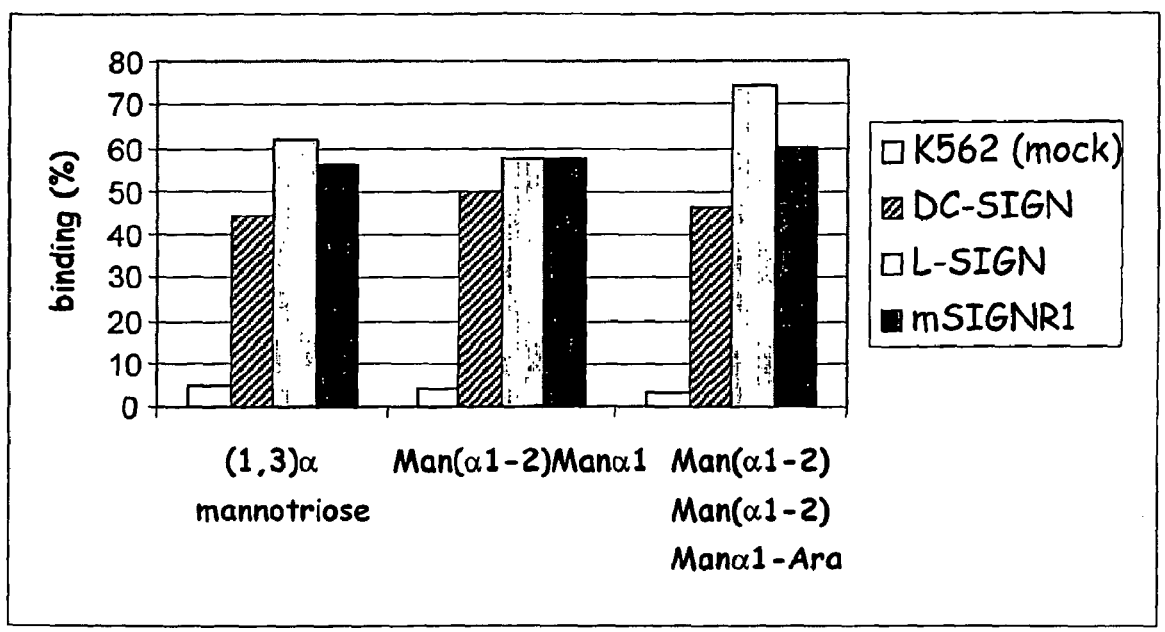

FIG. 33A. mSIGNR1 binds mannose-containing carbohydrates, similar to DC-SIGN and L-SIGN. K562 cells expressing human DC-SIGN, human L-SIGN or murine mSIGNR1 bind in a similar extent mannose-containing carbohydrates using the fluorescent bead adhesion assay.

Figure 33B:
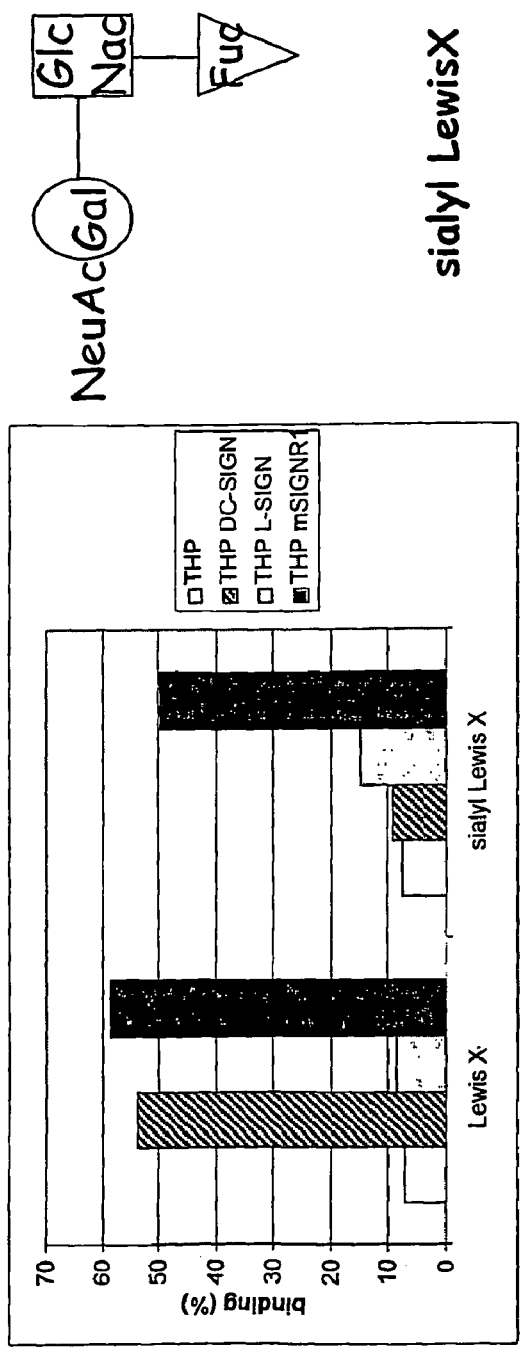

FIG. 33B. DC-SIGN, L-SIGN and mSIGNR1 bind differently to Lewis antigens. Transfectants expressing human DC-SIGN human L-SIGN or murine mSIGNR1 bind in a similar extent Lewis antigen coupled to fluorescent beads. DC-SIGN and mSIGNR1, in contrast to L-SIGN, recognize Lewis X antigen. Murine mSIGNR1 interacts with sialyl Lewis X in contrast to human DC-SIGN and L-SIGN.

FIG. 33C Carbohydrate specificity of DC-SIGN, L-SIGN and mSIGNR1 is different. Lewis X antigen is not recognized by L-SIGN, while human DC-SIGN and mSIGNR1 do. mSIGNR1 recognizes sialyl Lewis X in contrast to DC-SIGN and L-SIGN. Both human DC-SIGN and murine mSIGN1 bind sialyl Lewis A, in contrast to L-SIGN.

Figure 34:
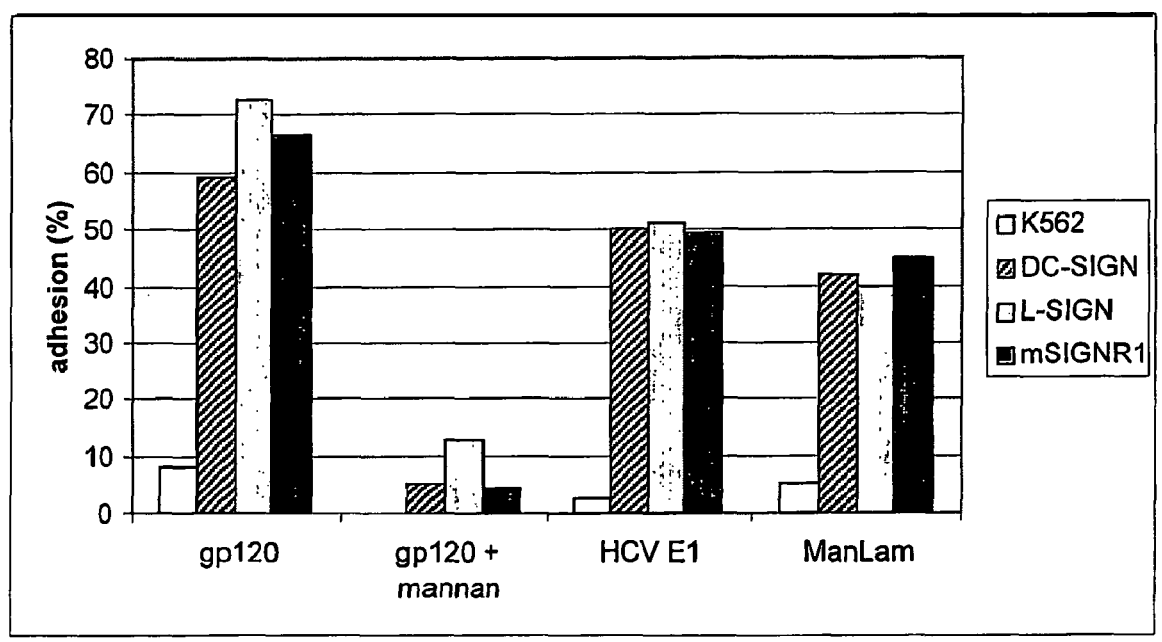

FIG. 34. DC-SIGN, L-SIGN and mSIGNR1 bind to yeast-derived mannan, Hepatitis C virus E1/E2, HIV-1 gp120 and mycobacterial ManLAM. The pathogenic ligands have been coated on fluorescent beads and the adhesion was measured using the fluorescent bead adhesion assay with K562 transfectants. Gp120 binding to DC-SIGN, L-SIGN and mSIGNR1 was inhibited using the yeast-derived carbohydrate mannan, demonstrating that these C-type lectins also bind yeast-derived mannan.

Figure 35:
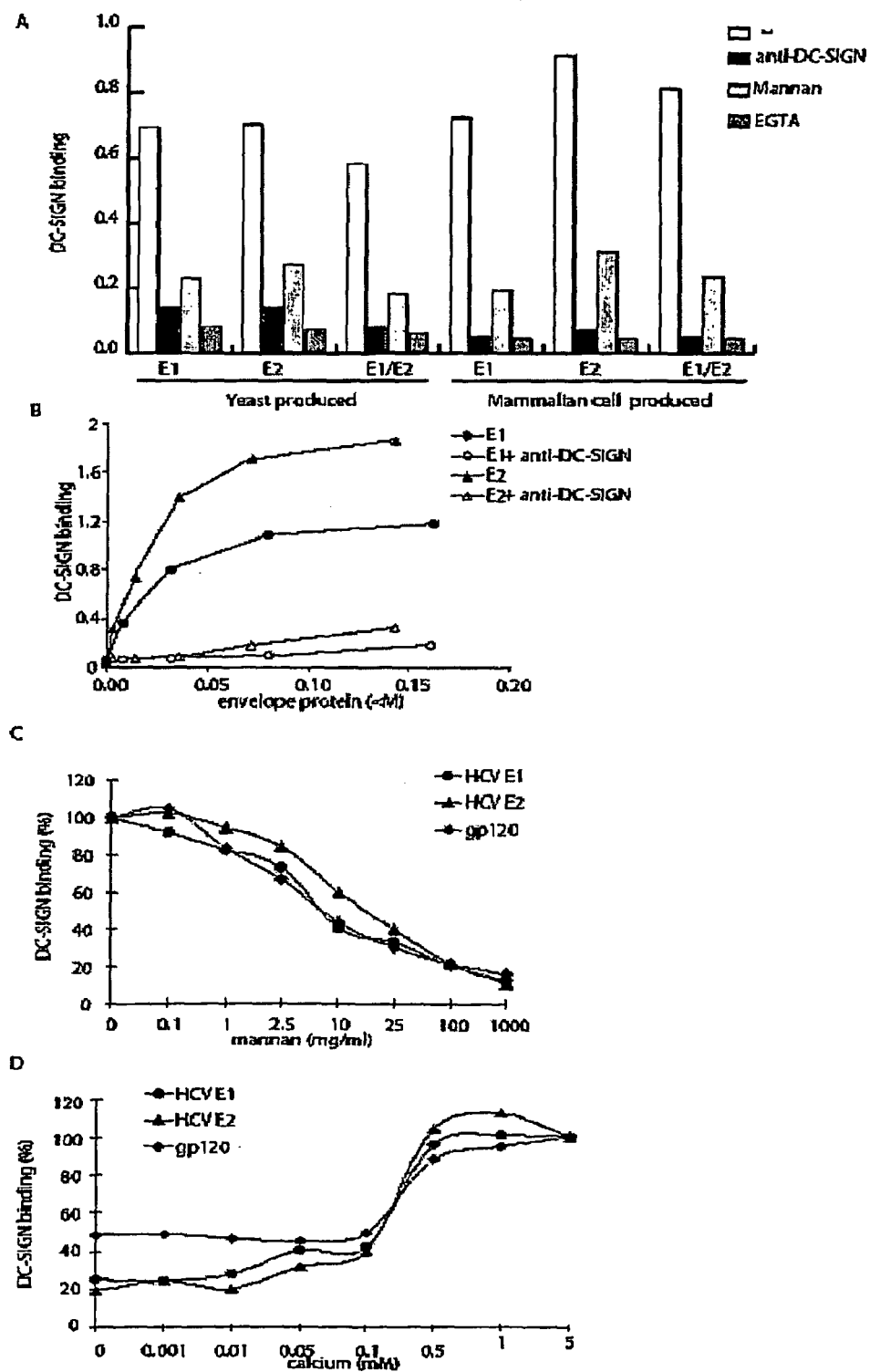

FIG. 35. DC-SIGN specifically binds HCV envelope proteins.
A. DC-SIGN binds both yeast Hansenula and mammalian cell produced HCV envelope proteins. DC-SIGN interaction with HCV envelope proteins E1 and E2 (2 mg/ml) produced by the yeast Hansenula or mammalian cells infected with recombinant vaccinia virus was tested in a Fc-based ELISA. Specificity of the binding was confirmed using the DC-SIGN specific blocking antibody AZN-D1 (50 mg/ml), mannan (100 mg/ml) or the calcium chelator EGTA (5 mM).
B. DC-SIGN interaction with HCV E1 and E2 is concentration dependent. Mammalian cell produced E1 and E2 were titrated (0-16 or 14 mM resp.) and DC-SIGN-Fc binding was tested as described above. AZN-D1 (50 mg/ml) was used to specifically block the interaction.
C. DC-SIGN has a similar affinity for E1, E2 and gp120. Mammalian cell produced E1 and E2 (10 nM) and gp120 (2 nM) were coated and DC-SIGN-Fc binding was tested as described above. Mannan was titrated (0-1000 mg/ml) to block the interaction. Binding was expressed as percentage of the binding without block.
D. DC-SIGN binding to E1, E2 and gp120 is equally dependent on calcium. Mammalian cell produced E1 and E2 (10 nM) and gp120 (2 nM) were coated and DC-SIGN-Fc binding was tested as described above in the presence of a varying of calcium (0-5 mM). Binding was expressed as percentage of binding with 5 mM calcium.

Figure 36:
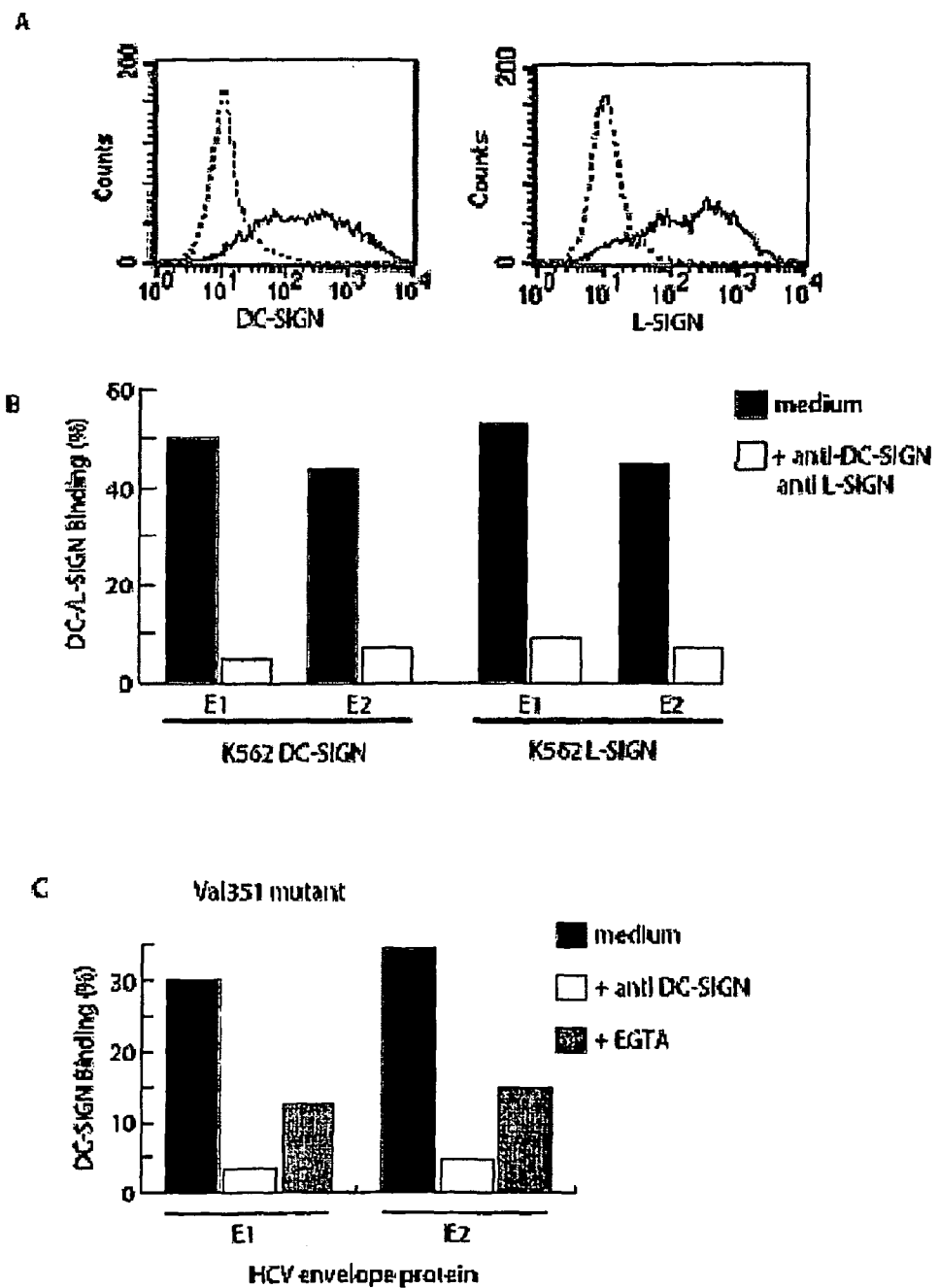

FIG. 36. HCV envelope proteins are bound by cellular DC-SIGN and L-SIGN. A K562 transfectants express similar levels of DC-SIGN and L-SIGN. B Cellular DC-SIGN and L-SIGN bind to both envelope glycoproteins E1 and E2. K562 cells transfected with DC-SIGN and L-SIGN were used to measure binding to HCV envelope protein with the fluorescent-coated bead adhesion assay. C The DC-SIGN Val351 mutant binds both HCV envelope proteins E1 and E2. DC-SIGN V351G binding to glycoproteins E1 and E2 coated beads was investigated and the specificity was determined by blocking the interaction with the DC-SIGN specific antibody AZN-D2 or the calcium-ion chelator EGTA. D. Mutational analysis demonstrate that similar aminoacids within the CRD region of DC-SIGN are involved in the recognition of HCV and HIV-1 and that those are also involved in ICAM-3 binding.

Figure 37:
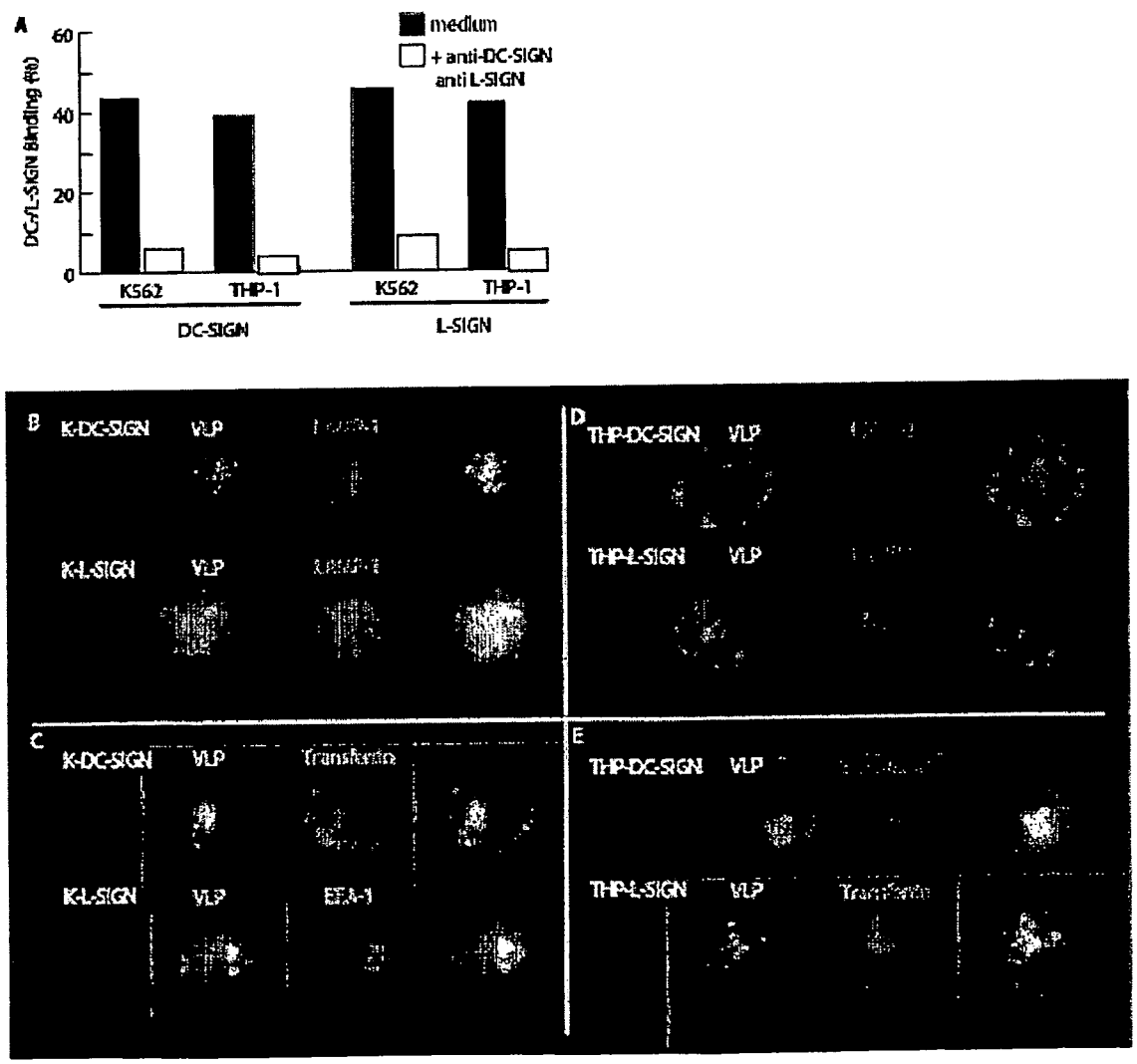

FIG. 37. Internalization pathway of DC-SIGN is dependent on the cellular background. A DC-SIGN and L-SIGN expressed by K562 and THP-1 transfectants bind HCV VLPs similarly. Binding of HCV E1/E2 VLP to K562 and THP-1 transfectants with both DC-SIGN and L-SIGN was measured using the fluorescent bead adhesion assay. B-E DC-SIGN-bound HCV is targeted to the early endosomes (transferrin+) in THP-1 cells, in contrast to the lysosomal (LAMP-1+) targeting in K562 cells. K-562 (B and C) and THP-1 cells (D and E) expressing DC-SIGN or L-SIGN were incubated overnight with HCV VLPs. HCV was detected using a human anti-HCV antibody and a fluorescent (FITC)-labeled secondary antibody. Intracellular targeting was determined by staining the endosomal compartments with a mouse antibody to the lysosomal/late endosomal specific LAMP-1 and fluorescent (Alexa Fluor 594)-labeled secondary antibody (B, D), or by co-incubating the cells for 15 minutes with Alexa Fluor 594-labeled transferrin that is specifically transported to the early endosomes and functions as a marker (C, E). Cells were analyzed by fluorescence microscopy.

FIG. 38. Dendritic cells strongly bind to HCV E1 and E2 through DC-SIGN.

A Immature DCs express high levels of DC-SIGN. Monocyte-derived dendritic cells were isolated as described in materials and methods. Expression of DC-SIGN was measured by FACS-staining with the DC-SIGN specific antibody AZN-D2. B, C Immature DCs and mature DCs bind strongly to HCV envelope proteins E1 and E2, and mixed HCV E1/E2 VLPs via DC-SIGN. Immature (B) and LPS-matured DCs (C) binding to HCV envelope proteins was determined by a fluorescent bead adhesion assay. Specificity was determined by anti-DC-SIGN antibody AZN-D2 (50 mg/ml), mannan (100 mg/ml), EGTA (10 mM), and anti-mannose receptor antibody (clone 19) (50 mg/ml).

Figure 39:
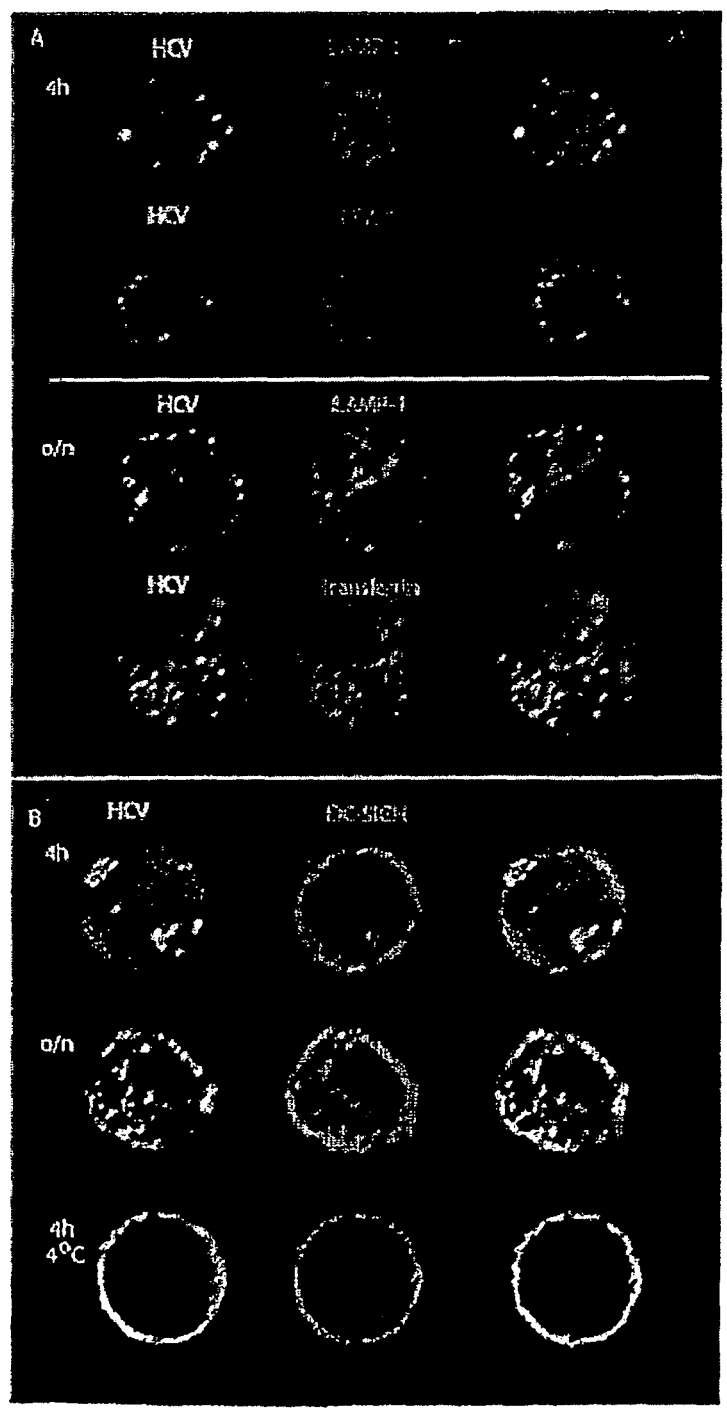

FIG. 39. DC-SIGN on iDC targets HCV VLPs to early endosomes. A Immature dendritic cells were incubated with HCV VLPs (30 mg/ml) for 4 hours or overnight. HCV was detected with a human anti-HCV antibody and a FITC-labeled secondary antibody. Intracellular targeting was determined by staining the endosomal compartments with a mouse antibody to the lysosomal/late endosomal specific LAMP-1 or the early endosome specific marker EEA-1 and an Alexa Fluor 594 labeled secondary antibody, or by co-incubating the cells for 15 minutes with Alexa Fluor 594 labeled transferrin which is specifically transported to the early endosomes. B Immature dendritic cells were incubated with HCV VLPs (30 mg/ml) for 4 hours or overnight at 37 or 4° C. HCV was detected as described for FIG. 5A. Localization of DC-SIGN was determined with the DC-SIGN specific antibody AZN-D2 and an Alexa Fluor 594 labeled secondary antibody.

Figure 40:
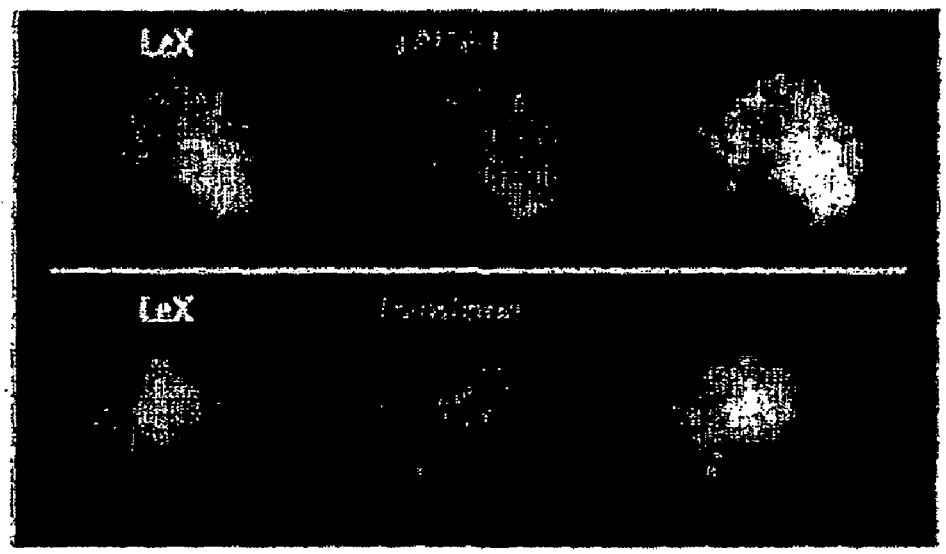

FIG. 40 DC-SIGN on iDCs targets its ligand Lewis X antigen to late endosomes/lysosomes. Immature dendritic cells were incubated with Lewis X (10 mg/ml) for 4 hours. Intracellular targeting was determined by staining the endosomal compartments with a mouse antibody to the lysosomal/late endosomal specific LAMP-1 or by co-incubating the cells for 15 minutes with Alexa Fluor 594 labeled transferrin which is specifically transported to the early endosomes. Cells were analyzed by fluorescence microscopy.

Figure 41:
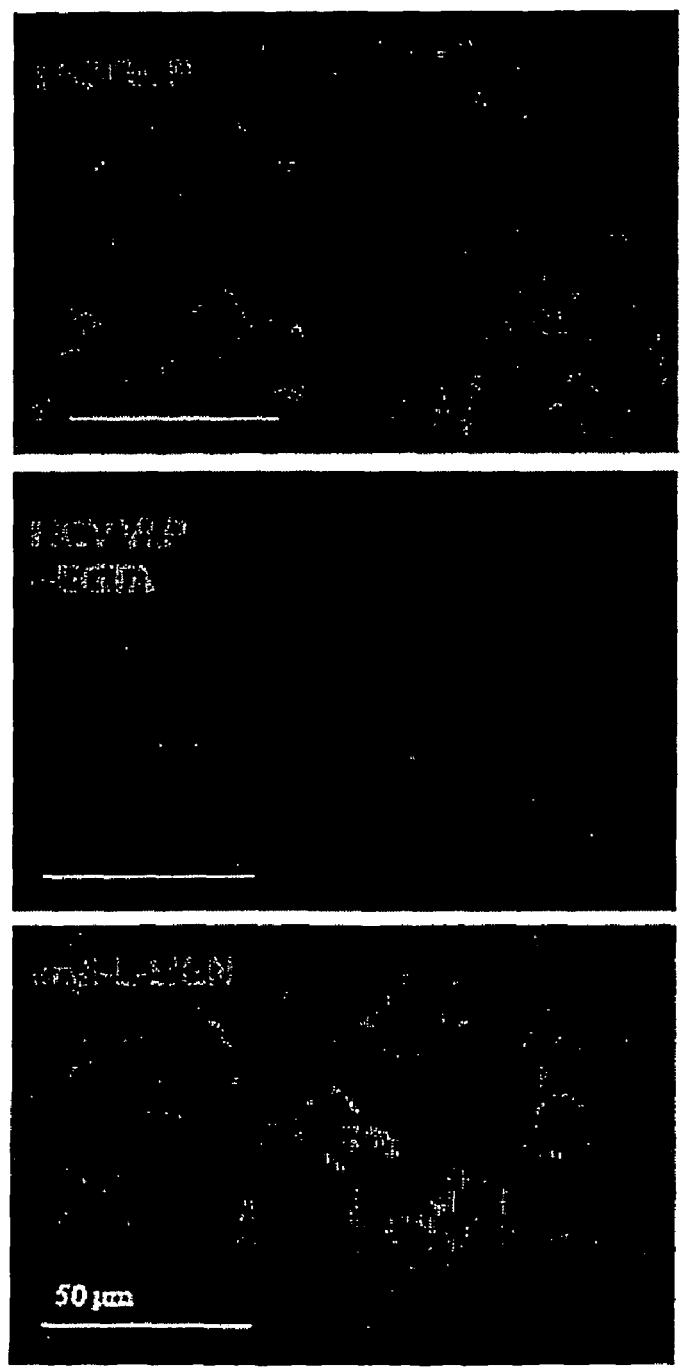

FIG. 41. HCV interacts with L-SIGN expressing human liver sinusoidal endothelial cells (LSECs) in situ. (A) L-SIGN is expressed by human LSECs, as was determined by staining of liver tissue with an L-SIGN specific antibody. (B) Binding of HCV VLPs by liver tissue was determined by incubating liver sections with HCV VLPs for 2 hours at 37° C. HCV binding was detected using a mouse anti-HCV antibody and an Alexa Fluor 594 labeled secondary antibody. (C) HCV VLP binding to LSECs was blocked by the calcium chelator EGTA.

FIG. 42. Lewis blood group antigens and some of their related structures bind to DC-SIGN. (a) Lewis blood group antigens expressed by *H. pylori*.

(b-c) Carbohydrates, representing blood group antigens or their substructures, conjugated to polyacrylamide (b), or ceramide (c), were coated and binding of recombinant DC-SIGN-Fc was measured using the DC-SIGN-Fc ELISA.

Figure 43:
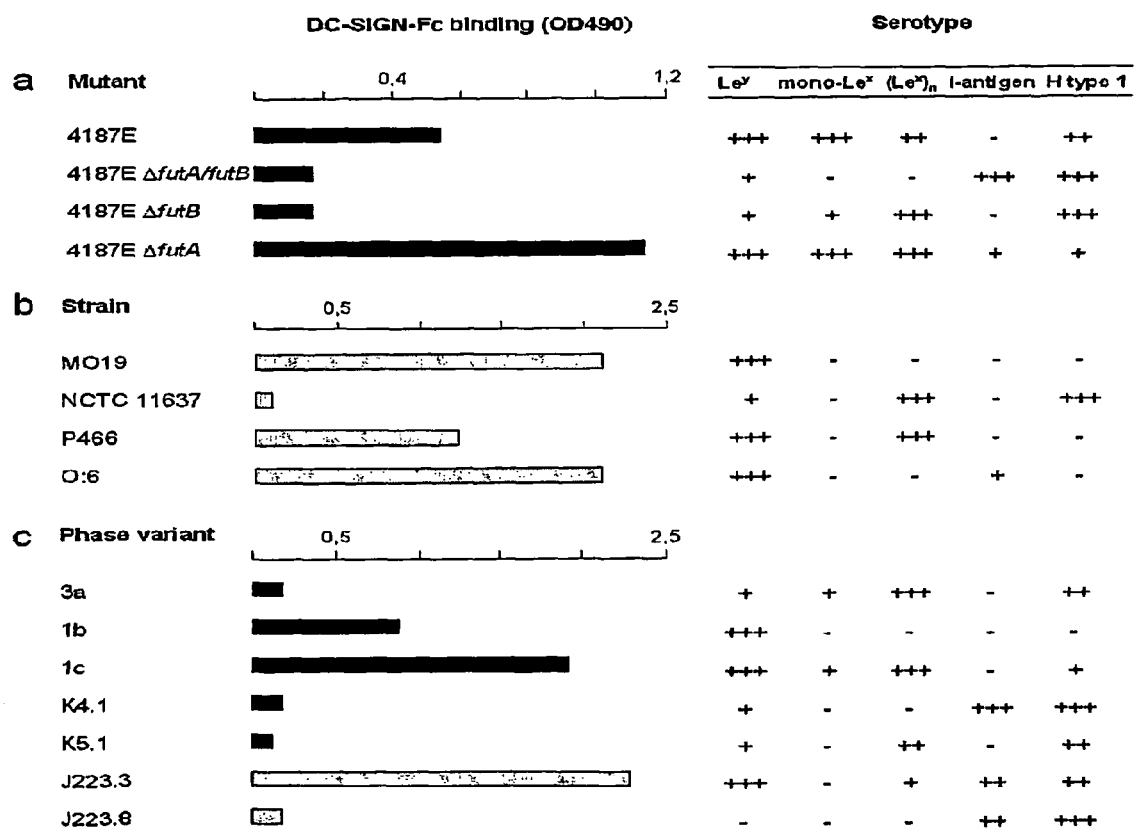

FIG. 43. Binding of *H. pylori* is dependent on Lewis antigen expression.

(a-c) *H. pylori* α3-fucosyltransferase mutants (a), strains (b) and phase variants (c) were coated and binding of recombinant DC-SIGN-Fc was measured after incubation with peroxidase-labeled goat-anti-human Fc. *H. pylori* were coated and incubated with antibodies specific for Lewis antigens as indicated and their serotype was determined after incubation with peroxidase-labeled anti-mouse immunoglobulins.

FIG. 44. LPS phase variation in *H. pylori* occurs in vivo.

(a) Lex/y positive phase variants of J223 were detected by colonyblotting with mAbs specific for the indicated Lewis antigens, after short time culturing directly from the biopsy, followed by one single passage in fluid phase and distribution over solid media. (b) C-tract sequencing was performed to determine the "on" and "off"-status of genes futA (HP0379) and futB (HP0651). The J223.3 futB mutant was generated by natural transformation with construct containing a chloramphenicol resistance marker cassette inserted in gene HP0651, and serotyped as indicated for J223. (c) Consequences of the C-tract length for functional expression of futa and futB.

Figure 45:
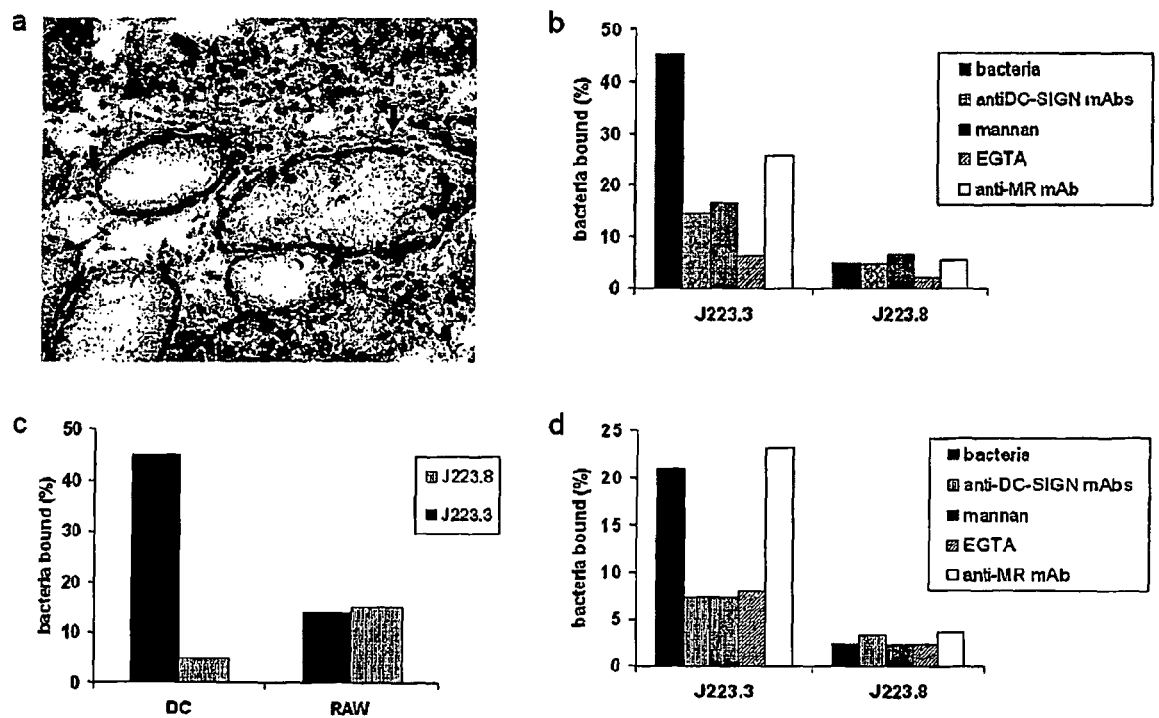

FIG. 45. DC-SIGN is expressed on gastric DCs and is the major receptor for Le positive *H. pylori*.

(a) A tissue section of stomach was fixed and stained with anti-DC-SIGN antibodies. Original magnification×20. Arrows indicate DC-SIGN positive DC-like cells in the lamina propria. (b-d) Monocyte derived DCs (b), monocyte-derived DCs and RAW macrophages (c) or K-562 cells transfected with DC-SIGN (d) were incubated with FITC labelled *H. pylori* J223.3 or J223.8 and binding was analyzed using flowcytometry. In b and d, cells were preincubated with anti-DC-SIGN antibodies, mannan, EDTA, or anti-mannose receptor (MR) antibodies.

FIG. 46. Binding of *H. pylori* to induces DC-SIGN-dependent increase of cytokines IL-10 and IL-12 production, but no changes in IL12p70.

(a) DC were incubated with *H. pylori* J223.3 or J223.8 at an multiplicity of infection (M.O.I.) of 20 in the presence or absence of anti-DC-SIGN antibodies for 1 hr, washed and cultured for 20 hrs. Supernatant was harvested and the amount of IL-10 and IL-12p40 was analyzed by ELISA.

(b) Upon coculture of DC with *H. pylori* J223.3 or J223.8, cells were incubated with CD40L-transfected J558 fibroblasts in the absence or presence of IFN-γ for 24 hrs. Supernatant was harvested and the amount of IL-12p70 was analyzed by ELISA.

Figure 47:
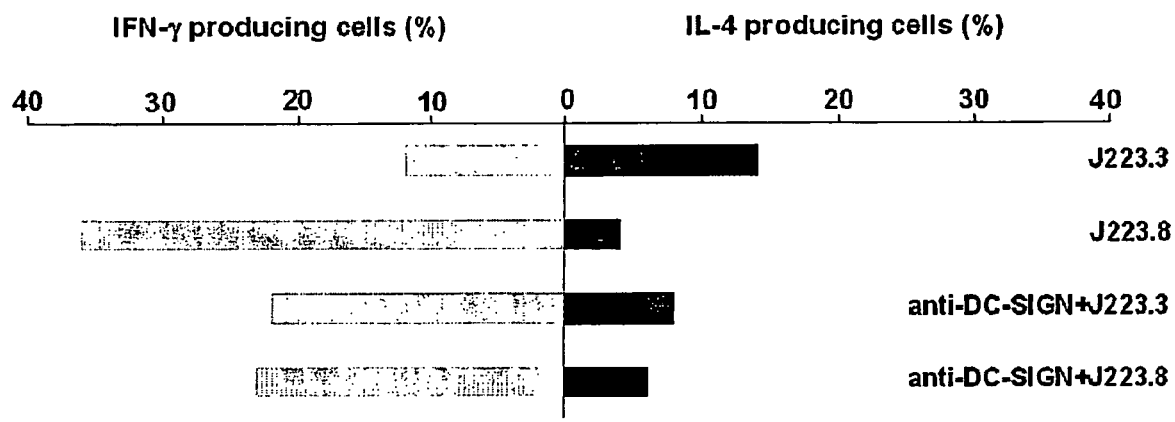

FIG. 47. Binding of *H. pylori* to DC-SIGN induces skewing of naive T cells to Th2.

After preincubation with anti-DC-SIGN antibodies, DC were incubated with *H. pylori* J223.3 or J223.8 at an M.O.I. of 10 for 48 hrs, washed and subsequently cocultured with highly purified CD45RA+CD4+ T cells. Quiescent T cells were re-stimulated with PMA and ionomycin and IL-4 and IFN-γ was analyzed on a single-cell basis by intracellular flowcytometry.

Figure 48A:
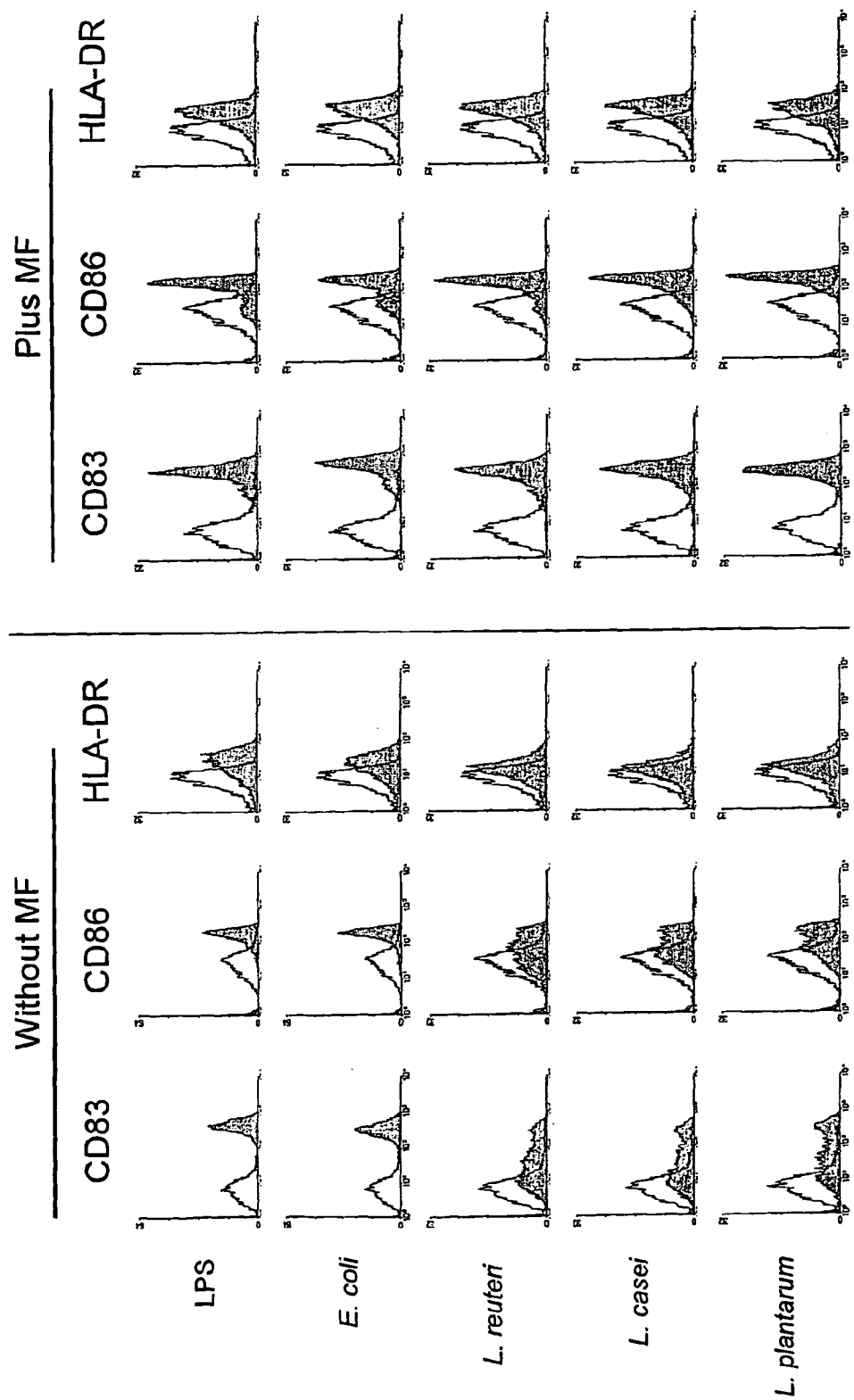
Figure 48B:
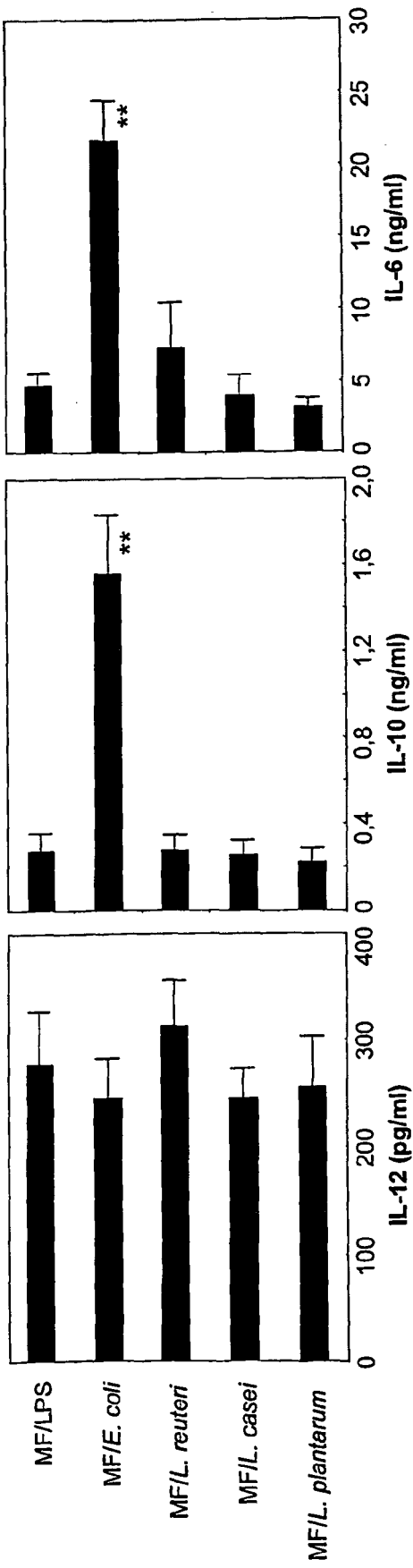
Figure 49A:
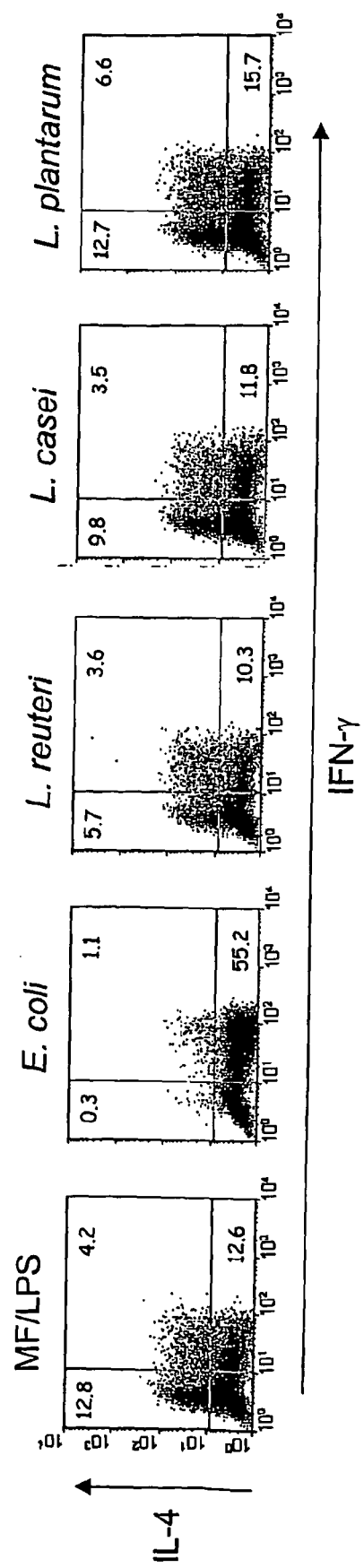
Figure 49B:
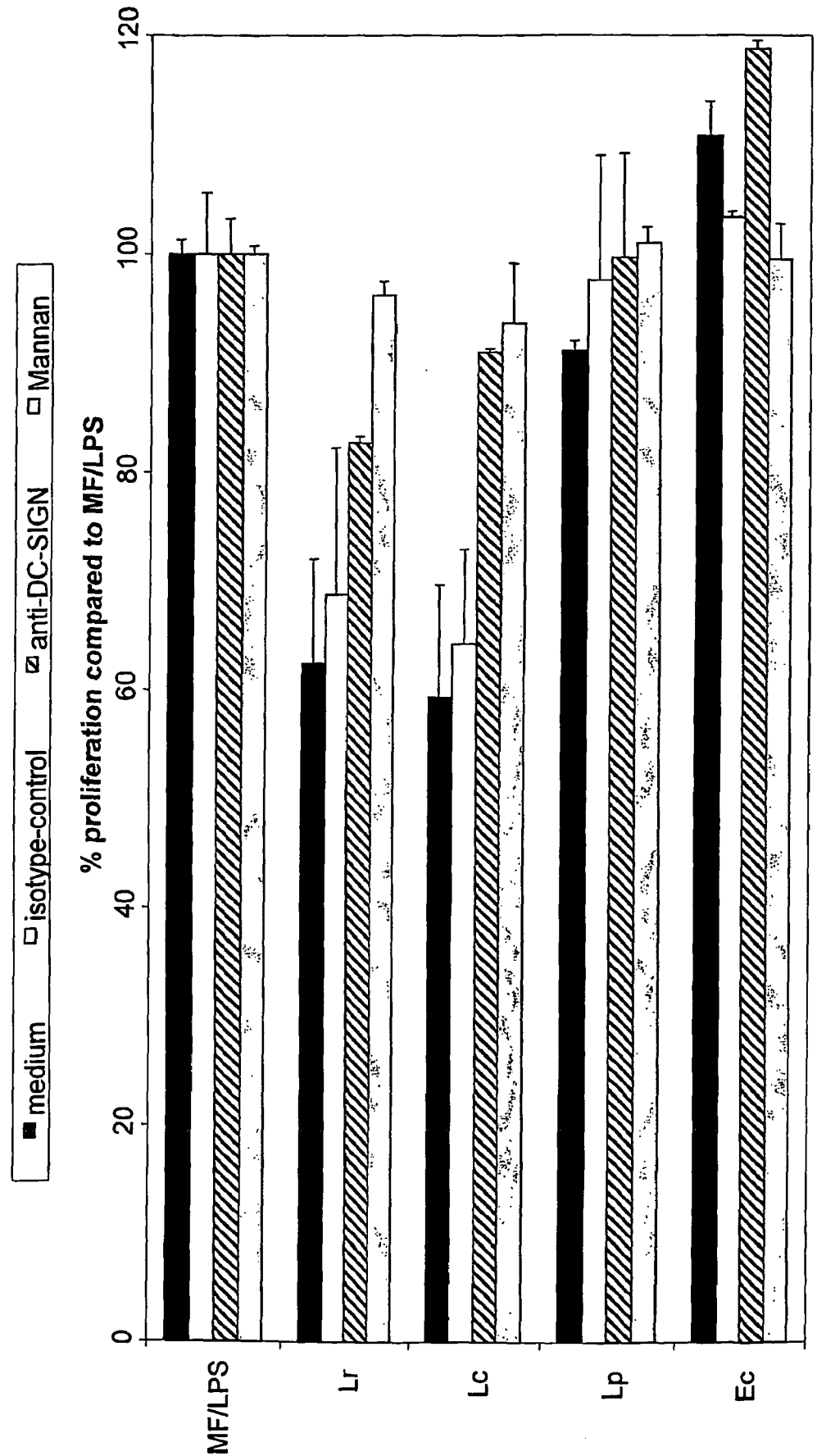
Figure 49C:
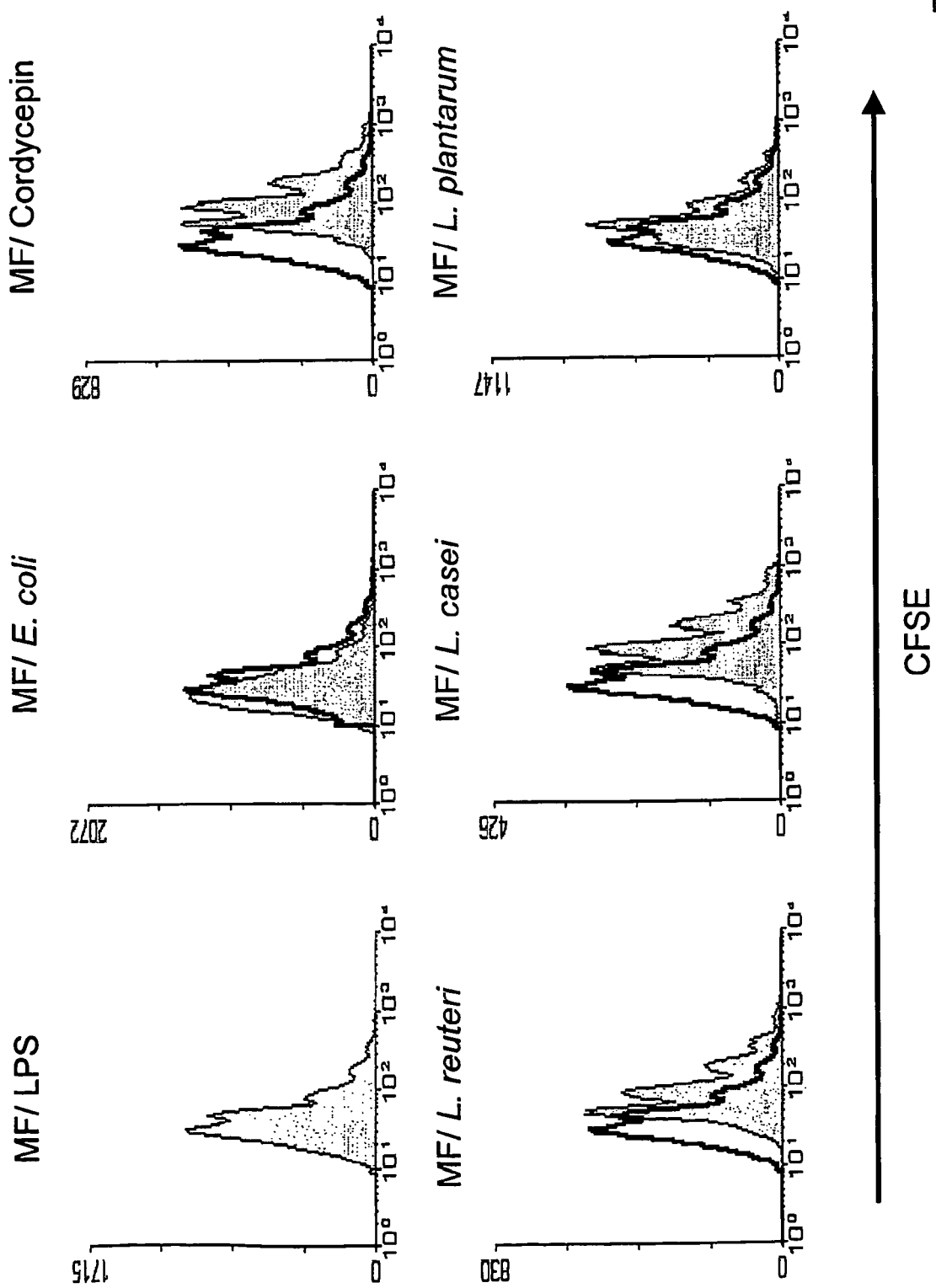
Figure 49D:
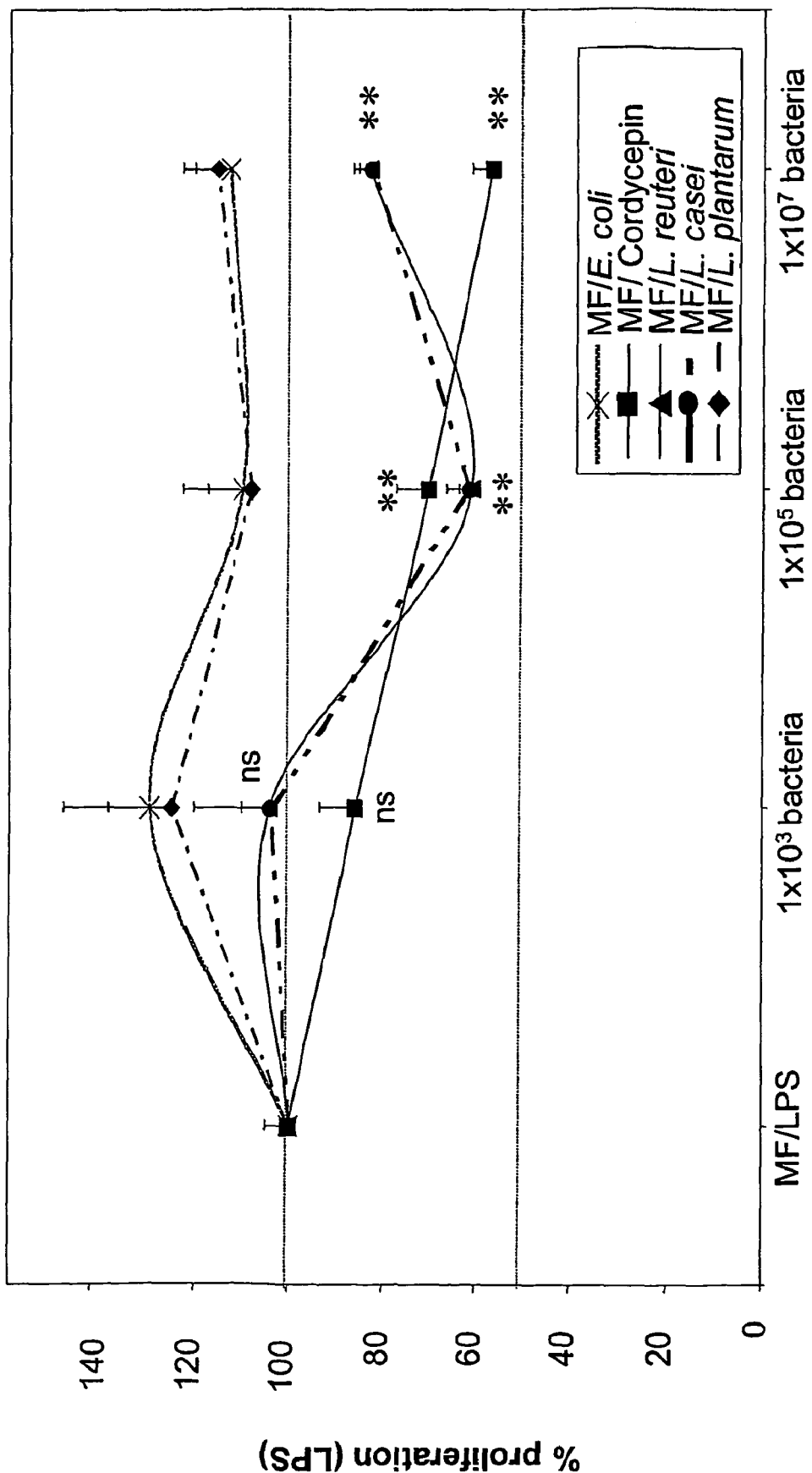

FIG. 48: Lactobacilli induce partial DC maturation.

Immature DC (iDC) were generated as described A) Maturation was induced by addition of LPS (100 ng/ml), 107 bacteria, LPS plus MF (rIL-1b (25 ng/ml) and rTNFa (50 ng/ml)), or MF plus 1.107 bacteria. After 48 h, mature DC (mDC) were harvested, washed and (A) surface expression of CD86, HLA-DR and CD83 was analyzed by flowcytometry. (B) Mature DC (2.104 cells/well) were stimulated with mouse CD40L-expressing mouse fibroblast cells (J558 cells, 2×104 cells/well) to induce the production of IL-12, IL-10 and IL-6. After 24 h, supernatants were collected and IL-12p70, IL-10 and IL-6 production were measured by ELISA.

FIG. 49: *L. reuteri* and *L. casei* induce regulatory T cell development by modulation of DC function.

Generation of iDC and maturation conditions are described in the legend to FIG. 16. (A) Mature DC ($5\times10^3$ cell/well) were cocultured with naive helper T cells (Th cells) ($2\times10^4$ cells/well) and superantigen SEB (10 pg/ml). After 12 days, IFN-g and IL-4 productions per cell were analyzed by intracellular FACS-staining following a 6 h PMA/ionomycin stimulation, the last 5 h in the presence of Brefeldin A. (B) Mature DC ($2.5\times10^3$ cell/well) were cocultured with naive Th cells ($5\times10^4$ cells/well). Cell proliferation was assessed by the incorporation of radioactively-labeled [3H]-TdR after a pulse with 13 KBq/well during the last 16 h of 6-day culture after stimulation, as measured by liquid scintillation spectroscopy. (C) Naive Th cells were stimulated as described in part A. After 12 days, the test cells were fluorescently-labeled with PKH, and stimulated with suboptimal concentrations of anti-CD3 (1:5000) and anti-CD28 (1:2000). After overnight incubation, fluorescent(CFSE)-labeled target T cells (peripheral CD4+ T cells), were added in a 1:1 ratio ($2.5\times10^4$ each). After 5 days the PKH and CFSE staining of the cells were analyzed by flowcytometry. The gray shade CFSE profile represents the test condition (bacteria: 105), whereas the overlay indicates the proliferation in the presence of control test cells (MF/LPS). The figure is a representative out of 7 independent experiments. (D) The mean fluorescence intensity (MFI) of the CFSE-labeled target cells cocultured in the presence of control test cells (MF/LPS) was set at 100%, representing the maximal proliferation. The MFI of the target T cells cocultured with other test cells was compared to this value, calculating the relative proliferation. The results are expressed as the mean percentages±SEM from 4-7 independent experiments (Cordycepin: 25-12.5-6.25 µg/ml). Data were analyzed for statistical significance using ANOVA followed by Bonferroni's multiple comparison test. * $P<0.05$, ** $P<0.01$.

Figure 50A:
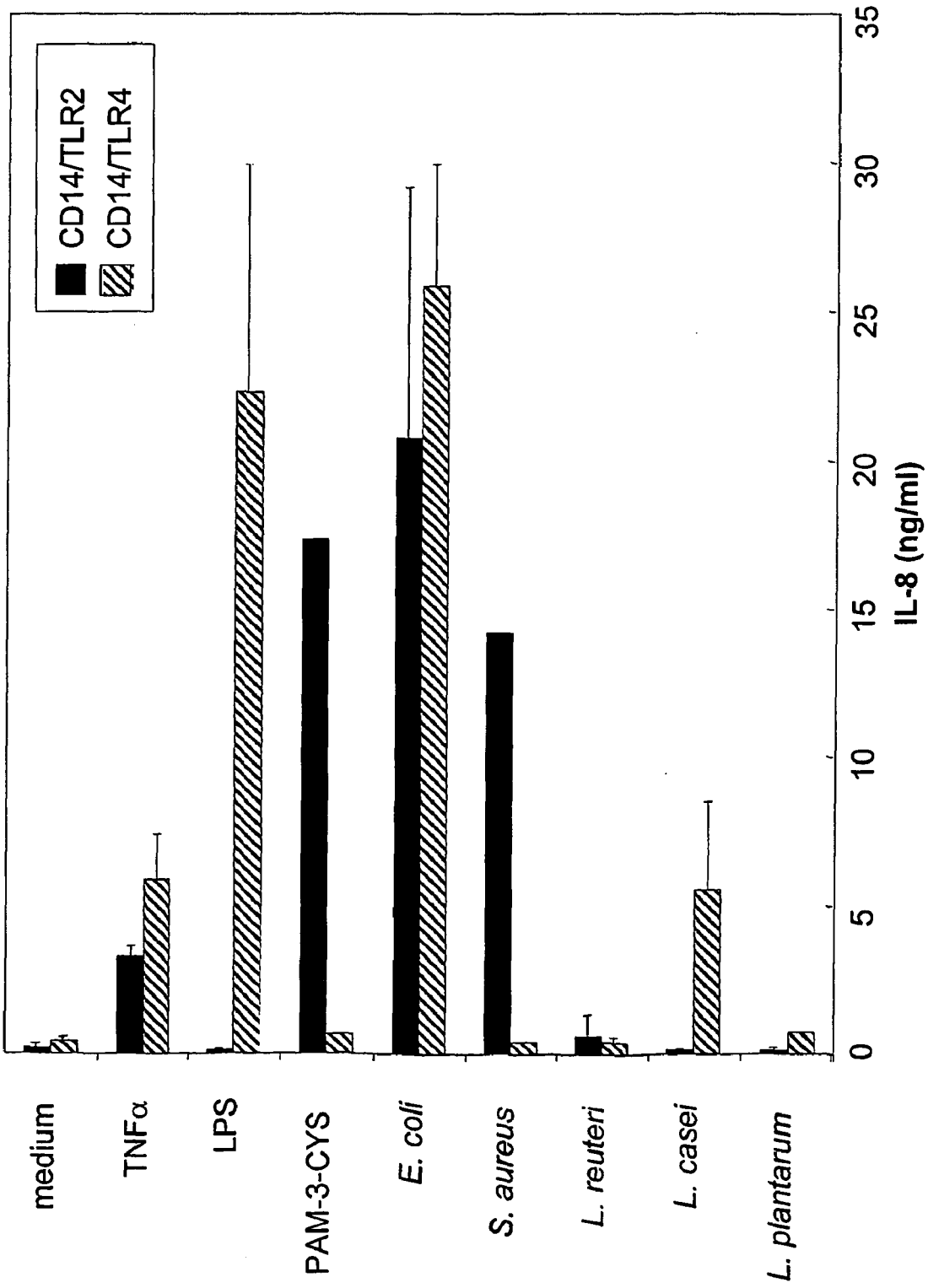
Figure 50B:
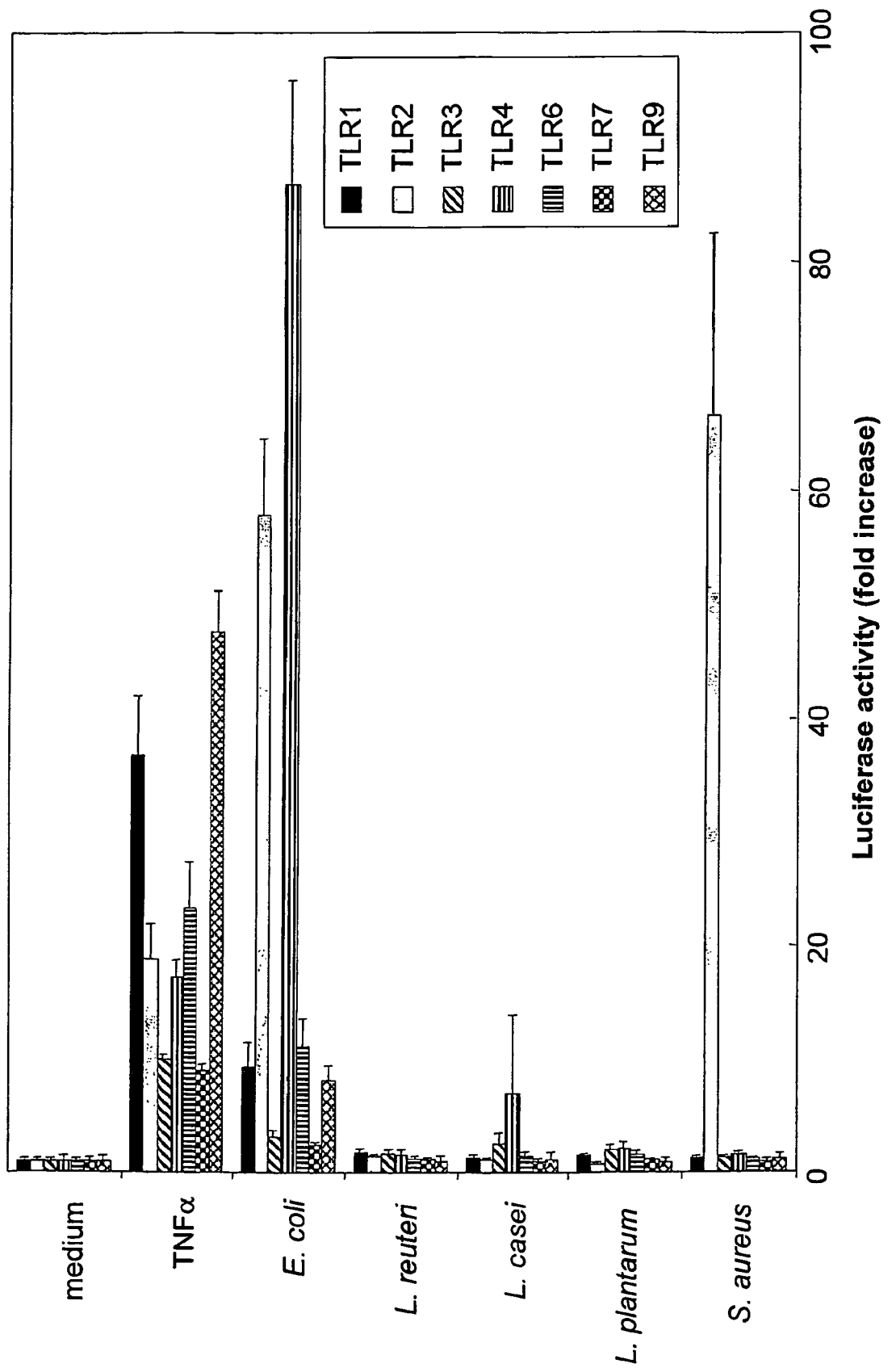

FIG. 50: No TLR activity by Lactobacilli.

(A) Stable transfected HEK 293 cells with either TLR2 or TLR4 were seeded at $0.2\times10^6$ cells/well and stimulated with $10^7$ bacteria/ml or TNFa. After 24 hours, supernatant was taken and IL-8 content was analyzed by ELISA. (B) HEK 293 cells were transiently transfected with human TLR1, TLR2, TLR3, TLR4+MD2, TLR6, TLR7 and TLR9, together with an ELAM-luciferase reporter construct and were stimulated with $10^7$ bacteria or TNFa. Luciferase activity was determined 6 h after stimulation.

Figure 51A:
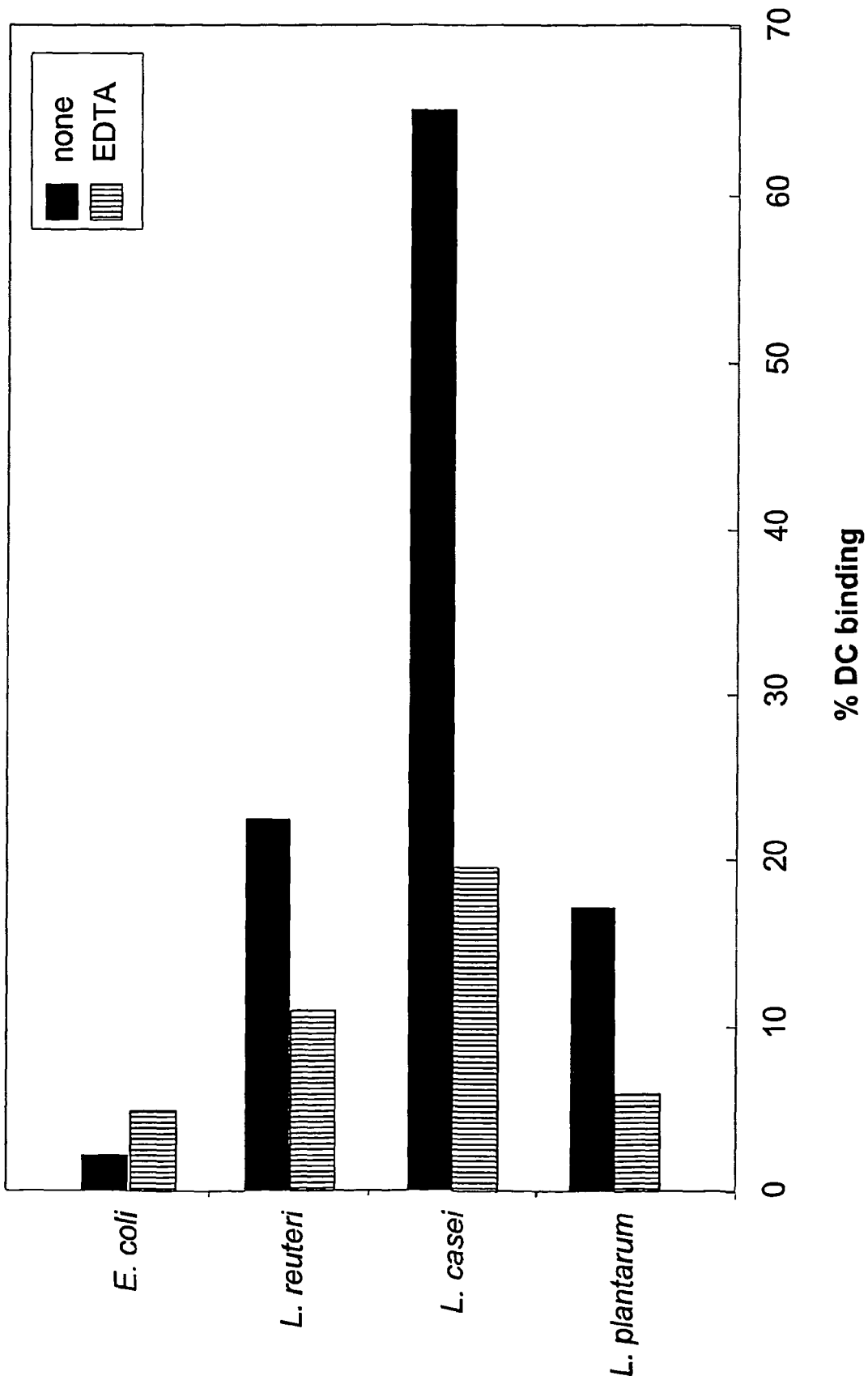
Figure 51B:
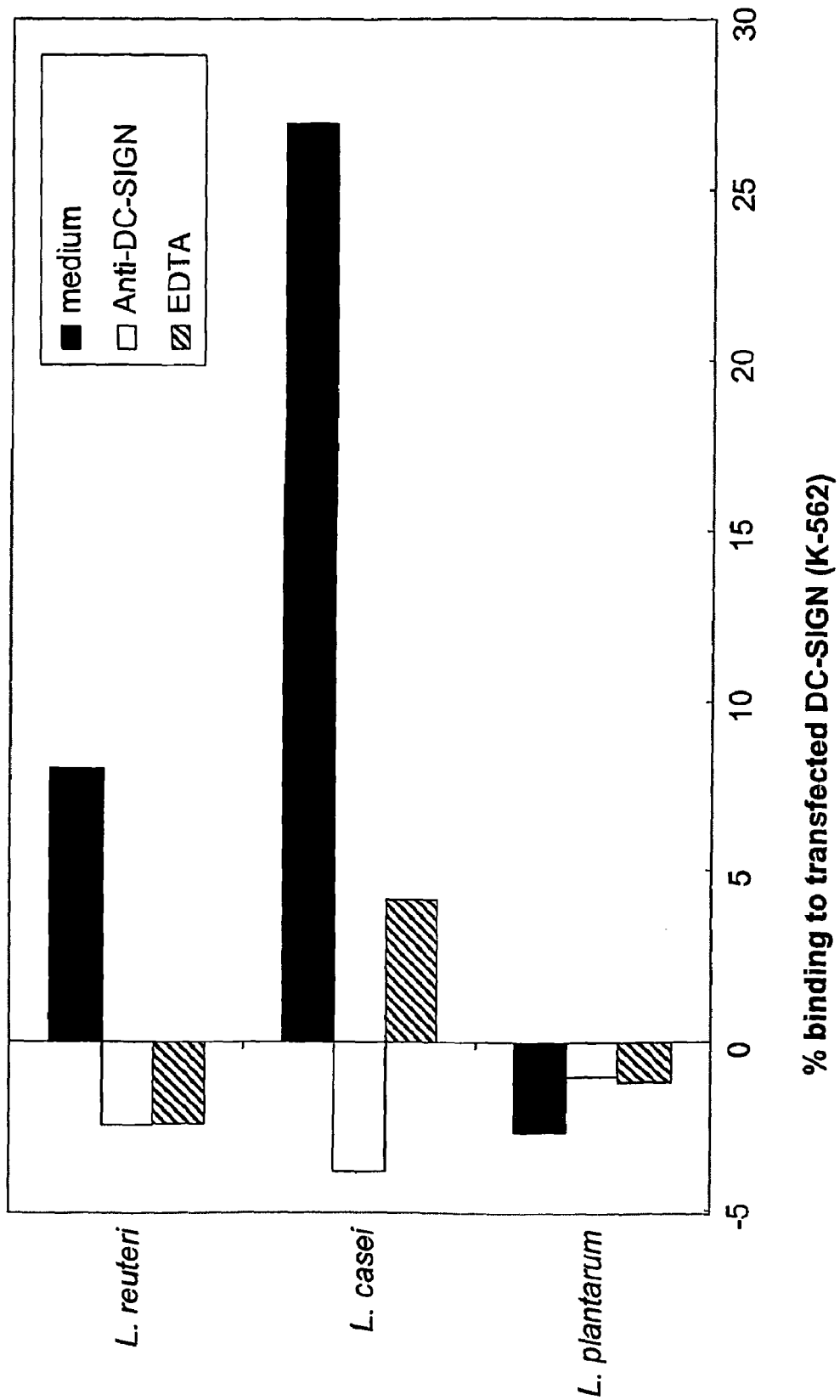
Figure 51C:
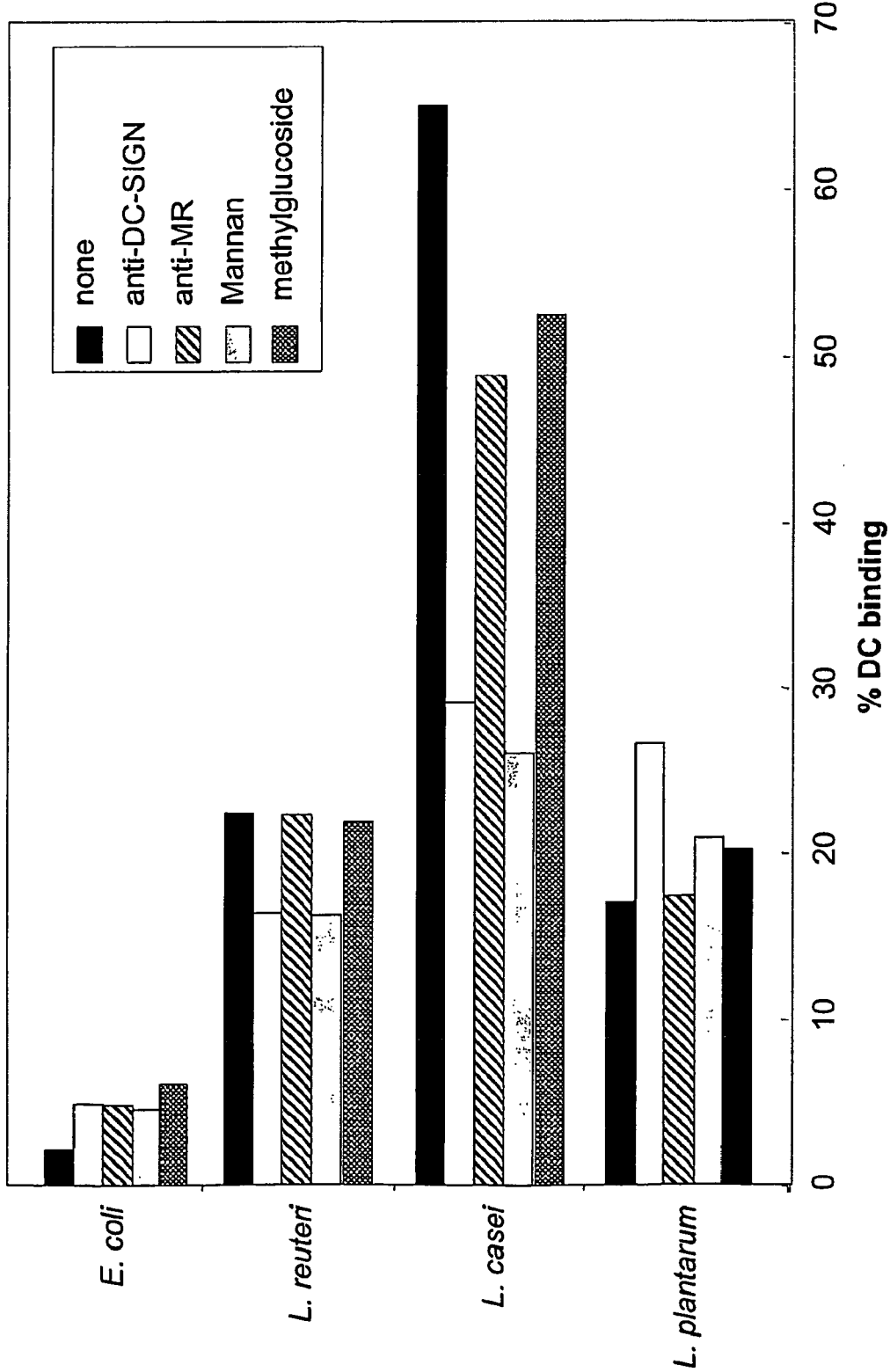

FIG. 51: *L. reuteri* and *L. casei* ligate DC-SIGN on moDC.

(A). Immature DC were incubated with FITC-labeled bacteria. After washing, the cells were analyzed by flow cytometry. (B) Similar protocol, as described in the part A, was used to analyze bacteria binding to DC-SIGN-transfected K562 or untransfected K562 cells. Preincubations were performed with either TSM+0.5% BSA, EDTA or anti-DC-SIGN (AZN-D1 and AZN-D2, 20 µg/ml). (C) DC-binding was performed as described in part A. Preincubations were performed with either TSM+0.5% BSA, anti-DC-SIGN (AZN-D1 and AZN-D2, 20 µg/ml), anti-MR, Mannan or methylglucoside.

Figure 52:
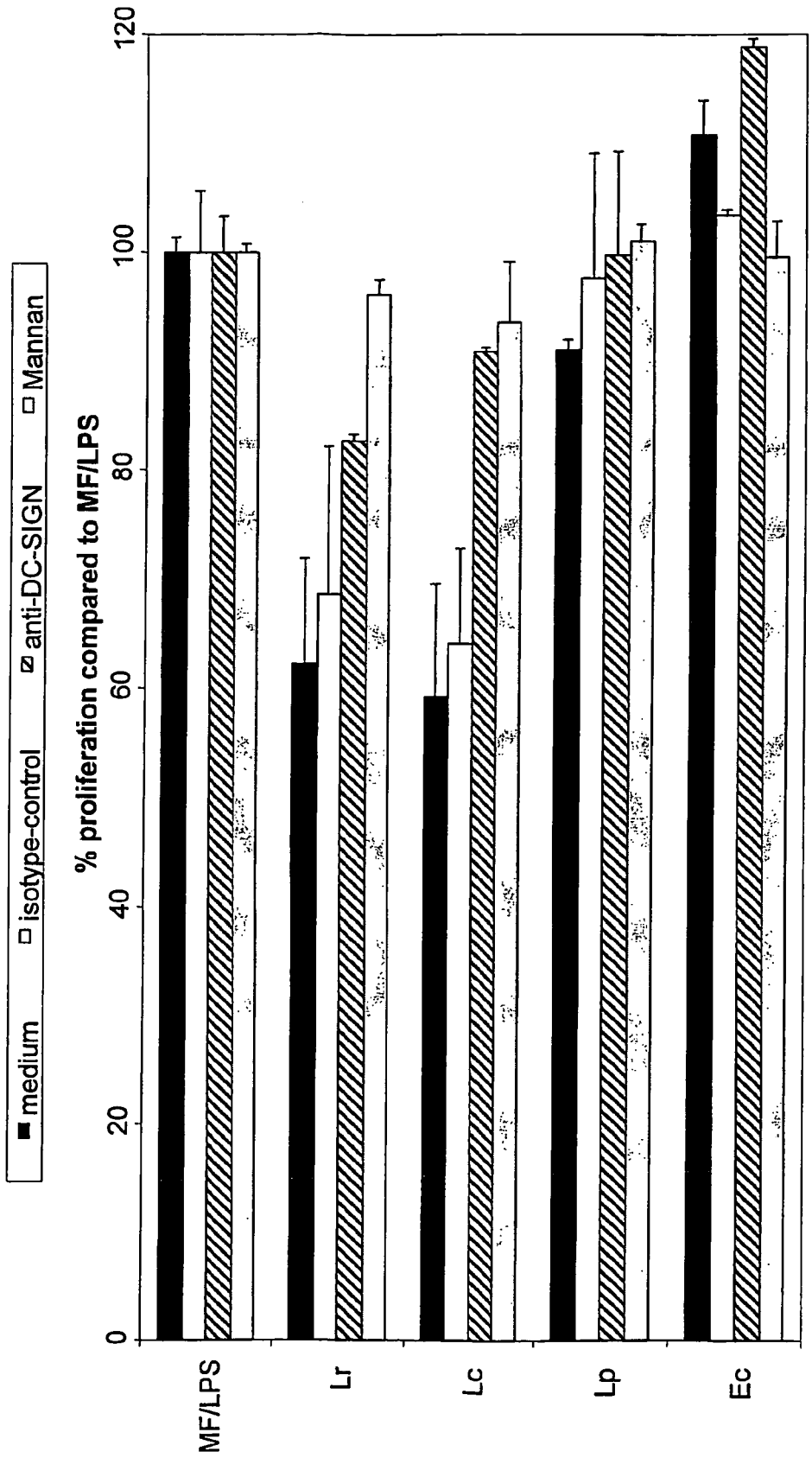

FIG. 52: Blocking of DC-SIGN interaction with *L. reuteri* and *L. casei* abrogates the priming for regulatory T cell development.

Generation of iDC is described in the legend to FIG. 1. Immature DC were preincubated (30 min, 37° C.) with either isotype control Ab, anti-DC-SIGN (AZN-D1; 20 µg/ml) or Mannan. Thereafter maturation was conducted as described in the legend to FIG. 16. Induction of suppressor cell activity was analyzed as described in the legend to FIG. 17.

Figure 53:
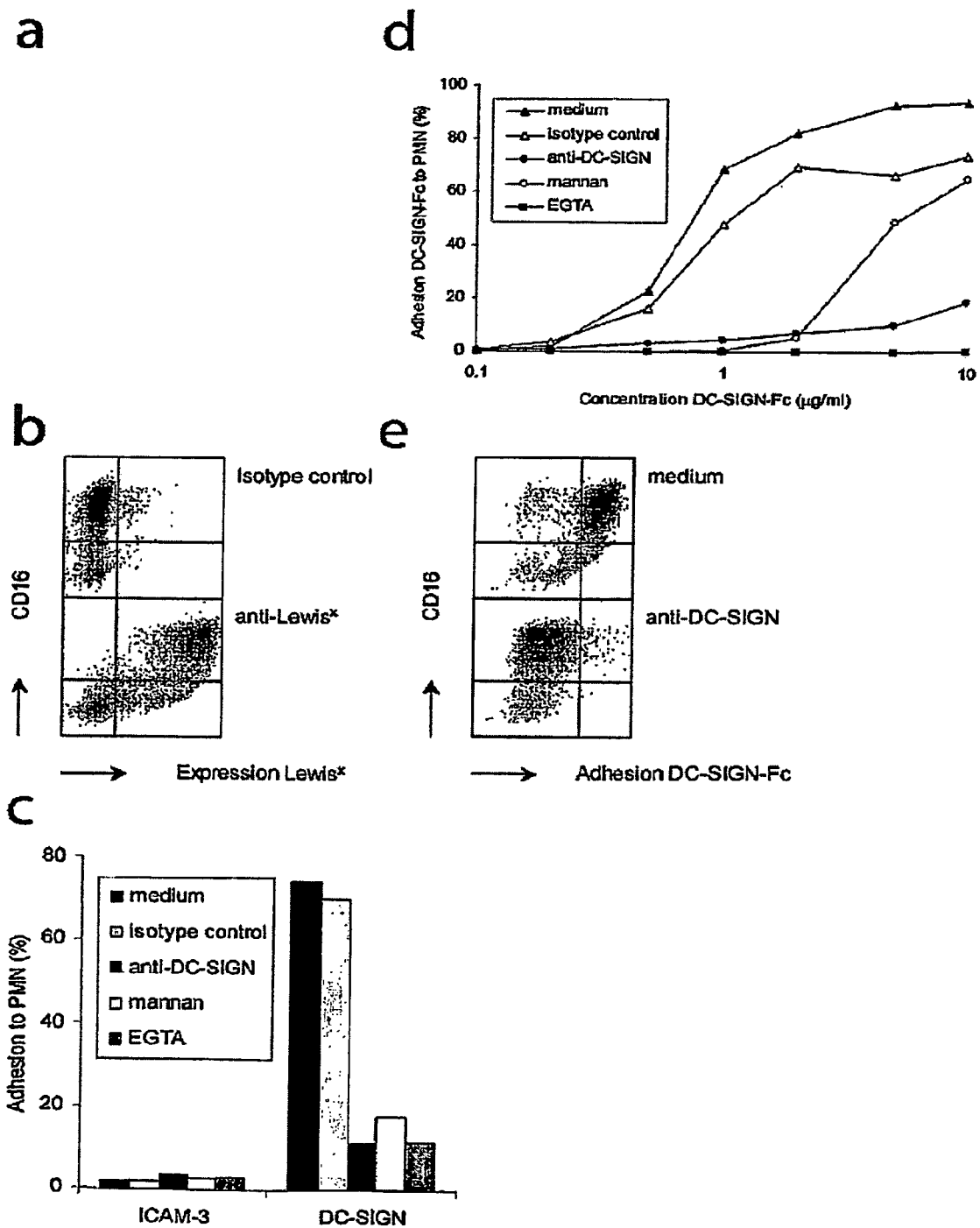

FIG. 53. Polymorphic Mononuclear Neutrophisl (PMN) express the DC-SIGN ligand Lewisx and bind with high affinity to recombinant DC-SIGN. A. Polyacrylamide glycoconjugates of Lewisx and sialylated Lewisx were coated and adhesion of DC-SIGN-FC was measured with peroxidase labeled goat anti-human Fc in DC-SIGN-Fc ELISA. B. Lewisx expression was determined on PMN labeled for CD16 to discriminate between CD16+ neutrophils and CD16– eosinophils. C. The adhesion of beads coated with ICAM-3-Fc or DC-SIGN-Fc to PMN was assessed using flow cytometry. Specificity of adhesion was obtained using blocking anti-DC-SIGN antibodies (AZN-D1, 20 mg/ml), mannan (50 mg/ml), or EGTA (10 mM). D. Titration of DC-SIGN-Fc to PMN reveals high affinity binding of DC-SIGN to PMN. E. Binding of optimal concentration of DC-SIGN-Fc (10 mg/ml) to PMN labeled for the neutrophil marker CD16. To assess specificity blocking anti-DC-SIGN antibodies (AZN-D1, 50 mg/ml) were used.

Figure 54:
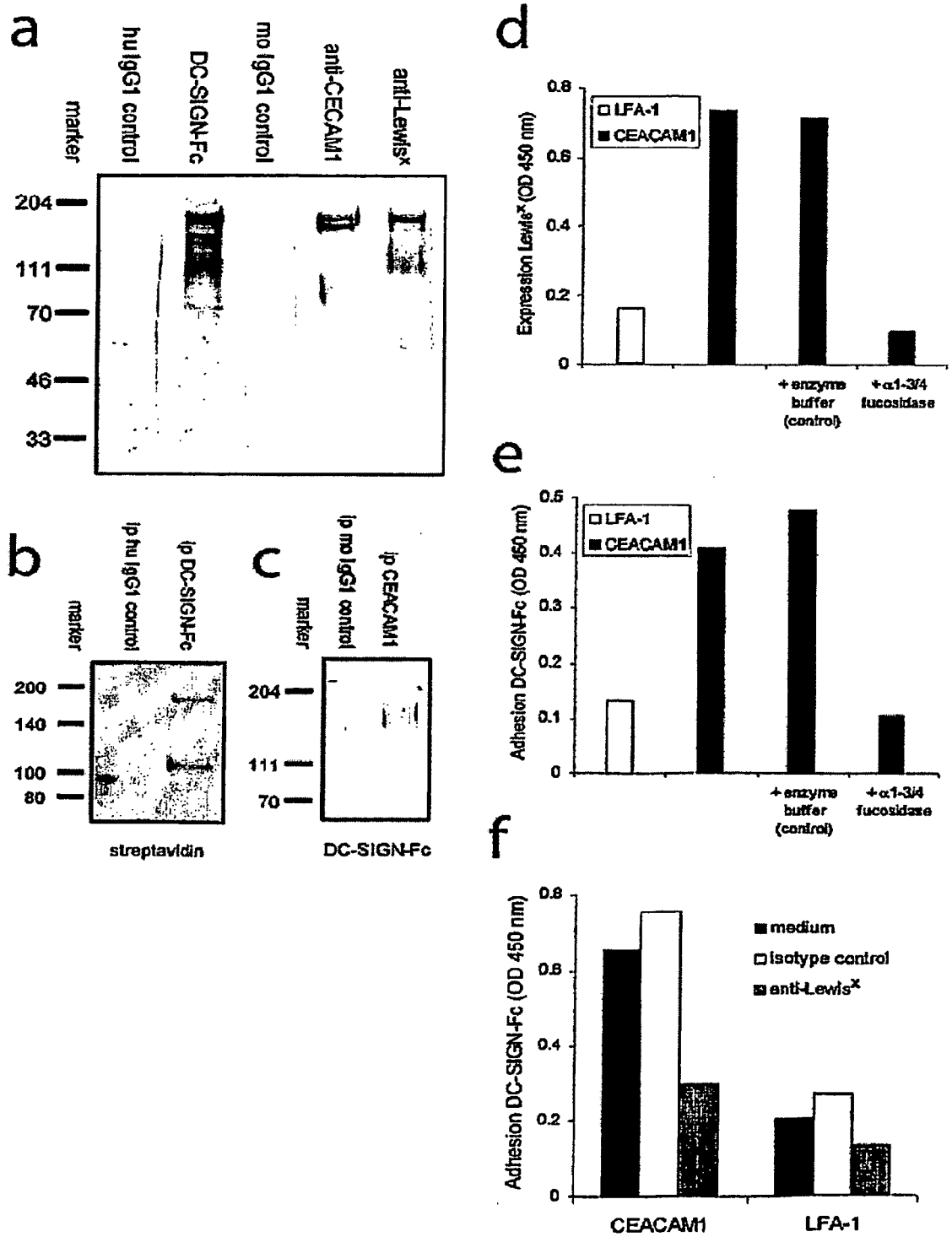

FIG. 54. CEACAM1 expressed on PMN is a ligand of DC-SIGN and binds through its Lewisx moieties. A. Whole PMN lysate was analysed on a 7% polyacrylamide gel for 1.5 hr at 120 V, transferred onto nitrocellulose blot, and stained with DC-SIGN-Fc, anti-CEACAM1 (anti-CD66) or anti-Lewisx antibodies (3 mg/ml) and alkaline phosphatase conjugated secondary antibodies. B. Protein A (protA) beads coated with DC-SIGN-Fc were used to immunoprecipitate DC-SIGN ligands from surface-biotinylated PMN. Immunoprecipitates were run on gel, transferred onto blot, and stained with peroxidase-conjugated streptavidin. C. CEACAM1 immunoprecipitated from PMN using protein G (protG) beads coated with anti-CEACAM1 antibodies was stained on blot using DC-SIGN-Fc and alkaline phosphatase conjugated goat anti-human antibodies. D. Incubation with the enzyme α1-3,4 fucosidase (5 mU/ml) for 3 days at 37° C. removes Lewisx epitope on PMN-derived CEACAM1. E. Using an ELISA-based system the adhesion of DC-SIGN-Fc to PMN CEACAM1 was measured and compared to that after treatment with α1-3,4 fucosidase. F. Antibodies directed against Lewisx (20 mg/ml) block the adhesion of DC-SIGN-Fc to CEACAM1 captured from PMN using anti-CEACAM1 antibody in adhesion ELISA.

FIG. 55. Cellular DC-SIGN expressed on K562 transfectants and immature DC binds native CEACAM1 from PMN. A. Fluorescent beads coated with PMN CEACAM1 were incubated with K562 transfectants expressing wildtype DC-SIGN or mutant DC-SIGN displaying a single amino acid substitution in the C-type lectin domain crucial for ligand binding. Bead adhesion was measured using FACS analysis. B. Adhesion of CEACAM1 coated beads to immature DC was determined. Specificity of adhesion was assessed using blocking anti-DC-SIGN antibodies (20 mg/ml), mannan (50 mg/ml), or EGTA (10 mM).

FIG. 56. DC-SIGN is involved in clustering of DC and PMN. A. CFSE-labeled PMN (green) were incubated with fluorescent HE-labeled K562, K562-DC-SIGN, and immature DC (red) for 15 min at 37° C. Anti-DC-SIGN antibodies (AZN-D1 and AZN-D2, 10 mg/ml) were used to determine involvement of DC-SIGN. Cell clustering was visualized using fluorescence microscopy and representative pictures were taken. B. Using FACS analysis cell clustering was followed in time by scoring the percentage of K562 or K562-DC-SIGN that have bound PMN. C. Adhesion of PMN to immature DC was quantified by flow cytometry.

Figure 57:
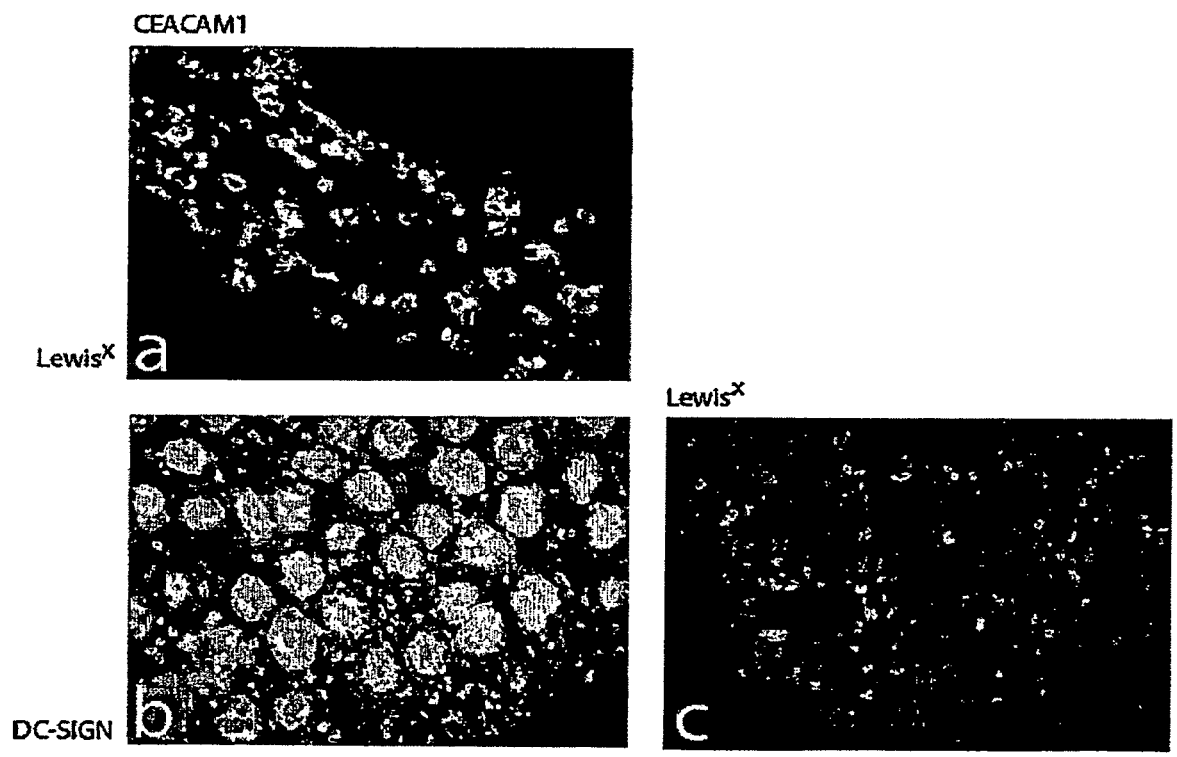
Figure 60:

FIG. 57. Localization of PMN and DC in colonic mucosa of patients with Crohn's disease. A. Slides of inflammatory intestinal tissue of patients with Crohn's disease were double stained for the PMN markers Lewisx (6H3, green fluorescence) and CEACAM1 (CLB-gran/10, blue fluorescence), B. for CEACAM1 (CLB-gran/10, green fluorescence) and the DC marker DC-SIGN (CSRD, red fluorescence), or C. for Lewisx (6H3, green fluorescence) and DC-SIGN (CSRD, red fluorescence). The anti-CEACAM1 antibody produces background staining in crypts of the colon, probably due to cross-reaction with CEA that is expressed on colonic epithelial cells.

FIG. 58. PMN activate immature DCs through DC-SIGN binding. A. Maturation of DC by resting PMN was determined measuring the expression of the DC maturation marker CD86. The maturation can be inhibited with anti-DC-SIGN antibodies (AZN-D1). The DC maturation by PMNs was compared with the maturation of DCs with LPS or E.coli. B. Cytokine production of IL-12 and TNFa was analysed upon PMN DC interaction, and is dependent on DC-SIGN binding since antibodies against DC-SIGN block the induction of cytokines.

FIG. 59. DC-SIGN binds both Lewis X-expressing CD11b and CD66a-d on PMN.

A Capture of CD11b and CD66acd from PMN lysate using specific antibodies revealed the presence of Lewis X antigens on these cell membrane molecules B Capture of CD11b and CD66acd from PMN lysate and coupling to fluorescents beads revealed that in particular PMN-derived CD11b and CD66acd interacted strongly with DC-SIGN expressing transfectants indicating that DC-SIGN binds PMN derived CD11b and CD66acd.

C Captured CD11b/CD18 and CD66 out of PMN lysate demonstrates high affinity binding with DC-SIGNFc as demonstrated in DC-SIGN Fc ELISA.

D. Immunoblotting studies demonstrate that DC-SIGNFc specifically interacts with CD66acd and CD11b from PMN when immunoprecipitated (IP) using anti-CD66acd (lane 9) and CD11b mAbs (lane 10) out of a PMN lysate. Cell-surface proteins are biotinylated and PMNs are lysed. Lane 1. negative control using ICAM-3 Fc to capture by IP proteins. Detection is peroxidase-labeled streptavidin. Lane 2. DC-SIGN-Fc is used to capture ligands biotinylated ligands from lysate; two protein bands are visible, the upper band consists of CD11b and CD66a, whereas the lower consists of CD18. Lane 3. Negative control; no bands are immune precipitated with anti-DC-SIGN antibodies. Lane 4, IP with antibodies against CD66acd; a faint band is visible containing CD66a. Lane 5, IP of CD11b; two bands are visible; the upper band is CD11c and the lower band is CD18m, which is co-immuneprecipitated with CD11c. Lane 6. IP with DC-SIGN ligands and detection with anti-CD66acd; CD66a is captured by DC-SIGN Fc. Lane 7. IP with DC-SIGN ligands and detection with anti-CD11b; CD11b is captured by DC-SIGN Fc. Lane 8. Negative control, IP with anti-DC-SIGN antibodies and detection with DC-SIGN-Fc. Lane 9. IP with anti-CD66acd and detection with DC-SIGN Fc; CD66a is bound by DC-SIGN on blot. Lane 10. IP with anti-CD11a and detection with DC-SIGN Fc; CD11a is bound by DC-SIGN on blot.

FIG. 60

DC-SIGN binds Lewis X structures on CD11b form PMN. Immunoprecipitation (IP) studies revealed that binding of DC-SIGN-Fc to CD11b is abrogated when CD11b is treated with α-1,3,4 Fucosidase that removes the fucose residue present in Lewis X (Lane 7 and 8)

FIG. 61

DC-SIGN binds tumor cells that express tumor antigen CEA (CD66e), through the interaction of DC-SIGN with CD66e.

A. DC-SIGNFc recognizes tumor antigens on several breast carcinomas and adenocarcinomas. Binding can be blocked by anti-DC-SIGN mAbs B. the tumor cell line SW948 interacts with DC-SIGN expressing cells and with DCs and the cell adhesion can be blocked by anti-DC-SIGN antibodies (AZN-D1), indicating a function for DC-SIGN to interact with a cellular structure on tumor cells C. DC-SIGN-FC binds immuneprecipitated CD66e (CEA). Immunoprecipitation with anti-CD66e (anti-CEA) of cell-surface biotinylated SW948 tumor cell-lysate shows that DC-SIGN-FC binds the tumor antigen CEA (lane 5).

FIG. 62

DC-SIGN recognizes Lewis X and Lewis Y on CD66e from tumor cells.

A. CD66e from the tumor cell line SW948 expresses Lewis X and Lewis Y carbohydrate structures s determined using specific antibodies.

B. Captured CD66e from SW948 lysate is bound by DC-SIGN-Fc

C. DC-SIGN-FC captures CD66e from a SW948 lysate as detected by an anti-CD66e specific antibody.

D. Immunoprecipitation (IP) studies revealed that binding of DC-SIGN-Fc to CD66e is abrogated when CD66e is treated with a-1,3,4 Fucosidase that removes the fucose residue present in Lewis X,Y (Lane 3 and 4).

FIG. 63.

Schematic picture of different mutants of Neisseria Meningitidis with different end-standing carbohydrate residues on their LPS structures.

Figure 64:
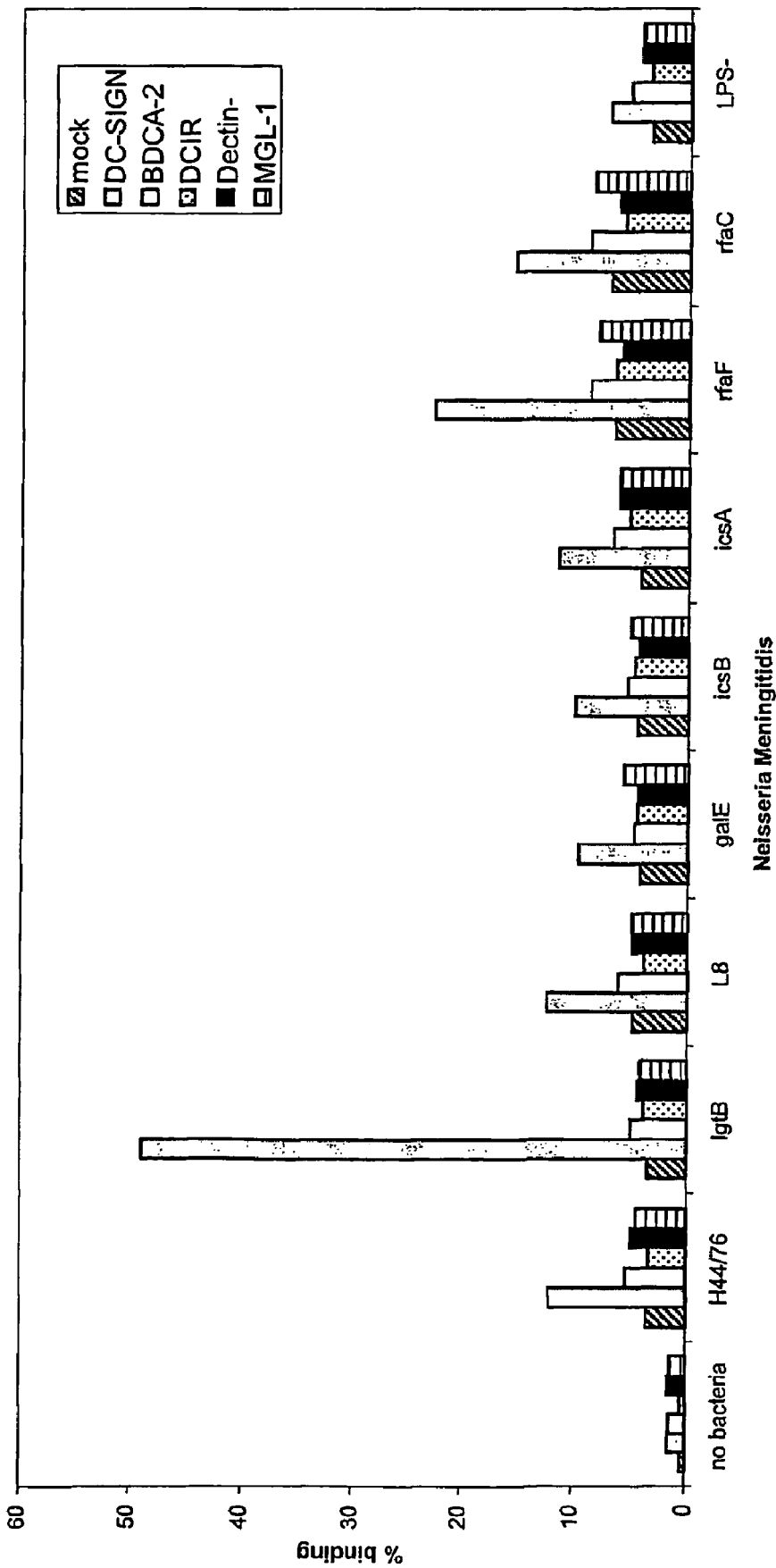

FIG. 64. DC-SIGN binds to the IgtB and rfaF mutants of Neisseria Meningitidis. The different Neisseria Meningitidis mutants are investigated for their interaction using different C-type lectin-Fc molecules (DC-SIGN-Fc, DCIR-FC, BCDA-2-Fc, MGL-Fc Dectin-1B-Fc) using the Fc ELISA assay.

Figure 65:
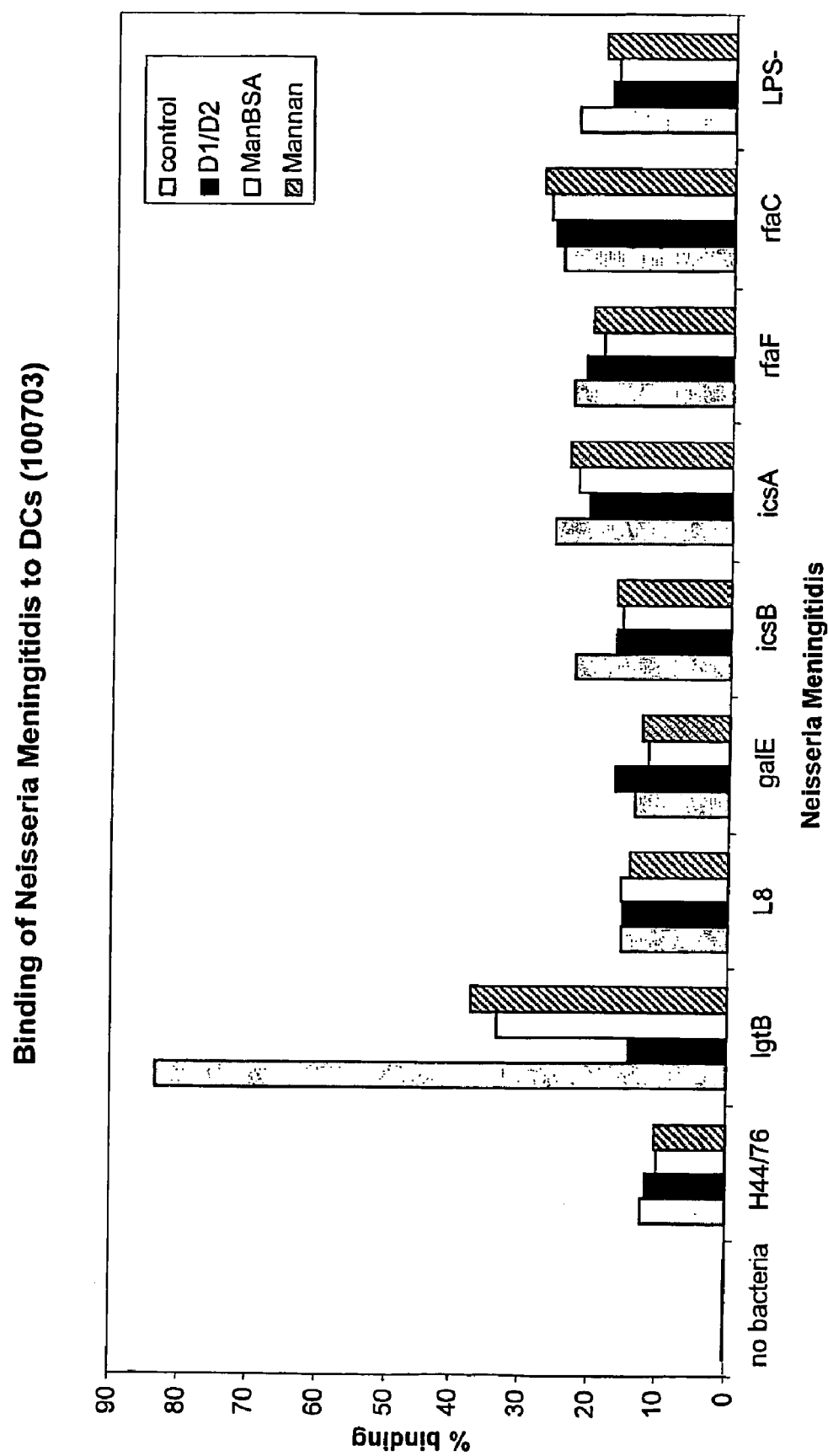

FIG. 65 Immature DCs bind strongly to the IgtB Neisseria Meningitidis mutant through DC-SIGN. Only the fluorescent mutant Neisseria IgtB, that contains an endstanding GlcNAc, binds strongly to DC, as determined by flow-cytometry, and the binding can be completely blocked by anti-DC-SIGN antibodies indicating that DC-SIGN in involved in capture Neisseria of IgtB. Mannose-BSA and mannan partly inhibit the interaction.

Figure 66:
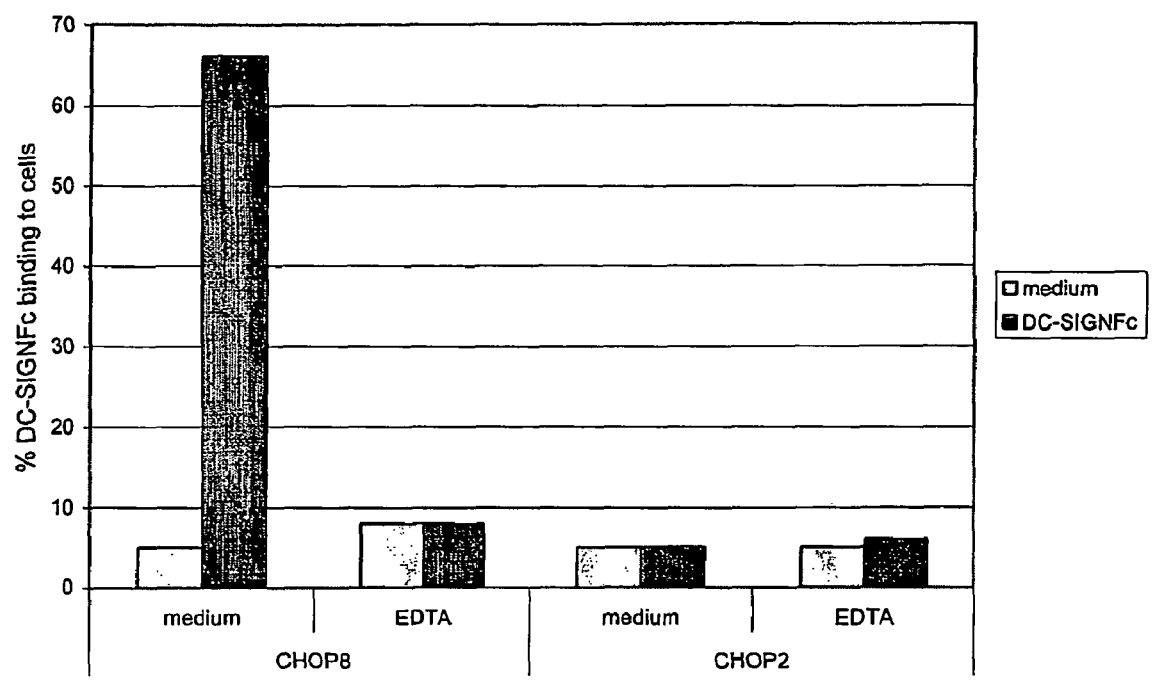

FIG. 66. DC-SIGN-Fc strongly binds CHOP8 cells that overexpress GlcNAc, indicating that DC-SIGN also binds GlcNAc residues on self-glycoproteins (CHOP8) and on pathogens such as Neisseria (FIG. 33).

EXAMPLES

Methods.

Antibodies and proteins. The following monoclonal antibodies (Mab) were used: anti-CD107a (Lamp-1; MabH4A3, BD Pharmingen), anti-MR (Clone 19, BD Pharmingen), CD11b (bear-1)[25], CD11c (SHCL3)[26], anti-DC-SIGN (AZN-D1, AZN-D2[14], CSRD[10], blocking CD11a (NKI-L15), anti-ICAM-1 (Rek-1), anti-ICAM-2 (12A2), and anti-ICAM-3 (AZN-IC3/1, icr-2), activating CD18 (KIM185) and the PE/FITC-conjugated antibodies CD25, CD69, CD80, CD86, HLA-DR (BD Pharmingen), and CD83 and CD56 (Beckman Coulter). Biotin-conjugated CD3 and CD16 (BD Pharmingen). CLB-T4 (αCD4) was a kind gift of René van Lier. MEM-157 (αCD16) and MEM-97 (αCD20) were kindly provided by Vaclav Horejsi. ICAM-1 mAb CBR-IC-1/3, ICAM-2 mAb CBR-IC-2/1, and ICAM-3 mAb CBR-IC-3/2 were obtained through the Human Leukocyte Differentiation Antigen Workshop. Several anti-glycan monoclonal antibodies (MAbs) were used: the anti-LDN-DF MAb 114-5B1-A[16], the anti-LDN MAb SMLDN1.1[17], the anti-LDN-F MAb SMLDNF1[10] and the anti-Le$^x$ MAb CB10[27], the anti-Lex mAbs SMLDN1.1 and SMFG4.1 and 6H3 (anti-Lex). The mAb (CLB-gran/10) was used to stain and immunoprecipitate CD16.

The neoglycoprotein HSA-Le$^x$, containing approx. 20-25 oligosaccharide chains per HSA molecule, was from Isosep AB, Tullinge, Sweden. The neoglycoprotein BSA-LDN-DF (approx. 12 oligosaccharide chains per molecule BSA), and BSA-LDN-F (approx. 3-4 oligosaccharides per molecule BSA), were synthesized enzymatically as described by van Remoortere et al[16], and Nyame et al[17], respectively. Le$^x$-PAA-biotin, containing Le$^x$ multivalently coupled to biotinylated polyacrylamide was from Syntesome, Munich, Germany.

Mannan purified from *Saccheromyces cerevisiae* (50 µg/ml) and recombinant gp120 (0.50 µg/ml) were obtained from Sigma and the Aids Resource Foundation, respectively. Purified mannose capped lipoarabinomannan (manLAM) from *Mycobacterium tuberculosis*, and non-capped LAM (araLAM) from *M. smegmatis* were kindly provided by Dr. J. Belisle, Colorado State University through NIH, NIAID contract NO1 AI-75320. Soluble egg antigen (SEA) was kindly provided by Dr. A. K. Nyame, Oklahoma University HSC, USA). Purified lipophosphoglycan from *Leishmania mexicana* was kindly donated by Dr. M Wiese, Bernard Nocht Inst. Tropical Medicine Hamburg, Germany. Purified lipopolysaccharide of *Helicobacter pylori* was obtained from M. Monteiro, NRC, Ottawa, Canada. A sonicate of bacterial cells of a clinical isolate of *M. tuberculosis* was donated by A. Kolk, KIT, Royal Trop. Inst, Amsterdam. Clinical isolates of *Helicobacter pylori*, *Escherichia coli*, *Klebsiella pneumoniae*, *Pseudomonas aeruginosa* and *Staphylococcus aureus* were obtained from VUMC Hospital, Amsterdam. Synthetic glycoconjugates were obtained from Syntesome, Munich, Germany, and comprise mono- and oligosaccharides multivalently linked to a biotinylated polyacrylamide carrier, MW 40.000.

Soluble DC-SIGN-Fc adhesion assay. DC-SIGN-Fc consists of the extracellular portion of DC-SIGN (amino acid residues 64-404) fused at the C-terminus to a human IgG1-Fc fragment. DC-SIGN-Fc was produced in Chinese Hamster Ovary K1 cells by co-transfection of DC-SIGN-Sig-pIgG1 Fc (20 µg) and pEE14 (5 µg) vector. DC-SIGN-Fc concentrations in the supernatant were determined by an anti-IgG1 Fc ELISA. The DC-SIGN-Fc binding assay was performed as follows. Glycoconjugates and sonicated mycobacteria were coated onto ELISA plates at 5 µg/well; intact bacterial cells were coated at 5×10$^7$/ml; coating took place for 18 hours at room temperature, followed by blocking with 1% BSA for 30 min, at 37° C. in TSM (20 mM Tris-HCl pH 7.4 containing 150 mM NaCl, 2 mM CaCl$_2$ and 2 mM MgCl$_2$). Soluble DC-SIGN-Fc (approx. 2 µg/ml in TSM buffer) was added and the adhesion was performed for 120 min. at RT. Unbound DC-SIGN-Fc was washed away and binding was determined by an anti-IgG1 Fc ELISA using a peroxidase conjugate of goat anti-human Fc. Specificity was determined in the presence of either 20 µg/ml blocking antibodies, 50 µg/ml mannan or 5 mM EGTA.

Cells. Immature DC were cultured from monocytes in the presence of IL-4 and GM-CSF (500 and 800 U/ml, respectively; Schering-Plough, Brussels, Belgium[28]. At day 7 the phenotype of the cultured DC was confirmed by flow cytometric analysis. The DC expressed high levels of MHC class I and II, αMβ2 (CD11b), αXβ2 (CD11c) and ICAM-1, moderate levels of LFA-1 and CD80, and low levels of CD14. K562 transfectants expressing wild-type DC-SIGN were generated by transfection of K562 cells with 10 µg pRc/CMV-DC-SIGN plasmid by electroporation as previously described.

Stable transfectants of K562 expressing ICAM-3 were obtained by electroporation of pCDM8-ICAM-3 and pGK-HYG. K562 cells were cultured on RPMI 10% FCS, whereas K562-ICAM-3 cells were cultured on RPMI 10% FCS: Iscove's 5% FCS 3:1 containing 0.5 mg/ml hygromycine to maintain ICAM-3 expression.

Naive NK cells were isolated from buffy coats of healthy donors. Briefly, the PBMC fraction obtained through Ficoll centrifugation was sequentially depleted for CD14+ cells, and CD3+, CD4+, and CD20+ cells using MACS sorting. CD14+ cells were depleted by CD14 microbeads (Miltenyi Biotec) on an LS column (Miltenyi Biotec), and CD3+, CD4+, and CD20+ cells were labeled by the mAbs T3B (αCD3), CLB-T4 (αCD4), MEM97 (αCD20), and thereafter depleted by goat-α-mouse microbeads (Miltenyi Biotec) on an LD column (Miltenyi Biotec). Thus obtained NK cells were routinely tested for the NK cell markers CD16 (75% to 90% expression), CD56 (80 to 95% expression), the non-lineage markers CD3, CD4, CD14 and CD20 (all less than 1% expression), and the early activation marker CD69 (15% expression on non-activated NK cells and 75% expression on 1-day IL-2-activated NK cells). CD56$^{dim}$ and CD56$^{bright}$ NK cell populations were isolated from MACS obtained NK cells by FACS sorting on low and high CD56 expression, respectively. CD56$^{dim}$ and CD56$^{bright}$ NK cell populations were over 95% pure as assessed by flow cytometry staining for CD16 and CD56.

DC activation. Immature DC (2×10$^6$ cells/ml) were cultured for 24 hours in the presence of IL-4 (500 U/ml, Schering-Plough, Brussels, Belgium), GM-CSF (800 U/m; Schering-Plough, Brussels, Belgium) and either LPS (10 ng/ml) or LAM glycolipids (15 µg/ml). The effect of LAM on LPS-induced activation was determined by pre-incubating immature DC (300.000 cells) with AZN-D2 (40 µg/ml) for 30 minutes, and subsequently with LPS in the presence of LAM (15 µg/ml) for 18 hours. LAM glycolipids were obtained from J. Belisle (Colorado State University and the NIH (contract NO1 AI-75320)) and contained <5 ng/mg endotoxin. Activation was determined by cell-surface expression of MHC class II (HLA-DR) and the co-stimulatory molecules CD80, CD83 and CD86 using PE-conjugated antibodies.

Fluorescent bead adhesion assay. Carboxylate-modified TransFluorSpheres (488/645 nm, 1.0 µm; Molecular Probes, Eugene, Oreg.) were coated with HIV-1 gp120 and ICAM-3 as described[14]. Streptavidin was covalently coupled to the beads as described and streptavidin-coated beads were incubated with biotinylated PAA-linked glycoconjugates (50 pMol; Syntesome, Munich, Germany). The fluorescent bead adhesion assay was performed as described[14]. Ligand-coated fluorescent beads (20 beads/cell) were added to the cells for 45 minutes at 37° C., washed and analyzed by flow cytometry (FACScan, Becton Dickinson, Oxnard, Calif.), by measuring the percentage of cells that had bound fluorescent beads. LAM-coated beads were generated by coating incubating streptavidin-coated beads were incubated with biotinylated F(ab')2 fragment goat anti-mouse IgG (6 µg/ml; Jackson Immunoresearch) followed by an overnight incubation with mouse-anti-LAM antibody (F30.5) at 4° C. The beads were washed and incubated with 250 ng/ml purified glycolipid LAM (obtained from J. Belisle, Colorado State University and the NIH (contract NO1 AI-75320)) overnight at 4° C. SEA-coated beads were generated by incubating the streptavidin-coated beads with biotinylated F(ab')2 fragment of goat anti-mouse IgG (6 µg/ml; Jackson Immunoresearch), followed by an overnight incubation at 4° C. with anti-LDN MAb, or anti-LDN-DF MAb. The beads were washed and incubated with 1 µg/ml SEA overnight at 4° C. Essentially, $50\times10^3$ cells were pre-incubated in adhesion buffer (20 mM Tris-HCl pH 8.0, 150 mM NaCl, 1 mM CaCl2, 2 mM MgCl2, 0.5% BSA) with or without blocking MAbs (20 µg/ml) or mannan (50 µg/ml) for 10 minutes at room temperature. Ligand-coated fluorescent beads (20 beads/cell) were added to the cells and the suspension was incubated for 45 minutes at 37° C. Cells were washed and adhesion was determined using flow cytometry (FACScan, Becton Dickinson, Oxnard, Calif.), by measuring the percentage of cells that had bound fluorescent beads. HIV-1 gp120 fluorescent beads were prepared as described previously[19].

DC-SIGN-Fc adhesion. Cells were incubated with DC-SIGN-Fc for 30 minutes at 37° C. under saturating conditions (concentration: 10 µg/ml), and subsequently with FITC-conjugated goat-α-human secondary antibodies to monitor adhesion of DC-SIGN-Fc. Before incubation with cells, DC-SIGN-Fc was preincubated for 10 min at RT either with medium, aDC-SIGN (AZN-D1, 50 µg/ml), mannan (50 µg/ml), or EGTA (10 mM) to determine specificity of DC-SIGN-Fc adhesion. DC-SIGN-Fc adhesion was determined by flow cytometry (FACS Calibur, Beckman Coulter).

Mycobacteria. Both the *M. bovis* BCG (Pasteur) and the *M. tuberculosis* H37Ra strains were gifts from A. Kolk (Royal Tropical Institute, Amsterdam). *M. bovis* BCG was cultured in vitro using Middelbrook 7H9 broth supplemented with 0.05% Tween 80 and albumin-dextrose-catalase. The glycolipids ManLAM and AraLAM were obtained from J. Belisle, Colorado State University and the NIH (contract NO1 AI-75320). DC were infected with mycobacteria by co-culturing them at an appropriate multiplicity of infection (MOI) as indicated in the figure legends.

Fluorescent mycobacterial binding assay. Capture and internalization of mycobacteria by cells was evaluated using fluorescein isothiocyanate (FITC)-conjugated *M. bovis* BCG. Bacteria ($10^9$/ml) were labeled by incubation of 0.5 mg FITC per ml in phosphate buffered saline (pH 7.4) at room temperature for 1 hour. The FITC-pulsed bacteria were washed three times to remove unbound FITC. Capture was determined by measuring the percentage of cells that bound FITC-conjugated bacteria using flow cytometry (FACScalibur, Becton Dickinson Immunocytometry, San Jose, Calif.). Phagocytosis was determined using a fluorescence-quenching technique as reported previously[29]. In brief, quenching of non-internalized membrane-bound FITC-conjugated *M. bovis* BCG was achieved by treating the cells with 0.05% trypan blue for 5 minutes. *H. pylori* binding was assessed by labeling the bacteria with FITC and binding to DC was investigated similarly to the bead assay.

Cytokine production. For the detection of cytokines, culture supernatants were harvested at day 1 and frozen at −80° C. until analysis. The supernatants were analyzed for the presence of IL-10 and IL-12p40 by ELISA (Biosource International, Calif.).

Defucosylation of SEA. SEA were defucosylated by incubation of the antigens at 100° C. for 1 hour in 0.1M TFA. After neutralization, the defucosylated antigen was coated to ELISA plates. Enzymatic defucosylation was performed by incubating the SEA in 50 mM sodiumphosphate pH=5.0 with a1,3/4-fucosidase (0.4 mU/µg SEA) (Calbiochem) overnight at 37° C. The degree of defucosylation of the antigens was assessed by their ability to bind MAbs specifically recognizing the fucosylated glycan epitopes LDN-DF and $Le^x$, whereas the integrity of other, non-fucosylated, glycan epitopes was assessed by measuring the reactivity with anti-LDN MAb.

SDS-PAGE, Western blotting and silver staining. SEA were separated by SDS-PAGE under reducing conditions on a 12.5% polyacrylamide gel, using the Mini-Protean II system (BioRad), and proteins visualized by silver-staining. For Western blotting proteins were transferred onto a nitrocellulose membrane (Schleicher and Schuell). The membrane was blocked in a solution of 5% BSA in TSM for 2 h followed by incubation in 2 µg/ml DC-SIGN-Fc in TSM buffer containing 1% BSA for 1 h. After washing, the membrane was subsequently incubated for 1 h in peroxidase conjugated goat anti-human IgG1 and reactive bands were visualized by detection with CN/DAB substrate (Pierce).

Cytotoxicity. The standard 4-hour $^{51}Cr$ release assay was used to assess NK cell-mediated cytotoxicity. Briefly, $1*10^6$ target cells were labeled by 100 µCi $^{51}Cr$ for 1 hour at 37° C., extensively washed to remove free $^{51}Cr$, resuspended at 2500 cells/well (iDC and mDC) or 1000 cells/well (K562 and K562-DC-SIGN), and incubated with NK cells for 4 hours at 37° C. at the indicated ratios and under the indicated conditions. After 4 hours scintillation liquid (PerkinElmer) was added to supernatants, and $^{51}Cr$ release was determined on a micro-b counter (PerkinElmer).

NK cell-mediated DC maturation. Resting and activated NK cells were obtained by overnight incubation on medium and IL-2 (1000 U/ml), respectively. Thereafter, resting and activated NK cells were incubated overnight with immature DC in a 96 wells U-bottom plate (Costar) on RPMI 10% FCS. NK cells were preincubated for 10 min. at RT with medium or blocking αLFA-1 mAbs (NKI-L15, 50 µg/ml), whereas DC were preincubated with medium or blocking αDC-SIGN mAbs (AZN-D2, 50 µg/ml). As a positive control DC were incubated overnight in the presence of LPS (2 µg/ml). Maturation of DC was assessed by flow cytometry (FACS Scan, Beckman Coulter) for the maturation markers CD80, CD83, CD86, and HLA-DR by PE-conjugated or FITC-conjugated mAbs.

DC-induced NK cell activation. Resting NK cells were incubated for 2 days with immature or mature DC (obtained by LPS maturation) in a 96 wells U-bottom plate (Costar) on RPMI 10% FCS. LFA-1-dependent DC-induced NK cell activation was determined by a 10 min. preincubation of NK cells with αLFA-1 mAbs (NKI-L15, 50 µg/ml), whereas dependency on DC-SIGN was assessed by a 10 min. preincubation of DC with anti-DC-SIGN mAbs (AZN-D1 and AZN-D2, 50 µg/ml). As a positive control NK cells were incubated for 2 days with IL-2 (1000 U/ml). NK cell activation was assessed by flow cytometry (FACS Calibur, Beckman Coulter) for the early activation marker CD69 by FITC-conjugated mAbs.

Immunoprecipitation. NK cells were surface iodinated with 1 mCi $^{125}I$, or biotinylated and subsequently lysed in lysis buffer (1% Triton-X-100, 10 mM TEA, 150 mM NaCl, 1 mM $CaCl_2$, 1 mM $MgCl_2$, 1 mM PMSF, 20 µg/ml trypsin inhibitor, 20 µg/ml leupeptin, and 20 µg/ml aprotinin). DC-SIGN ligands, ICAM-2, ICAM-3, and LFA-1 were immunoprecipitated from prot A-precleared NK, cell lysate by prot A beads covalently linked to DC-SIGN-Fc, αICAM-2 (12A2), αICAM-3 (AZN-IC-3/1), and αLFA-1 (NKI-L15). Immunoprecipitates were reduced in sample buffer (containing 4% SDS and 5% b-mercapto-ethanol), heated for 5 min at 95° C., and run on a 5-15% gradient polyacrylamide gel (SDS-PAGE).

Alternatively, specific anti-bodies against CD66acd or ICAM-3 or LFA-1 were coated in an ELISA plate, subsequently lysates were added and incubated for 1 hr at 4 C to retract the specific proteins. DC-SIGNFc was incubated for binding activity to the specific proteins and stained with Goat anti human Fc PO and developed.

Experimental Setup.

Dendritic cells (DC) are instrumental in handling pathogens for processing and presentation to T cells, thus eliciting an appropriate immune response. C-type lectins expressed by DC function as pathogen-recognition receptors; yet their specificity for carbohydrate structures on pathogens is not fully understood. Here we analyzed the carbohydrate specificity of DC-SIGN/CD209, the recently documented HIV-1 receptor on DC. Our studies show that DC-SIGN binds with high affinity to both synthetic mannose- and fucose-containing glycoconjugates. These carbohydrate structures are abundantly expressed by pathogens as demonstrated by the affinity of DC-SIGN for natural surface glycans of the human pathogens *Mycobacterium tuberculosis, Helicobacter pylori, Leishmania mexicana* and *Schistosoma mansoni*. Strikingly, these pathogens target DC-SIGN to infect DC but also to modulate the immune responses mediated by DC.

This analysis expands our knowledge on the carbohydrate and pathogen-specificity of DC-SIGN, and identifies this lectin to be central in pathogen-DC interactions.

Example 1

Novel Carbohydrate Specificity for DC-SIGN

For in vitro binding studies we generated a chimeric protein of DC-SIGN with a human IgG1 Fc tag, which we used to screen in an ELISA format for reactivity with a panel of synthetic glycoconjugates containing mannose or fucose residues and their derivatives in multimeric form.

As reported earlier, DC-SIGN-FC binds to purified yeast-derived mannan and the high mannose containing HIV-1 gp120, but also to less complex mannose-containing glycoconjugates i.e. mannose and $\alpha 1$->3, $\alpha 1$->6 mannotriose (Table I, FIG. 1). Strikingly, DC-SIGN binds to Lewis blood group antigens ($Le^x$, $Le^y$, $Le^a$, $Le^b$), glycan comprising at least one terminal fucose $\alpha 1,3$ or $\alpha 1,4$-linked to N-acetylglucosamine ($Le^x$, $Le^y$ $Le^a$, $Le^b$, LDNF), or □-1,2 to Galactose ($Le^y$, $Le^b$) (Table I, FIG. 1). Sialylation of $Le^x$ (yielding sialyl-$Le^x$, a L-, E- and P-selectin ligand) completely abrogates the recognition by DC-SIGN, indicating that DC-SIGN has a carbohydrate specificity that is distinct from that of the selectins that mediate leukocyte rolling. Sulfation reduced the binding affinity of DC-SIGN for $Le^x$, as well as $Le^a$ (FIG. 1c). To compare in more detail the affinity of DC-SIGN binding to $Le^x$ and □1>3, □1>6-mannotriose, titration studies were performed with the different DC-SIGN binding glycoconjugates (FIG. 1c). Strikingly, DC-SIGN binds with much higher affinity to the fucose-containing carbohydrate $Le^x$ than to mannotriose. The binding activity of DC-SIGN-Fc to these glycan structures was specific, since anti-DC-SIGN antibodies blocked the interaction (FIG. 1c).

To determine whether DC-SIGN-FC exhibits a similar carbohydrate recognition profile as cell-surface expressed DC-SIGN, both DC-SIGN transfectants and monocyte-derived DC were studied for carbohydrate binding activity using a fluorescent beads adhesion assay with different glycoconjugates ($\alpha 1$->3, $\alpha 1$->6mannotriose, $Le^x$ and sulfo-$Le^a$) (FIG. 2). Indeed, DC-SIGN expressed by K562 transfectants bound similarly to the glycoconjugates as DC-SIGN-Fc and the binding was completely inhibited by anti-DC-SIGN antibodies (FIG. 2). Even though DC express many other C-type lectins on their cell surface, our data demonstrate that the glycoconjugates containing $Le^x$ and $\alpha 1$->3, $\alpha 1$->6mannotri- ose are preferentially bound by DC-SIGN. The interaction is specific since anti-DC-SIGN antibodies almost completely inhibited the binding activity. This illustrates that DC-SIGN is the major receptor on DC for these carbohydrate structures. Binding of sulfo-$Le^a$ to DC could only be partially blocked by anti-DC-SIGN antibodies indicating that other C-type lectins on DC compete with DC-SIGN for binding of sulfo-$Le^a$. Our data show that DC-SIGN recognizes a wider range of glycan structures, including Lewis blood group antigens, than hitherto realized. Thus, DC-SIGN may be an important receptor for recognition of novel biologically relevant targets expressed by the host, or alternatively by human pathogens.

Example 2

Figure 3A:
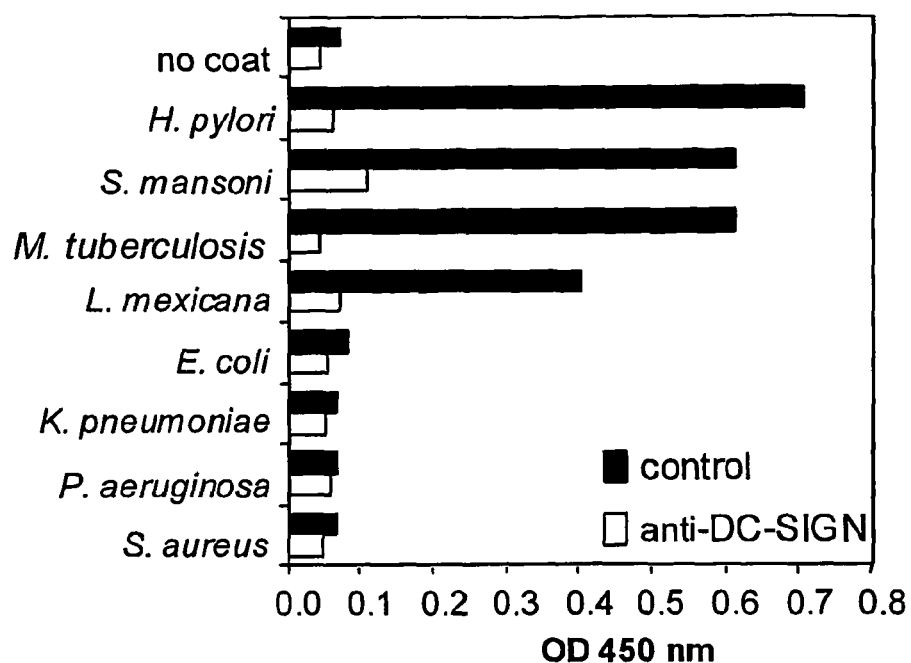
FIG. 3. DC-SIGN binds four novel pathogens
a. Pathogens that consist out of $Le^x$-rich *Helicobacter pylori* and *Schistosoma Mansoni*, and mannose-capped lipoarabinanomannan (manLAM) of *Mycobacterium tuberculosis* and mannose-capped lipophosphoglycan of *Leishmania mexicana*, *Escherichia coli*, *Klebsiella pneumoniae*, *Pseudomonas aeruginosa* and *Staphylococcus aureus* were coated and binding of recombinant DC-SIGN-Fc was measured as with peroxidase-labeled goat-anti-human Fc.
b. DC-SIGN can bind LPS of *Klebsiella* Len1 that contains mannose cap, but does not bind the LPS of *Klebsiella* Len 111 that lack a mannose cap indicating that strains that contain the DC-SIGN binding carbohydrates interact with DC-SIGN on Dendritic cells or DC-SIGN transfectants.
Figure 3B:
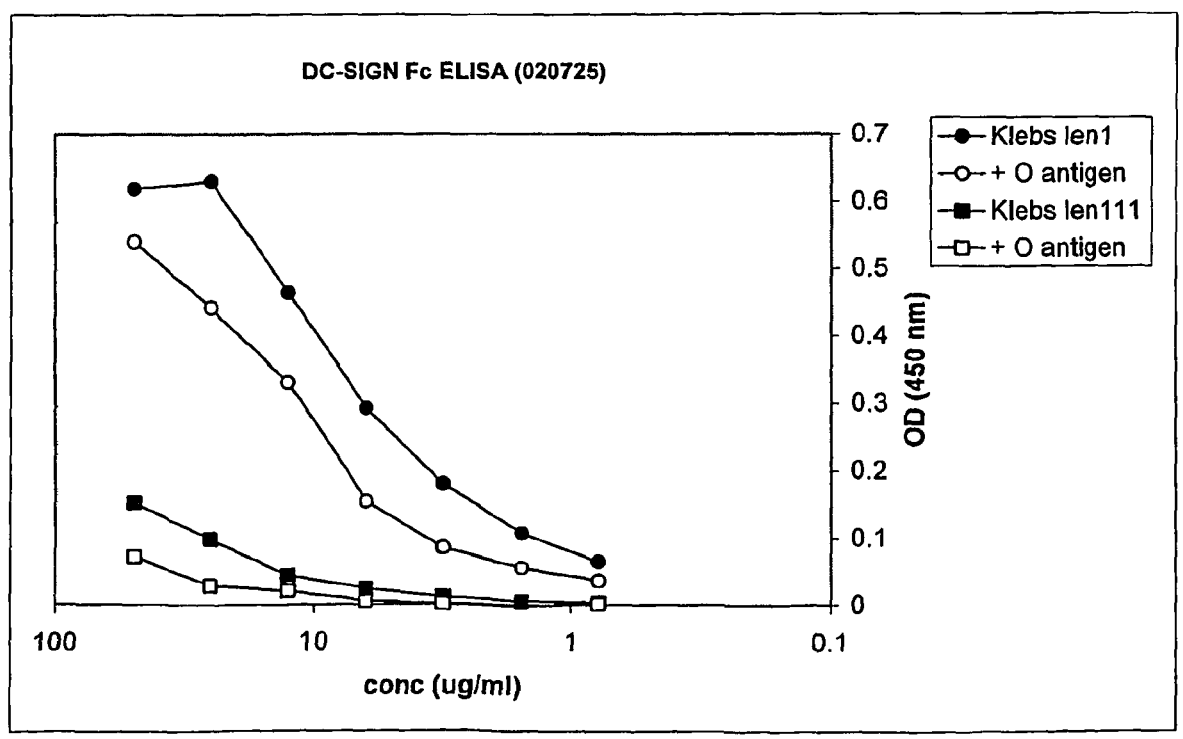
Figure 4:
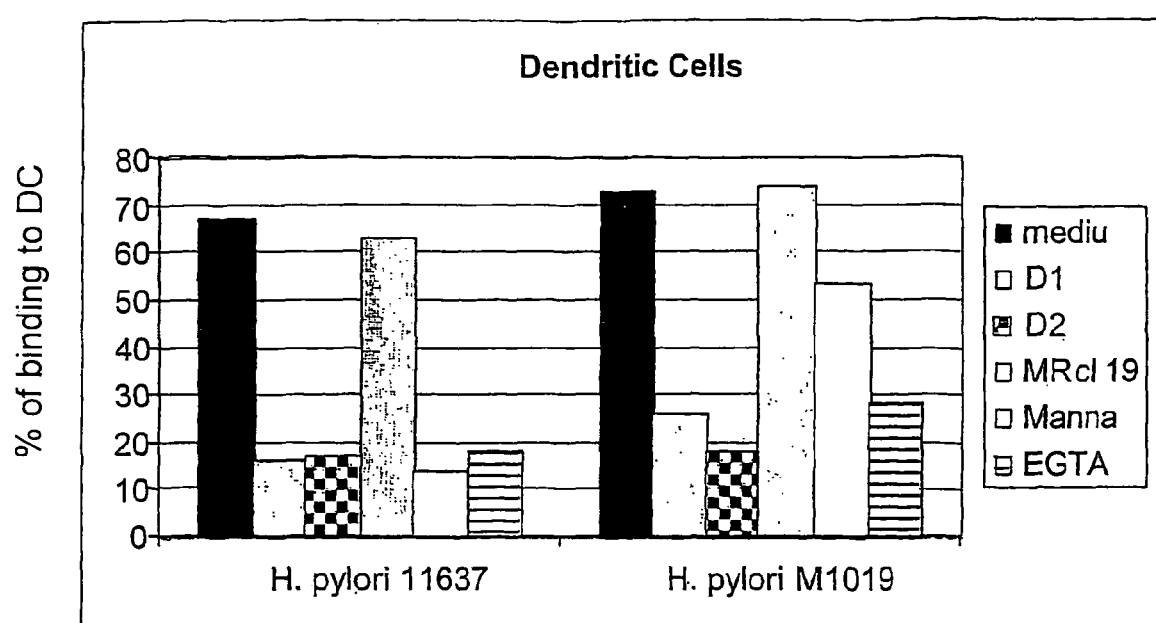
FIG. 4. DC strongly interact with *H. pylori* LPS through DC-SIGN. Biotinylated LPS (strains 11637 and M1019) was coated on streptavidin beads and the adhesion to DC was determined with the fluorescent bead adhesion assay. Specificity was determined by using antibodies against DC-SIGN and the mannose receptor. Moreover, adhesion was determined in the presence of mannan and EGTA.

Novel Carbohydrate Specificity ($Le^x$ and High Mannose) Identifies Novel Pathogens (*Helicobacter pylori, Schistosoma mansoni, Mycobacterium tuberculosis, Leishmania mexicana*) that Interact with DC-SIGN We subsequently investigated the binding of DC-SIGN to human pathogens that express mannose- or fucose-containing glycans. The gram-negative *Helicobacter pylori* bacterium, which induces peptic ulcers and gastric carcinoma[20], and the worm parasite (the causal agent of schistosomiasis) both express $Le^x$ [21]. In *H. pylori*, $Le^x$ is present on surface-located lipopolysaccharide, while in *S. mansoni* $Le^x$ is expressed by all stages of the parasite, including soluble egg antigen (SEA)[21]. Binding of DC-SIGN-Fc to $Le^x$-positive *H. pylori* lysate and to extract of *S. mansoni* was strong and was completely inhibited by anti-DC-SIGN antibodies (FIG. 3); When analysisng two different LPS forms from *Klebsiella* one containing mannose cap and one without (Len1 and Len1ll respectively) (FIG. 3B). DC-SIGN expressed by DC also bound to purified LPS of *H. pylori* (FIG. 4). Binding of DC to both *H. pylori* cells and purified LPS could be completely blocked with anti-DC-SIGN Mab (FIG. 4). Also glycans present in *Mycobacterium tuberculosis*, the causative agent of tuberculosis, are bound by DC-SIGN (FIG. 3). The mannose-capped surface glycan, lipoarabinomannan of *Mycobacterium tuberculosis* probably contains the recognition site for DC-SIGN. This is further supported by the fact that DC-SIGN also bound to the mannose-capped surface lipophosphoglycan (LPG) expressed by an unicellular parasite that causes leishmaniasis (FIG. 3). Binding of DC-SIGN to *Leishmania* was reported very recently[30] but we demonstrate here that LPG is the structure on *Leishmania* that is recognized by DC-SIGN (FIG. 3). No binding of DC-SIGN to three clinically relevant Gram-negative bacterial human pathogens (*Escherichia coli, Klebsiella pneumoniae* and *Pseudomonas aeruginosa*) was observed nor to Gram-positive *Staphylococcus aureus*. However other clinical isolates of *Klebsiella* that contain a mannose capped LPS bind DC-SIGN. These findings indicate that binding of DC-SIGN to pathogens is selective, and that the carbohydrate specificity of DC-SIGN governs a broader pathogen recognition than only viruses such as HIV-1 and Ebola virus[12,22].

Example 3

DC-SIGN Interacts with *M. tuberculosis* through ManLAM Glycolipids

Whole mycobacteria such as the *M. tuberculosis* H37Ra strain and *M. bovis bacillus* Calmette-Guérin (BCG) were coated and the interaction of DC-SIGN with these pathogens was analyzed using the DC-SIGN-Fc binding assay. *M. bovis* BCG is a tuberculosis strain that is almost nonpathogenic yet retains the immunological properties of tuberculosis. DC-SIGN-Fc interacted specifically with both *M. tuberculosis* H37Ra and *M. bovis* BCG, since the interaction was inhibited with blocking DC-SIGN-specific antibodies (FIG. 6a). *M. smegmatis*, an avirulent strain that does not contain a Mannose cap, did not bind DC-SIGN (data not shown).

Figure 6:
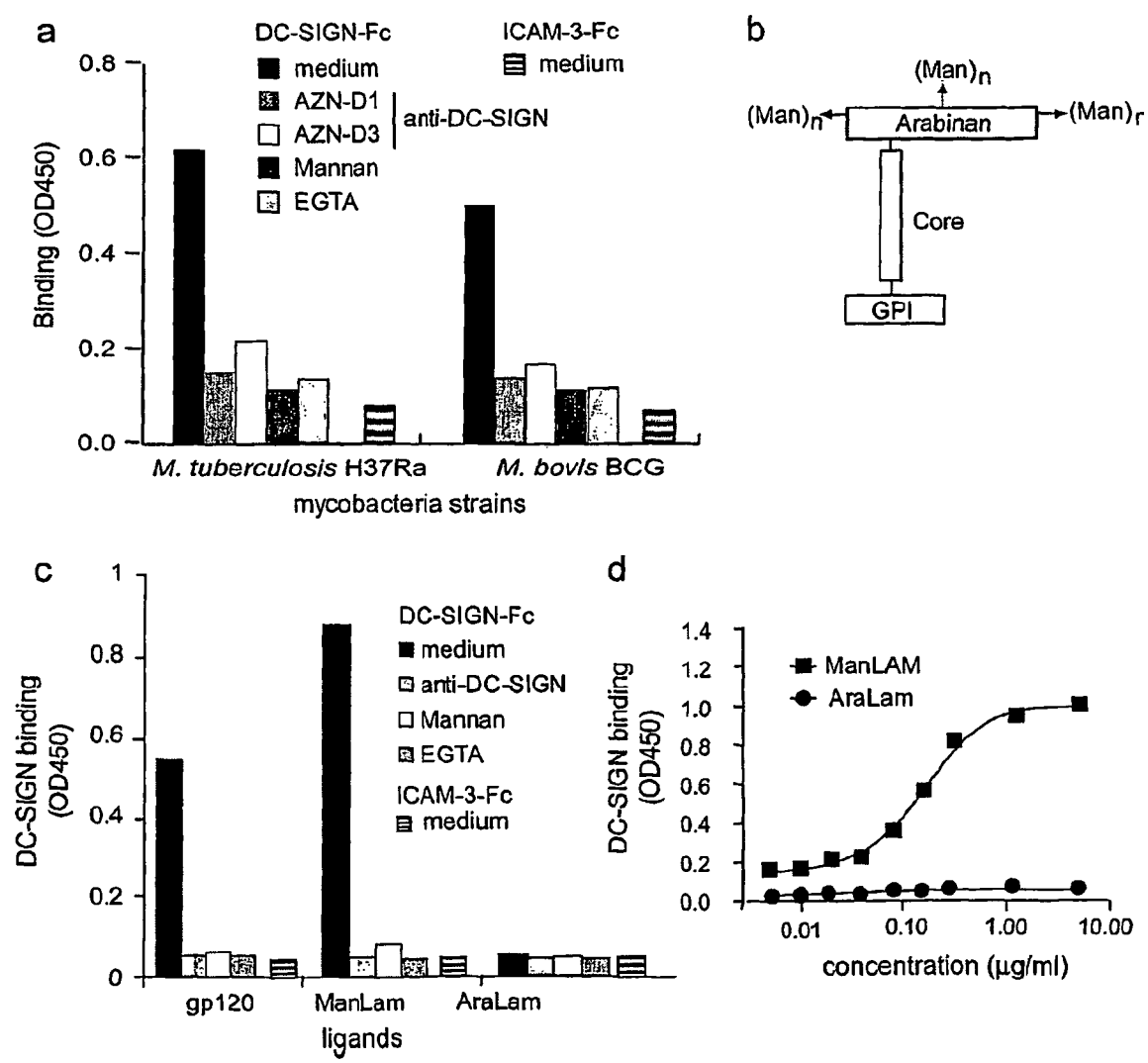
FIG. 6. DC-SIGN specifically binds ManLAM, a cell-wall component of *M. tuberculosis*.
a) DC-SIGN interacts with several mycobacteria strains. DC-SIGN-Fc binding to mycobacteria ($5*10^5$ bacteria) was determined by a Fc-specific ELISA. Specificity was determined by measuring binding in the presence of blocking DC-SIGN-specific antibodies (AZN-D1 or AZN-D3) and mannan. EGTA was used to determine the calcium-dependency of the DC-SIGN-Fc-mediated binding. ICAM-3-Fc binding to mycobacteria was also measured to exclude non-specific binding by the Fc domain. Standard deviation<0.02 OD450. One representative experiment out of three is shown. Binding of *Mycobacterium Smegmatis* that lacks the ManLAM structure does not interact with DC-SIGN (data not shown).
b) The schematic structure of ManLAM. Lipoarabinomannan (LAM) of *M. tuberculosis* consists of a glycosylphosphatidyl anchor (GPI), an mannose-rich oligosaccharide core and a branched arabinose polymer that ends in mannose-caps (n=0-3). AraLAM has a similar structure but does not contain the mannose-cap (ref).
c) The mannosylated-lipoarabinomannan ManLAM, in contrast to the non-mannosylatd AraLAM, is specifically bound by DC-SIGN. The anti-DC-SIGN antibody AZN-D1 was used to determine specificity. The DC-SIGN-Fc binding assay was performed as described in FIG. 1a. Standard deviation<0.02 OD450. One representative experiment out of three is shown.
d) DC-SIGN does not interact with AraLAM. The DC-SIGN-Fc binding assay was performed as described in FIG. 1a. One representative experiment out of three is shown.

Moreover, an irrelevant Fc chimera, ICAM-3-Fc, did not interact with the mycobacteria (FIG. 6a). The interaction is mediated by the C-type lectin domain of DC-SIGN, since binding to both *M. tuberculosis* and *M. bovis* BCG was inhibited by EGTA, mannan and the DC-SIGN-specific antibody AZN-D1 that recognizes the lectin domain[23] (FIG. 6a).

We next investigated the binding of DC-SIGN to purified mycobacterial lipoarabinomannan (LAW, since DC-SIGN has a high affinity for mannose-containing carbohydrates and LAM is the major mannose-containing component of the mycobacterial cell-wall[31]. LAM comprises a mannose-rich polysaccharide-core, containing highly branched arabinofuranosyl side chains, and a GPI anchor (FIG. 6b). LAM isolated from *M. tuberculosis* contains mannose-residues consisting exclusively of mono-, di- and trimers of □-D-mannoses directly linked to the arabinofuranosyl-termini and is called ManLAM, whereas LAM isolated from the fast growing *M. smegmatis* is not mannose-capped and is called AraLAM[31] (FIG. 6b). Strikingly, purified ManLAM was efficiently bound by DC-SIGN, in contrast to AraLAM (FIG. 6c), demonstrating that DC-SIGN specifically interacts with the mono-, di- and trimers of α-D-mannoses of ManLAM. Even at high concentrations, DC-SIGN did not bind AraLAM, demonstrating a high specificity for ManLAM and its mannose-cap (FIG. 6d). The interaction of DC-SIGN to ManLAM is specific, since the binding was inhibited by antibodies against DC-SIGN, whereas an irrelevant Fc chimera did not interact with ManLAM (FIG. 6c). DC-SIGN interacts similarly with both ManLAM and whole *M. bovis* BCG indicating that DC-SIGN binds mycobacteria through ManLAM (FIG. 6a and c).

Example 4

Both mycobacteria and ManLAM interact with the primary binding site of DC-SIGN

Figure 7:
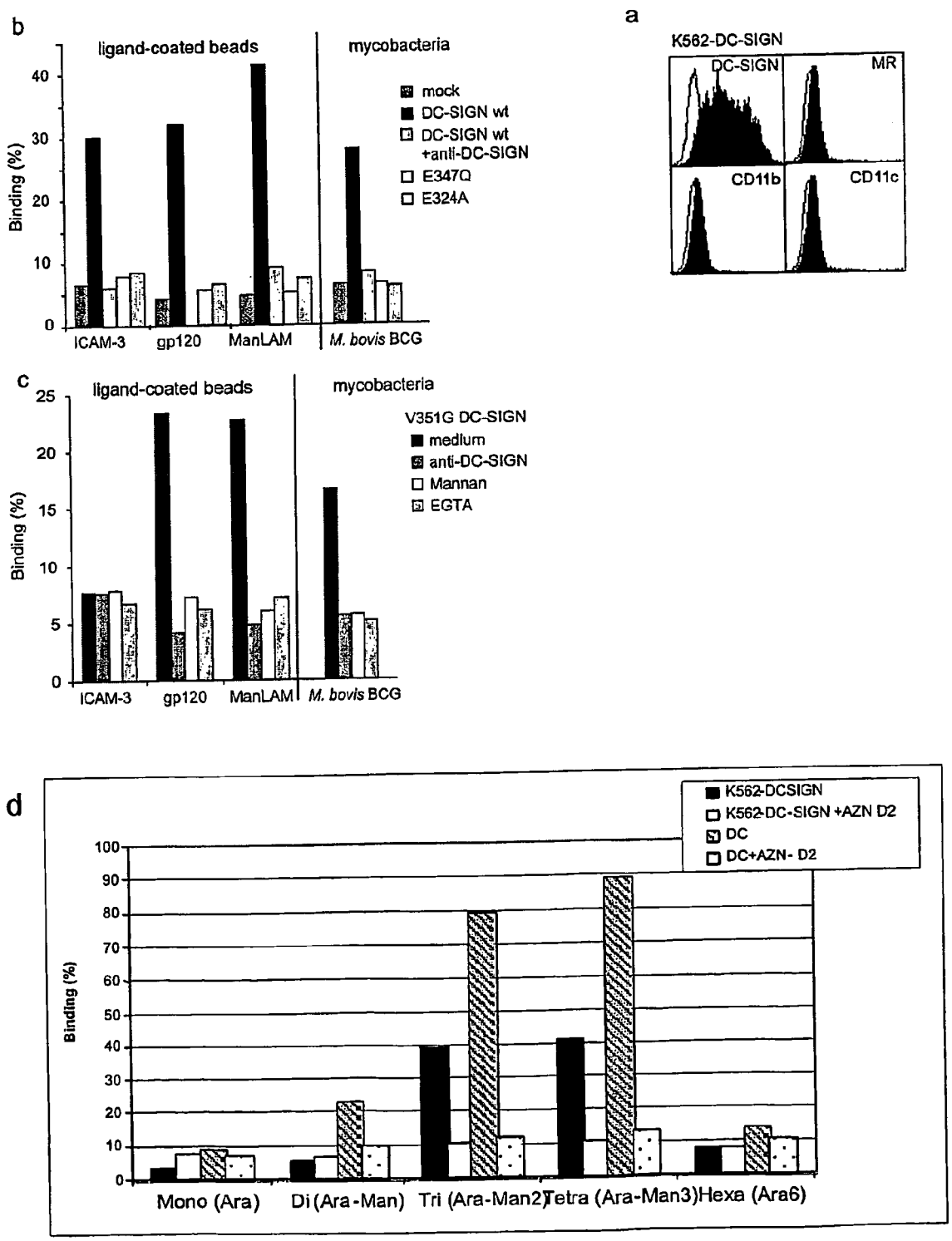
FIG. 7. Cellular DC-SIGN binds strongly to both viable mycobacteria and the mycobacterial component ManLAM through its primary binding site.
a) K562-DC-SIGN transfectants express high levels of DC-SIGN but lack expression of the other reported ManLAM receptors MR, CD11b and CD11c. Transfectants were generated as previously described?. Open histograms represent the isotype controls, and filled histograms indicate the specific antibody staining.
b) DC-SIGN, expressed by K562 transfectants, binds strongly to intact *M. bovis* BCG and the mycobacterial component ManLAM but not to AraLAM. The adhesion of cells to the LAM glycans was determined using the fluorescent bead adhesion assay. Binding to viable mycobacteria was determined by measuring the binding of K562 transfectants to FITC-conjugated mycobacteria (MOI 20) using flow cytometry. Specificity was determined by measuring binding in the presence of blocking antibodies against DC-SIGN. Standard deviation for the fluorescent bead adhesion assay and the mycobacteria binding assay was <5% and <2%, respectively. One representative experiment out of three is shown.
c) The Val351 amino acid residue is not essential for the interaction of DC-SIGN with *M. bovis* BCG and ManLAM, similar to HIV-1 gp120, whereas it is essential for ICAM-3 binding. Binding to the V351G DC-SIGN mutant expressed by K562 cells was measured as described in FIG. 2. Specificity was determined by measuring binding in the presence of blocking antibodies against DC-SIGN, mannan or EGTA. Standard deviation<5% (fluorescent bead adhesion assay) and <2% (mycobacteria binding assay). One representative experiment out of three is shown.
d) Binding of DC-SIGN to differential components of ManLAM. Neoglycoproteins Ara-Man, Ara-Man2, Ara-Man3 or Ara6 were coated on fluorescent beads and added to DC-SIGN expressing cells. DC-SIGN preferably binds Man2 and Man3 as demonstrated with the strong binding that can be blocked by the addition of anti-DC-SIGN antibodies (AZN-D1).

We used K562 transfectants stably expressing DC-SIGN to investigate the binding of cell-surface-expressed DC-SIGN to both *M. bovis* BCG and the mycobacterial component ManLAM. These cells do not express the previously reported mycobacterial receptors Mannose Receptor (MR), CD11b and CD11c (FIG. 7a). K562 transfectants express high levels of DC-SIGN (FIG. 7a) and bind strongly to both *M. bovis* BCG and ManLAM, in contrast to mock transfected K562 cells (FIG. 7b). The interaction is blocked by DC-SIGN-specific antibodies (FIG. 7b). The interaction of DC-SIGN with both *M. bovis* BCG and ManLAM is similar to that of the other DC-SIGN ligands ICAM-3 and HIV-1 (FIG. 7b). Thus, cellular DC-SIGN specifically binds to both *M. bovis* BCG and ManLAM, as was observed with recombinant DC-SIGN-Fc (FIG. 6c).

The C-type lectin domain of DC-SIGN contains two calcium ions, and the amino acid residues that are in close contact with $Ca^{2+}$ at site 2 ($Glu^{347}$, $Asn^{349}$, $Glu^{354}$ and $Asn^{365}$) form the core of the ligand binding site[23]. Changing in DC-SIGN either $Glu^{347}$ into Gln (E347Q), or $Asn^{349}$ and $Asn^{365}$ into Asp, resulted in complete loss of binding to whole mycobacteria and ManLAM (FIG. 7b and data not shown), similarly as was shown previously for both ICAM-3 and HIV-1 gp120 (FIG. 7b). The $Ca^{2+}$ at site 1, the so-called auxiliary site, coordinates the correct positioning of the primary binding site, and loss of this $Ca^{2+}$ by mutating $Asp^{320}$, $Glu^{324}$ (E324A), $Asn^{350}$ or $Asp^{355}$ into Ala residues resulted in complete loss of both *M. bovis* BCG and ManLAM binding (FIG. 7b and results not shown).

Recently, we demonstrated that the binding site of DC-SIGN for its cellular ligand ICAM-3 is distinct from that of HIV-1 gp120, since a specific mutation in DC-SIGN (V351G) abrogated ICAM-3, but not HIV-1 gp120 binding (FIG. 7c). Strikingly, the DC-SIGN V351G mutant also interacts with *M. bovis* BCG as well as ManLAM (FIG. 7c), demonstrating that both HIV-1 and mycobacteria bind similarly to DC-SIGN at a distinct site from the cellular ligand ICAM-3. The similar binding of both *M. bovis* BCG and ManLAM to DC-SIGN mutants further supports our findings that DC-SIGN specifically interacts with ManLAM on whole mycobacteria. Binding of fluorescent beads coated with distinct neoglycoproteins of ManLAM that consist of Arabinose, Arabinose-□1,5 mannose, Arabinose-□□1,5Man-□□1,2 Man, Ara-□□1,5Man-□□1,2Man-□□1,2Man or Ara6 demonstrate that DC-SIGN particularly recognizes in ManLam a di-mannose (Man □1,2 component) or mannosetriose (Man □1,2 component) (FIG. 7D).

Example 5

DC-SIGN is a Major Receptor for Mycobacteria on DC

Figure 8:
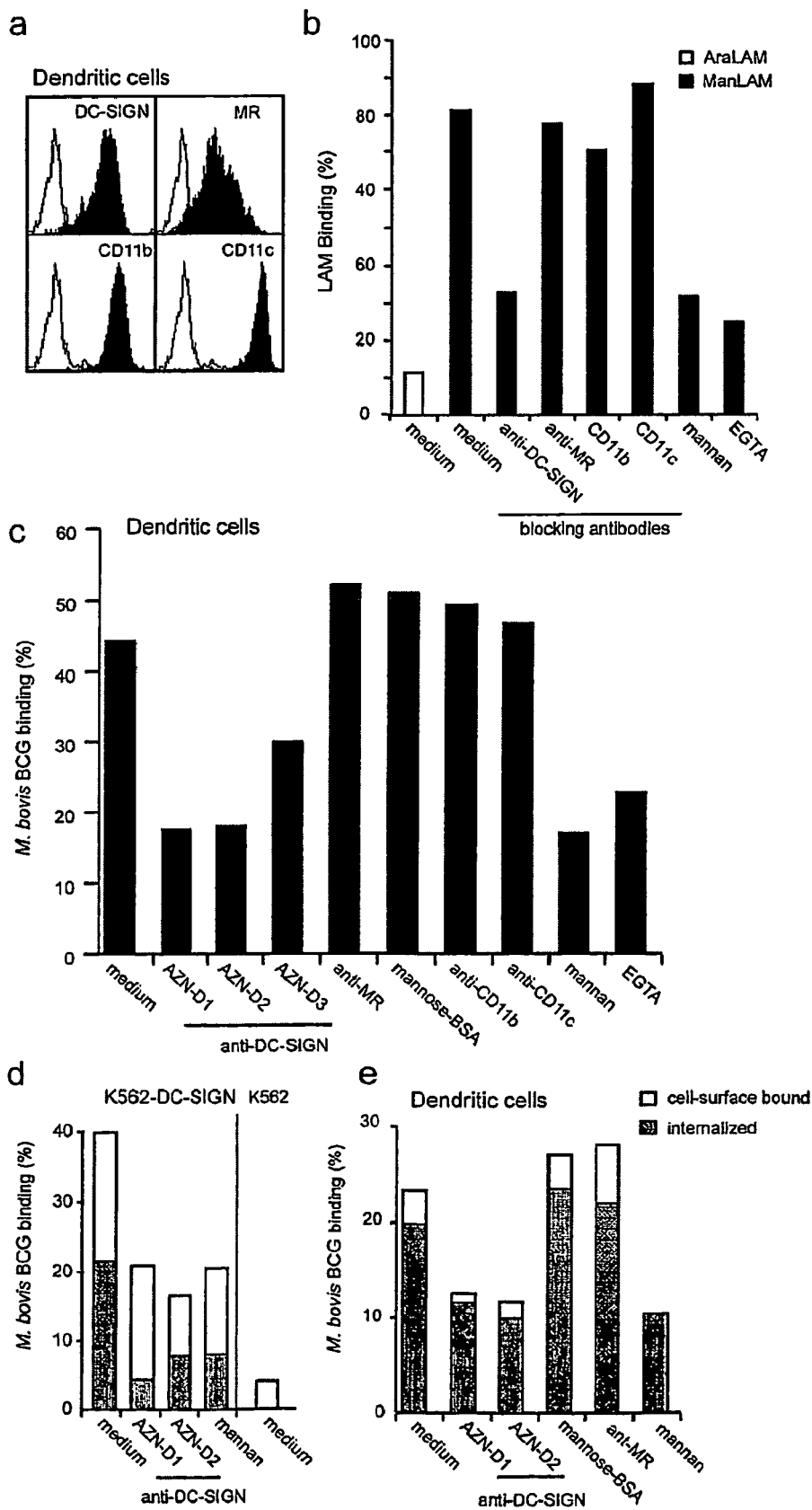
FIG. 8. DC-SIGN is an important receptor for both ManLAM and mycobacteria on DC.
a) Immature DC express high levels of DC-SIGN and the other reported LAM receptors MR, CD11b and CD11c.

Immature DC express, besides high levels of DC-SIGN, high levels of the receptors MR, CD11b and CD11c (FIG. 8a), which have previously been reported to mediate binding of mycobacteria by macrophages. We used blocking antibodies against these receptors to evaluate their contributions to ManLAM binding by DC. Immature DC bind strongly to ManLAM, but not to AraLAM, and the interaction was inhibited by the DC-SIGN-specific antibody, but strikingly not by any of the antibodies against MR, CD11b or CD11c (FIG. 8b). Both EGTA and the C-type lectin-specific inhibitor mannan block ManLAM binding by DC to a similar extent as the DC-SIGN-specific antibodies, demonstrating that DC-SIGN is the primary ManLAM-binding C-type lectin on immature DC that binds ManLAM (FIG. 8b).

The major contribution of DC-SIGN to the interaction of immature DC to ManLAM prompted us to investigate whether DC-SIGN could be important in the interaction of immature DC to whole mycobacteria. Immature DC strongly interacted with *M. bovis* BCG (FIG. 8c). Strikingly, DC-SIGN is a major receptor for *M. bovis* BCG, since the antibodies against DC-SIGN strongly inhibited the infection of immature DC with *M. bovis* BCG (FIG. 8c). Antibodies against MR, CD11b and CD11c did not inhibit the infection, whereas the C-type lectin inhibitor mannan blocked the infection to a similar level as the DC-SIGN antibodies (FIG. 8c). Moreover, the MR-ligand mannose-BSA did not inhibit the interaction of DC with *M. bovis* BCG (FIG. 8c) demonstrating that the C-type lectin domains of MR are not involved in *M. bovis* BCG infection of DC. Both the anti-MR antibody and mannose-BSA are inhibitors of MR-function since they block binding of another MR-ligand dextran to DC (results not shown). These results demonstrate that DC-SIGN is the primary C-type lectin on DC that functions as a receptor for *M. bovis* BCG. Other non-lectin receptors may participate in the interaction since the infection was not completely inhibited by antibodies against DC-SIGN (FIG. 8c).

Example 6

DC-SIGN Facilitates Capture and Internalization of M. bovis BCG by Immature DC through Binding of the Mycobacterial Cell-Wall Component ManLAM Next we investigated whether DC-SIGN mediates internalization of M. bovis BCG using trypan blue to quench surface FITC-conjugated mycobacteria. Mock transfected K562 cells did not phagocytose M. bovis BCG, whereas 50% of the K562 transfectant, expressing DC-SIGN, had internalized M. bovis BCG within 45 minutes (FIG. 8d). Both mannan and antibodies against DC-SIGN blocked the internalization of M. bovis BCG (FIG. 8d).

Immature DC are highly phagocytosing cells and indeed within 45 minutes more than 90% of the dendritic cells that bound M. bovis BCG, had internalized the mycobacteria (FIG. 8e). Similar as was observed for the binding of M. bovis BCG by DC (FIG. 8c), phagocytosis of M. bovis BCG is partly blocked by antibodies against DC-SIGN whereas both anti-MR antibodies and the MR-ligand mannose-BSA did not inhibit the observed phagocytosis (FIG. 8e). These results demonstrate that DC-SIGN facilitates capture and internalization of M. bovis BCG by immature DC through binding of the mycobacterial cell-wall component ManLAM.

Example 7

Mycobacteria and ManLAM are Internalized by DC-SIGN and Targeted to Lysosomes

Recently, we have demonstrated that DC-SIGN can function as an antigen receptor that internalizes antigens and targets them to lysosomal compartments for presentation on MHC Class II[10]. Therefore, the fate of the captured M. bovis BCG by immature DC was followed by immuno-fluorescence analyses. Immature DC were incubated with FITC-conjugated M. bovis BCG for 2 hours and both DC-SIGN and Lamp-1 were stained (FIG. 9a). The observed co-localization of DC-SIGN with FITC-conjugated M. bovis BCG further supports a role for DC-SIGN in the capture and internalization of mycobacteria (FIG. 9a). Phagocytosed mycobacteria are targeted to the lysosomes since the internalized FITC-conjugated mycobacteria co-localize with Lamp-1 staining (FIG. 9a). Similarly, ManLAM was also captured and internalized by DC-SIGN on immature DC since ManLAM staining co-localized with DC-SIGN (FIG. 9a) whereas AraLAM was not internalized by DC (results not shown). Internalized ManLAM co-localized with the lysosomal marker LAMP-1/CD107a in immature DC (FIG. 9a) indicating that internalized ManLAM is targeted to lysosomes. Thus, both whole mycobacteria and the cell-wall component ManLAM are similarly internalized by immature DC through DC-SIGN, supporting the results that DC-SIGN interacts with ManLAM on mycobacteria.

Recently, we demonstrated that binding of soluble ligands or antibodies to DC-SIGN triggers internalization of the DC-SIGN-ligand complex to the late endosomes/lysosomes, and results in down-regulation of DC-SIGN from the surface[10]. Therefore, we investigated whether DC-SIGN is internalized after ManLAM binding by measuring the cell-surface expression of DC-SIGN after ManLAM binding using a specific antibody against DC-SIGN. Indeed, binding of ManLAM, but not AraLAM, to DC-SIGN results in down-regulation of DC-SIGN (FIG. 9b), demonstrating that DC-SIGN on DC binds ManLAM and mediates the internalization of ManLAM to CD107a+ lysosomes. Moreover, other mycobacteria-receptors such as MR, CD11b and CD11c were not down-regulated (FIG. 9b). Thus, ManLAM binding to DC-SIGN triggers internalization of the DC-SIGN/ManLAM complex, and might enable antigen processing of ManLAM by DC.

Example 8

ManLAM Changes the Cytokine Production by DC through DC-SIGN

ManLAM is present not only a mycobacterial cell-wall component but is also secreted from phagosomes following macrophage ingestion of M. tuberculosis[31]. Potentially, mycobacteria within infected macrophages can influence bystander immune cells and modulate the immune response through secretion of ManLAM. The cytokine IL-10 is a potent immunosuppressive factor induced in macrophages by some intracellular bacteria to dampen down host immune responses and promote their survival[32]. We investigated the influence of ManLAM binding to DC-SIGN in IL-10 production by DC. ManLAM alone did not induce IL-10 production by immature DC (FIG. 10a). Strikingly, ManLAM, but not AraLAM, strongly induced IL-10 production by DC, when they received simultaneously an activation signal, such as LPS (FIG. 10a). This IL-10 induction was completely inhibited by DC-SIGN-specific antibodies to the level of LPS-activated DC alone (FIG. 10a). The findings that only ManLAM could induce IL-10 production, which could be blocked by DC-SIGN-specific antibodies indicates that the IL-10 induction is specific for the ManLAM(DC-SIGN interaction. Antibodies against DC-SIGN alone did not induce IL-10 production by LPS-activated DC (FIG. 10a), demonstrating that ligation of DC-SIGN alone is not sufficient for IL-10 induction. Thus, the binding of ManLAM to DC-SIGN triggers intracellular signals that induce IL-10 production by DC, indicating that mycobacteria target DC-SIGN to suppress the immune response and promote their survival in the host. Both immature and LPS-activated DC, alone or in combination with ManLAM, produced very low amounts of IL-12p70 (<5 pg/ml). Infection of immature DC with M. bovis BCG induced a strong production of IL-10 that was not inhibited by antibodies against DC-SIGN (FIG. 10b). No differences were observed in the presence of ManLAM (FIG. 10b). These results suggest that mycobacteria induce IL-10 production by direct infection as well as by secreting ManLAM.

Example 9

ManLAM Inhibits TLR4-Mediated DC Activation Through DC-SIGN

Immature DC are highly efficient in antigen capture and processing, whereas mature DC are specialized in the naive T cell activation necessary for cellular immune responses. Immature DC mature in response to specific 'danger' signals such as bacterial components (LPS) or inflammatory cytokines (TNFa, PGE2). We investigated the effect of ManLAM on the maturation of DC. Neither ManLAM nor AraLAM induced DC maturation, since both ManLAM and AraLAM, in contrast to LPS that triggers TLR4, did not up-regulate expression of the activation markers CD80, CD83, CD86 or HLA-DR (FIG. 11a).

Acute mycobacterial infections represent sites of inflammation that attract and induce DC maturation through the presence of maturation components. Therefore, we investigated the effect of ManLAM and AraLAM in combination with the stimulatory bacterial LPS. Toll-like receptor-4 (TLR4) interaction with LPS generates intracellular signaling, most notably via the transcription factor NFkB, that results in DC activation/maturation. Indeed, DC efficiently mature in the presence of LPS alone (FIG. 11b). Strikingly, this LPS-induced activation is inhibited in the presence of ManLAM, since the expression levels of the activation markers CD80, OD83 and CD86 were considerably lower than those of LPS-activated DC (FIG. 11b). The observed inhibition of DC activation/maturation is specific for ManLAM, since AraLAM did not inhibit DC activation (FIG. 11b). This is further supported by the ability of antibodies against DC-SIGN, that inhibit ManLAM binding, to completely restore LPS-induced maturation in the presence of ManLAM (FIG. 11b). These results indicate that ManLAM binding to DC-SIGN generates intracellular signals that interfere with the TLR4-mediated activation of DC. Moreover, this process is specific for the ManLAM-DC-SIGN interaction and DC-SIGN ligation alone is not sufficient since antibodies against DC-SIGN did not block LPS-induced DC activation/maturation (FIG. 11b).

Example 10

M. bovis BCG-Induced DC Maturation is Inhibited by ManLAM

Both M. tuberculosis and M. bovis BCG are able to induce DC maturation through their cell-wall components via TLR2- and TLR4-mediated signaling[33-36]. Indeed, M. bovis BCG infection of immature DC results in DC maturation, as demonstrated by the increased expression of MHC class II and the co-stimulatory molecules CD80, CD83 and CD86 after M. bovis BCG infection (FIG. 12a). Next, we investigated whether ManLAM binding to DC-SIGN prevented M. bovis BCG-induced DC maturation, since immature DC attracted to sites of mycobacterial infection will encounter both secreted ManLAM and intact mycobacteria. Strikingly, the M. bovis BCG-induced DC maturation is inhibited strongly by Man (FIG. 12b). The expression of MHC class II, CD80, CD83 and CD86 on M. bovis BCG-infected DC in the presence of ManLAM was considerably lower than on M. bovis BCG-infected DC (FIG. 12b). Moreover, the maturation was mostly restored when DC were pre-incubated with the blocking DC-SIGN-specific antibody (FIG. 12b), demonstrating that the ManLAM interaction with DC-SIGN prevents DC maturation by M. bovis BCG. Moreover, AraLAM did not block the DC maturation by M. bovis BCG (FIG. 11c), since the co-stimulatory molecules, CD80, CD83 and CD86, are expressed at similar levels on both infected DC and AraLAM-treated infected DC. This indicates that the DC-SIGN-ManLAM interaction blocks the maturation of DC induced by LPS as well as M. bovis BCG.

Example 11

S. mansoni Soluble Egg Antigens (SEA) Bind to Human Immature Dendritic Cells (DC) Through Interaction with DC-SIGN Because DC are central in directing Th1-Th2 responses, we searched for a cell-surface receptor expressed on DC that interacts with S. mansoni SEA. To detect binding of SEA to human immature DC, a fluorescent bead adhesion assay was developed. Fluorescent beads were pre-coated with monoclonal antibodies (MAbs) to SEA glycan antigens and then used to capture SEA. The conjugated beads were allowed to interact with DC. SEA is a mixture of glycoproteins, containing many immunogenic glycan antigens (3, 36). Major glycan antigens present in SEA, and the recognition of these antigens by anti-glycan MAbs, are depicted in FIG. 13. To capture SEA on the fluorescent beads, we used MAbs against GalNAcβ1,4GlcNAc (LDN) and GalNAcβ1,4(Fuc□1,2Fuc□1,3)GlcNAc (LDN-DF) (FIG. 13), both epitopes that occur on many glycoconjugates within SEA and which are absent on DC. Strong binding of SEA to DC was observed with SEA coated fluorescent beads that were coupled via anti-LDN MAb as well as via anti-LDN-DF MAb (FIG. 14b). Binding of SEA to DC was comparable in strength to the binding of HIV-1 gp120 to DC. Because the C-type lectins DC-SIGN and the MR, that are expressed by immature DC (FIG. 14a), are potential receptors for the recognition of glycan antigens, we investigated whether antibodies directed against the C-type lectin CRD of these molecules, or mannan hapten could inhibit binding of SEA to the DC. The binding of SEA to DC was strongly blocked both by the anti-DC-SIGN MAb AZN-D1, that binds to the CRD of DC-SIGN and by mannan, but not by the anti-MR MAb clone 19 (FIG. 14b). These data indicate that DC-SIGN is not only a pathogen receptor on DC for HIV-1, but also for Schistosome SEA.

Example 12

A Sub-Fraction of SEA Contains High Affinity Ligands for DC-SIGN

To further analyze the binding properties of DC-SIGN to S. mansoni SEA, we investigated binding of soluble chimeric DC-SIGN-Fc to SEA. In an ELISA based assay DC-SIGN-Fc showed efficient binding to wells coated with SEA (FIG. 15a). Binding of DC-SIGN-Fc to SEA is mediated by the CRD of DC-SIGN, since the interaction was completely inhibited by the anti-DC-SIGN antibody AZN-D1, or EGTA that removes $Ca^{2+}$ ions that are essential for carbohydrate binding. Binding of DC-SIGN-Fc to SEA is likely to be high affinity, since binding was observed at very low coating concentrations of SEA (FIG. 16). Because SEA contains many different glycoproteins, we investigated whether a subset of glycoproteins within SEA interact with DC-SIGN. SEA glycoproteins were separated by SDS-PAGE and analyzed by Western blotting with DC-SIGN-Fc and anti-glycan antibodies reactive with $Le^x$ and LDN-DF, respectively. Among the proteins present in SEA a major protein of approximately 70-80 kD, and two minor high-molecular proteins showed interaction with soluble DC-SIGN-Fc (FIG. 17). Remarkably, some glycoproteins of similar apparent molecular weight as those reacting with DC-SIGN-Fc bound to MAbs specific for $Le^x$ and LDN-DF glycans.

Example 13

DC-SIGN Binds to α3-Fucosylated Glycans

Many glycoproteins of SEA are heavily fucosylated (3, 36). Because it has been reported that DC-SIGN may exhibit binding to both mannose and fucose, and Western blotting of SEA suggested that $Le^x$ and/or LDN-DF glycans are present on SEA proteins with similar apparent MW as the SEA proteins binding to DC-SIGN, we explored whether defucosylation of SEA affects its recognition by DC-SIGN-Fc. Treatment of SEA with the Xanthomonas □1,3/1,4fucosidase resulted in 50% decreased reactivity of anti-$Le^x$ MAb to SEA, whereas no loss in reactivity was observed, as expected, with anti-LDN-DF Mab. The LDN-DF epitope contains terminal α2-linked fucose. The results thus indicate that the that the glycosidase treatment specifically removed part of the α3-fucose moieties present on SEA. The loss in α3/-fucose residues in SEA upon treatment with the Xanthomonas α1,3/α1,4-fucosidase also resulted in a 25% loss of binding of DC-SIGN-Fc (results not shown). These data suggest that α1,3/α1,4-linked fucose residues may be important for binding of soluble DC-SIGN-FC to SEA.

Next we investigated whether one or more of the fucosylated SEA antigens $Le^x$, LDNF or LDN-DF (see FIG. 13) may function as ligand(s) for DC-SIGN on SEA. We analyzed the potential of DC-SIGN-Fe to bind to neoglycoproteins containing these glycan antigens in ELISA. The results show that DC-SIGN-FC strongly interacts with the neoglycoprotein HSA-$Le^x$ and to a lesser extent with BSA-LDNF, which both carry a terminal α3-fucose. By contrast, DC-SIGN-FC does not bind BSA-LDN-DF in which the α3-fucose is capped with an α2-fucose (FIG. 18). The binding is fucose-dependent, since no binding was observed to neoglycoproteins carrying Galβ1,4GlcNAc (LN) or GalNAcβ1,4GlcNAc (LDN). The binding to $Le^x$ and LDNF by DC-SIGN is mediated through its CRD, since binding was inhibited by anti-DC-SIGN and EDTA. In conclusion, these results indicate that DC-SIGN strongly recognizes the α3-fucosylated trisaccharide $Le^x$ and most likely interacts with α3-fucosylated glycans on SEA such as $Le^x$ and/or LDNF.

Example 14

The Amino Acid Residue $Val^{351}$ within DC-SIGN is Crucial for Binding of DC-SIGN to Both SEA and $Le^x$ The C-type lectin domain of DC-SIGN binds two $Ca^{2+}$ ions and those amino acid residues in close contact with $Ca^{2+}$ at site 2 ($Glu^{347}$, $Asn^{349}$, $Glu^{354}$ and $Asn^{865}$) or with $Ca^{2+}$ at site 1 ($Asp^{320}$, $Glu^{324}$, $Asn^{350}$ and Asp355) are essential for ligand binding[37]. Because the results above indicated that the α3-fucosylated trisaccharide $Le^x$ on SEA may function as a ligand for DC-SIGN, we investigated the binding properties of these antigens to K562 cell transfectants expressing mutated forms of DC-SIGN. Mutation of either $E^{324}$ to Ala, or $E^{347}$ to Gln in DC-SIGN (FIG. 19a) resulted in complete loss of interaction with both SEA and $Le^x$, indicating that binding to these antigens is mediated through the primary ligand-binding site and is $Ca^{2+}$ dependent (FIG. 19b). This is similar to results reported for binding of DC-SIGN to HIV-1 gp120[37].

It has recently been demonstrated that a specific mutation in the CRD of DC-SIGN ($V^{351}G$) allows binding of HIV-1 gp120, but abrogates binding to ICAM-3, a T-cell ligand that has been shown previously to interact with DC-SIGN. Our results indicate that the DC-SIGN $V^{351}G$ mutant does not bind to either SEA or $Le^x$, whereas binding to HIV-1 was still observed, indicating that $Val^{351}$ is essential for binding to both SEA and $Le^x$, but not to HIV-1 (FIG. 19b). To determine whether the SEA binding site overlaps with the ICAM-3 or HIV-1 binding sites on DC-SIGN, we explored whether SEA inhibits the interaction of DC-SIGN to ICAM-3 and HIV-1 gp120 in a DC-binding assay. The results demonstrate that SEA can inhibit the interaction between DC and ICAM-3 as effectively as the anti-DC-SIGN MAb, whereas binding of DC-SIGN to HIVgp120 was only partially inhibited by SEA (FIG. 19c). These results demonstrate that the SEA binding site on DC-SIGN may resemble the ICAM-3 binding site and may partly overlap the binding site for HIV-1 gp120.

Example 15

L-SIGN Does Not Interact with DC-SIGN Binding SEA or Lewis X

L-SIGN, an adhesion receptor that resembles DC-SIGN by recognizing ICAM-2, ICAM-3 and HIV-gp120, contains a CRD that is nearly identical to that of DC-SIGN[38], and both receptors recognize high-mannose-type N-glycans. Our results above demonstrated a novel binding activity of DC-SIGN to fucosylated glycans and showed that $Val^{351}$ in DC-SIGN is essential for this binding activity. At the corresponding position in the CRD of L-SIGN a Ser is present instead of Val (FIG. 19a), raising the question whether L-SIGN can recognize SEA and $Le^x$. Binding of L-SIGN to these antigens was investigated by an adhesion assay where fluorescent beads containing SEA and Lex-PAA, respectively, were incubated with transfected K562 cells expressing recombinant DC-SIGN and L-SIGN (FIG. 19e). K562 cells expressing L-SIGN (K-L-SIGN) did not interact with SEA nor with $Le^x$-PAA, but showed interaction with HIV-1 gp120. K562 cells expressing DC-SIGN (K-DC-SIGN) bound to SEA and $Le^x$, as expected (FIG. 19b). These data show that the two highly related receptors DC-SIGN and L-SIGN have distinct carbohydrate binding specificity and pathogen-recognition features.

Example 16

Figure 20A:
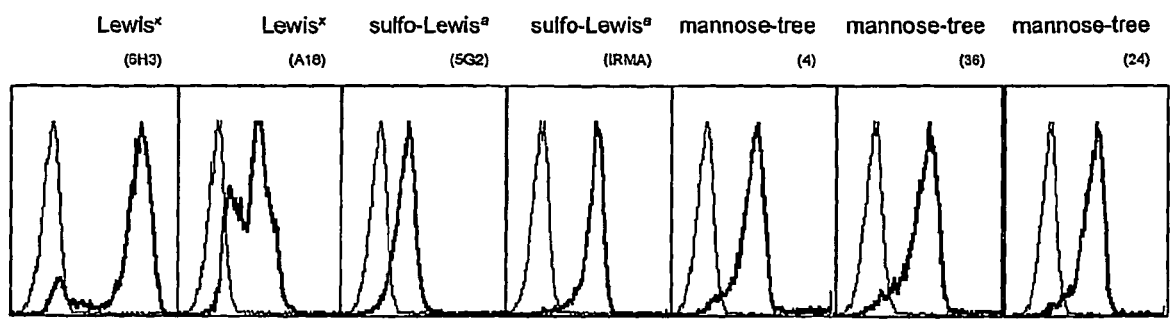
Figure 20B:
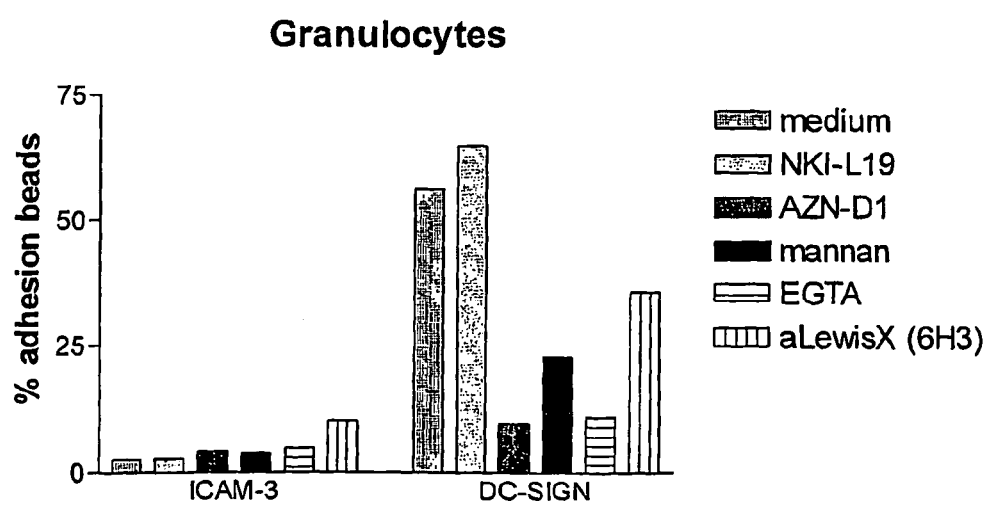

Novel Carbohydrate Specificity Predicts and Confirms Novel Cellular Counter-Structures for DC-SIGN; DC-SIGN Recognizes $Le^x$ Carbohydrates on CD66a Present on Granulocytes to Mediate DC-Granulocyte Interactions DC-SIGN is known to interact with ICAM-2 and ICAM-3, however the glycan ligands on these molecules have not yet been identified. The blood group antigen $Le^x$ (CD15) is expressed by gastric mucosal epithelial cells, and by polymorphonuclear leukocytes (granulocytes) (FIG. 20a); indeed DC-SIGN-Fc-coated beads bind strongly to granulocytes (FIG. 20b). Moreover, DC-SIGN-Fc also binds strongly to granulocytes (FIG. 21). The binding is specific for DC-SIGN since it can be inhibited by anti-DC-SIGN antibodies, mannan and depletion of calcium by EGTA but also by an anti-$Le^x$ antibody indicating that the cellular interaction is $Le^x$ dependent (FIGS. 20 and 21). Moreover, an antibody against $Le^x$ specifically reduces the observed adhesion of DC-SIGN to CD66a, CD66e and CD11b demonstrating that $Le^x$ carbohydrates indeed participate in the interaction (FIGS. 20, 54, 59D). Other glycan structures such as $Le^y$ and $Le^b$ can also be involved since the observed block is not complete. This demonstrates that granulocytes express a cell-surface glycoprotein that expresses a glycan structure that is recognized by DC-SIGN.

Moreover, we predict that based on the carbohydrate recognition pattern of DC-SIGN (FIG. 1), DC-SIGN may also mediate binding of DC to tumor cells, since $Le^y$ expression is increased on many carcinomas including ovary, pancreas, prostate, breast, colon and non-small cell lung cancers[24], while sulfo-$Le^a$ is present on certain tumors that express mucins. Thus, these results indicate that recognition of distinct carbohydrate structures by DC-SIGN may allow DC mediated cell adhesion to T cells, endothelial cells, PMNs as well as to tumor cells.

Immuno-precipitation studies revealed that DC-SIGN-Fc does not bind the cellular DC-SIGN counter-structures ICAM-2 or ICAM-3 from granulocytes but binds to a novel glycoprotein with a weight of 66 kD protein that is only present on granulocytes (FIG. 22a). The fact that DC-SIGN binds $Le^x$ carbohydrates and the fact that granulocytes express high levels of CD66a, a $Le^x$ bearing cell-surface receptor with a molecular weight of 66 kD (FIGS. 22b and c), prompted us to examine binding of CD66a-Fc binding to DC-SIGN expressing transfectants and immature DC that express DC-SIGN. Strong binding of CD66a to DC-SIGN expressed by both DC and DC-SIGN transfectants was observed (FIG. 23c), similar as was observed for ICAM-3 binding (FIG. 23b). Un-coated beads did not interact with these cells (FIG. 23a). The interaction of CD66a with DC-SIGN seemed stronger than the previously described ICAM-3-DC-SIGN interaction. These data indicate that CD66a is a novel cellular counter-structure of DC-SIGN and may play an important role in mediating DC-granulocyte cellular interactions that play a role in innate immune responses.

Example 17

DC-SIGN Binds Strongly to a Subset of Cells in Peripheral Blood

To determine whether DC-SIGN preferentially interacts with naive T cells expressing high levels of ICAM-3, as was previously postulated, we started to investigate DC-SIGN binding to total PBL population of cells. Strikingly, DC-SIGN-Fc interacted with a CD3⁻ cell population that were CD56⁺ and belonged to NK cell subset (FIG. 24). Moreover, the interaction was concentration dependent (FIG. 25) and could be blocked with antibodies against DC-SIGN (FIGS. 24 and 25). The CD56⁺ NK cells in blood can be divided into two cell populations: $CD56^{dim}CD16^+$ and $CD56^{high}CD16^-$ NK cells (FIG. 26). DC-SIGN-Fc specifically bound to the $CD56^{dim}CD16^+$ NK population and the interaction could be inhibited by anti-DC-SIGN antibodies (FIG. 26). ICAM-1-Fc did not interact with the $CD56^{dim}CD16^+$ NK population, demonstrating that the interaction of DC-SIGN-Fc is specific and not mediated by the Fc tag. Both NK cell populations were able to specifically interact with ICAM-1-Fc after activation of their β2 integrin LFA-1 (FIG. 26). Thus, these results indicate that DC interact with the $CD56^{dim}CD16^+$ NK cells through DC-SIGN. Strikingly, both NK populations have similar levels of ICAM-2 and ICAM-3, indicating that DC-SIGN may bind another novel ligands on the $CD56^{dim}CD16^+$ NK population. Indeed, immuno-precipitation reveals that DC-SIGN-Fc binds, besides ICAM-2, also a molecule with molecular weight of 166 kDa (FIG. 27). This ligand could be CD166 or CD16, which is heavily glycosylated and only expressed on NK cells.

Example 18

DC-SIGN Mediates DC-NK Cell Interaction and is Involved in the Lysis of Immature DC by NK Cells To investigate whether the interaction of DC-SIGN with NK cells is relevant in NK mediated immune response we invested both the lysis of DC by NK cells and the maturation of DC by NK cells; two processes that have been recently identified to play an important role in innate immunity.

DC-SIGN did not inhibit DC maturation by NK cells (FIG. 28) but was strongly involved in the NK-mediated immature DC lysis (FIG. 29), since antibodies against DC-SIGN inhibited the NK-mediated lysis of DC. These data indicate that DC-SIGN regulates the interaction of immature DC with NK cell by binding a 166 kDa protein on $CD56^{dim}CD16^+$ NK cells. This DC-SIGN-NK cell interaction also strongly enhances NK-mediated lysis of cell-lines transfected with DC-SIGN (FIG. 30), whereas antibodies against DC-SIGN inhibit the lysis. These results indicate that DC-SIGN may be important in the interaction of DC with NK cells and that inhibition of this interaction prevents NK-mediated lysis.

Example 19

DC-SIGN Interacts with Herpes Simplex Virus Type 1 and 2

Previous results demonstrated that DC-SIGN specifically interacts with HIV-1[39] and recently it was published that DC-SIGN binds to Ebola virus[40]. Therefore, we investigated whether DC-SIGN and its homologue L-SIGN can interact with other viruses, that contain glycosylated envelope proteins. Strikingly, DC-SIGN-Fc binds strongly to Herpes simplex virus (HSV)-1 and -2, and this interaction is specifically inhibited by antibodies against DC-SIGN (FIG. 31). Further analysis demonstrates that DC-SIGN interact with the HSV glycoprotein gB (FIG. 32) since DC-SIGN expressed by DC and transfectants binds strongly to gB-coated beads. This interaction is blocked with anti-DC-SIGN antibodies (FIG. 32). DC-SIGN is specifically expressed by DC and L-SIGN is expressed by Liver sinusoidal endothelial cells (LSEC) and some macrophage populations. These data indicate that both DC-SIGN and L-SIGN could be involved in the interaction of HSV with DC and LSEC, respectively. Indeed, DC strongly bind to HSV-1 gB and the interactions are mediated by DC-SIGN, since antibodies against DC-SIGN block this interaction (FIG. 32). Thus, the interaction of DC with HSV is mediated by DC-SIGN and this C-type lectin could be important in the infection of DC by these viruses. Moreover, these data could suggest that these viruses target DC-SIGN on DC not only to infect these DC but also to evade the immune response by modulating DC function as we demonstrated for mycobacteria and HIV-1.

Example 20

Materials and methods particular to this example and relevant for the experiments described in FIGS. 33 to 66.
Bacterial Strains.
H. pylori clinical isolates of different geographic origins (The Netherlands, Canada, Poland, Italy, and the People's Republic of China) have been described before[5], as well as H. pylori strain NCTC 11637 and phase variants 1c, K4.1, K5.1, 3a, and 1b[9]. H. pylori strain 4187E and generation of futA (gene HP0379) and futB (gene HP0651) knockout mutants have been described[10]. Clinical isolate H. pylori J223 was a obtained from Dr. H. P. Wirth[6]. $Le^{x/y}$ positive and negative variants of J223 were isolated as previously described[9]. Briefly, bacteria from the biopsy were inoculated on Dent plates (Columbia agar, 5% horse blood+Dent supplement), followed by one single passage in fluid phase (Brucella broth+3% fetal calf serum) and distribution over solid media, after which detection of LPS phase variants took place by colony blotting[9]. Genotyping by Amplified Fragment Length Polymorphism (AFLP) analysis was performed as described in reference[39] with the following modifications: In a final volume of 20 mL, 20 ng of purified chromosomal DNA was digested with 1 U of EcoRI (Pharmacia, Uppsala, Sweden) and 1 U of MseI (New England Biolabs, Beverly, Mass.). The final volume then was increased to 30 mL by addition of 50 pmol each of the EcoRI adaptor and MseI adaptor, 1.2 U of T4 DNA ligase (Pharmacia), 1 mM ATP, and ligase buffer.

The adaptors were allowed to ligate to the restriction fragments for 16 h at 167° C, after which the sample was diluted with distilled water in a final volume of 500 mL. Texas Red fluorescent-labeled EcoO primer (50-AGACTGCGTAC-CAATTC-30 (SEQ ID NO: 1) Isogen Bioscience, Maarssen, The Netherlands); and unlabeled MseO primer (50-GAC-GATGAGTCCTGAG-30) (SEQ ID NO: 2) were used for DNA amplification in a GeneAmp PCR system 9700 thermal cycler (Perkin-Elmer) with 35 cycles: denaturation (30 s at 94° C.), annealing (30 s at 65-56° C.), and DNA molecule extension (60 s at 72° C.). In the first 12 cycles, the annealing temperature was lowered 0.7° C. per cycle. After completion of the cycle program, each sample was analyzed according to the manufacturer's instructions in a Vistra 725 automated DNA sequencer (Amersham Life Sciences). Fluorescent AFLP images were stored as TIFF files with the Vistra 2 TIFF software (Amersham).

Monoclonal Antibodies and Glycoconjugates.

*H. pylori* strains and phase variants were serotyped as previously described[5] with the following monoclonal antibodies (mAbs): Hp151, specific for Le$^y$, 6H3, specific for monomeric Le$^x$ and 4D2, specific for H type 1 (all three a kind gift from R. Negrini, General Hospital, Brescia, Italy). MAb 54.1F6A, specific for polymeric Lewis x (a kind gift from G. van Dam, Leiden, The Netherlands), NAM61-1A2, specific for i antigen (a kind gift from D. Blanchard, Regional Blood Transfusion Service, Nantes, France)[10]. MAbs AZN-D1 and AZN-D2[21] were used to block DC-SIGN and MAb Clone 17 (a kind gift from S. Gordon, University of Oxford, UK) was used to block the mannose receptor.

Synthetic glycoconjugates (Syntesome, Munich, Germany) comprised mono- and oligosaccharides that were multivalently linked to a polyacrylamide carrier. Ceramide-linked dimeric-, trimeric and tetrameric Le$^x$ antigens were a kind gift from R. R. Schmidt, University of Konstanz, Germany, and were synthesized as described[40].

Cells

Immature DC were generated by culturing monocytes in RPMI-1640/10% FCS in the presence of IL-4 (500 U/ml, Schering-Plough, Kenilworth, N.J.) and GM-CSF (800 U/ml, Schering-Plough) for 5-8 days[41]. K-562 cells, K-562-DC-SIGN cells and RAW 264.7 macrophages were cultured as described[41].

Bacterial Binding

*H. pylori* cells were labeled with FITC. Cells (50,000) in TSM with 0.5% BSA were preincubated with 20 ug/ml mAb, 200 ug/ml mannan or 10 mM EDTA for 10 min at RT. FITC-labeled bacteria (10 bacteria/cell) were added and incubated for 45 min at 37° C. Samples were analyzed by flow cytometry.

Soluble DC-SIGN-Fc Adhesion Assay.

The soluble DC-SIGN adhesion assay was performed by ELISA[42]. Antigens (either 3.75×10$^6$ bacterial cells/well or 5 μg/ml, in case of LPS or glycoconjugates) were coated in ELISA plates and soluble DC-SIGN-Fc (1 □g/ml in TSM) binding was determined by an anti-humanIg-Fc ELISA. When indicated, DC-SIGN-Fc was preincubated with 20 ug/ml mAb, 200 ug/ml mannan or 5 mM EDTA for 10 min at room temperature.

Immunohistochemistry

After informed consent by the patients, 2 antral biopsies were collected during gastroscopy. Tissue cryosections were fixed in acetone and incubated with AZN-D1 followed by anti-mouse-HRP. Staining was performed with the ABC-AP Vectastain kit and AEC (Vector Laboratories, Burlingame, Calif.) and sections were counterstained with heamatoxilin. In parallel, the other biopsy was analyzed for *H. pylori* infection by incubation in urease-medium for 12 hrs. No differences in morphology and staining were observed between non infected and infected individuals.

DC Activation and Th1/Th2 Differentiation

To analyze maturation, DC (180,000 cells) were incubated with *H. pylori* for 1 hr at multiplicity of infection (M.O.I) of 1, 5, 10, 20, washed and cultured for 20 hrs. Cells were analyzed for maturation markers (CD80, CD86, CD83, HLA-DR) by flowcytometry and supernatant was collected for cytokine ELISA[22]. For T cell differentiation, DCs were cocultured with *H. pylori* (M.O.I of 10) for 2 days, washed and incubated with CD45RA+, CD4+T cells (5,000 T cells/20,000 DCs). In parallel, DCs were analyzed for maturation markers, described above, and cytokine production after stimulation with J558 transfected with CD40L kind gift from P. Lane, University of Birmingham, UK) in the presence or absence of IFN-□ (1000 U/ml).

Quiescent T cells were restimulated with PMA (10 ng/ml, Sigma-Aldrich, St. Louis, Mo.) and ionomycin (1 μg/ml, Sigma-Aldrich) for 6 hr, the last 5 hrs in the presence of brefeldin A (10 μg/ml, Sigma-Aldrich). Single-cell production of IL-4 and IFN-γ was determined by intracellular flow-cytometry[43].

Results

DC-SIGN has been demonstrated to have a carbohydrate specificity for mannose-containing carbohydrates, Lewis antigens and GlcNAc-containing structures (FIGS. 33, 34, 63-66). We have demonstrated that the carbohydrate specificity of L-SIGN is different since it does not recognize Lewis antigen carbohydrate structures whereas it does recognize high mannose structures (FIGS. 33 and 34). The murine homologue mSIGNR1 recognizes similar to DC-SIGN high mannose and Lewis antigens, but has also specificity for sialylated Lewis antigens ill contrast to DC-SIGN and L-SIGN (FIGS. 33 and 34).

DC-SIGN is a C-type lectin in particular highly expressed on Dendritic cells. Its function is to recognize antigen and process and present this very efficiently into MHC class I and II molecules.

It has long been thought that DC-SIGN is a pathogen recognition receptor that recognizes pathogens to activate the immune system, but as it seems now, the long list of pathogens that target DC-SIGN all persist and escape immunity by different mechanisms. We have now four examples of pathogens that target DC-SIGN to survive in the host.

1. HIV-1 and HCV target DC-SIGN to 'hide' within DC and escape the intracellular routing to the lysosomal compartment.
2. Secretion of ManLam by mycobacteria targets DC-SIGN to induce downmodulation of TLR induced DC maturation, and induction of IL-10.
3. the human gastric pathogen *Helicobacter pylori* persists: Lipopolysaccharide phase variants modulate the Th1/Th2 balance through interaction with the dendritic cell lectin DC-SIGN.
4. *Lactobacillus* target DC-SIGN on DC and induce regulatory T cells, inhibition of recognition of *Lactobacillus* by DC-SIGN reduces the regulatory state of T cells. It is therefore supposed that DC-SIGN is a receptor that 'normally' recognize self-antigen to tolerize (Annual Review Immunology, 2004). We here demonstrate that targeting of DC-SIGN by lactobacilli can indeed induce regulatory T cells. Furthermore it seems that DC-SIGN can also recognize the tumor antigen CEA (CD66e) in particular Lewis X and Y. These tumor antigens may be secreted and suppress DC activation in a similar way as ManLam of mycobacteria tuberculosis.

The interaction of DC with granulocytes is elucidated by the fact that DC-SIGN recognizes CD66a and CD11b on granulocytes. In particular Lewis X antigen on these molecules is recognized. In that way DC-SIGN functions as a cell adhesion receptor that mediates cellular interactions of granulocytes with DC. This cellular adhesive function between granulocytes and dendritic cells has never been reported but it is likely that the granulocyte DC interaction is essential to form a bridge between the innate immune response and the adaptive immune response in such a way that the granulocyte passes the infectious agents to the DC mounting an adequate immune response. In particular the granulocyte activates and matures the DC, inducing upregulation of cytokines and costimulatory molecules which is necessary for DC migration and initiation of the adaptive immune response. The interaction of DC with granulocytes is also seen in vivo in the situation of Crohns disease. A new pathogen that interacts with DC-SIGN on DC is *Neisseria Meningitidis*. Strain variants demonstrate that in particular one strain mutant IgtB interacts which contains endstending GlcNAc residue. Other experiments (FIG. 66) demonstrate the DC-SIGN also recognizes GlcNac.

References

1. Bancherau, J., F. Briere, C. Caux, J. Davoust, S. Lebecque, Y. J. Liu, B. Pulendran, and K. Palucka. 2000. Immunobiology of dendritic cells. Annu Rev Immunol 18:767-811.
2. Banchereau, J. and R. M. Steinman. 1998. Dendritic cells and the control of immunity. Nature 392:245-52.
3. Lanzavecchia, A. and F. Sallusto. 2001. Regulation of T cell immunity by dendritic cells. Cell 106:263-6.
4. Steinman, R. M. 1991. The dendritic cell system and its role in immunogenicity. Annu Rev Immunol 9:271-96.
5. Palucka, K. and J. Banchereau. 2002. How dendritic cells and microbes interact to elicit or subvert protective immune responses. Curr Opin Immunol 14:420-31.
6. Underhill, D. M. and A. Ozinsky. 2002. Toll-like receptors: key mediators of microbe detection. Curr Opin Immunol 14:103-10.
7. Thoma-Uszynski, S., S. Stenger, O. Takeuchi, M. T. Ochoa, M. Engele, P. A. Sieling, P. F. Barnes, M. Rollinghoff, P. L. Bolcskei, M. Wagner, S. Akira, M. V. Norgard, J. T. Belisle, P. J. Godowski, B. R. Bloom, and R. L. Modlin. 2001. Induction of direct antimicrobial activity through mammalian toll-like receptors. Science 291:1544-7.
8. Figdor, C. G., Y. van Kooyk, and G. J. Adema. 2002. C-type lectin receptors on dendritic cells and Langerhans cells. Nature Rev Immunol 2:77-84.
9. Mahnke, K., M. Guo, S. Lee, H. Sepulveda, S. L. Swain, M. Nussenzweig, and R. M. Steinman. 2000. The dendritic cell receptor for endocytosis, DEC-205, can recycle and enhance antigen presentation via major histocompatibility complex class II-positive lysosomal compartments. J Cell Biol 151:673-84.
10. Engering, A., T. B. Geijtenbeek, S. J. van Vliet, M. Wijers, E. van Liempt, N. Demaurex, A. Lanzavecehia, J. Fransen, C. G. Figdor, V. Piguet, and Y. van Kooyk. 2002. The dendritic cell-specific adhesion receptor DC-SIGN internalizes antigen for presentation to T cells. J Immunol 168: 2118-26.
11. Drickamer, K. 1999. C-type lectin-like domains. Curr Opin Struct Biol 9:585-90.
12. Geijtenbeek, T. B. H., D. S. Kwon, R. Torensma, S. J. van Vliet, G. C. F. van Duijnhoven, J. Middel, I. L. Cornelissen, H. S. Nottet, V. N. KewalRamani, D. R. Littman, C. G. Figdor, and Y. van Kooyk. 2000. DC-SIGN, a dendritic cell-specific HIV-1-binding protein that enhances transinfection of T cells. Cell 100:587-97.
13. Astarie-Dequeker, C., E. N. N'Diaye, V. Le Cabec, M. G. Rittig, J. Prandi, and I. Maridonneau-Parini. 1999. The mannose receptor mediates uptake of pathogenic and non-pathogenic mycobacteria and bypasses bactericidal responses in human macrophages. Infect Immun 67:469-77.
14. Geijtenbeek, T. B. H., R. Torensma, S. J. van Vliet, G. C. F. van Duijnhoven, G. J. Adema, Y. van Kooyk, and C. G. Figdor. 2000. Identification of DC-SIGN, a novel dendritic cell-specific ICAM-3 receptor that supports primary immune responses. Cell 100:575-85.
15. Geijtenbeek, T. B. H., Krooshoop, D. J. E. B., Bleijs, D. A., van Vliet, S. J., van Duijnhoven, G. C. F., Grabovsky, V., Alon, R., Figdor, C. G., and van Kooyk, Y. DC-SIGNICAM-2 interaction mediates dendritic cell trafficking. Nature Immunology 1(4), 353-357. 2000.
16. van Remoortere, A., Hokke, C. H., van Dam, G. J., van Die, I., Deelder, A. M., and van den Eijnden, D. H. (2000) Glycobiology 10, 601-609
17. Nyame, A. K., Leppanen, A. M., Debose-Boyd, R., and Cummings, R. D. (1999) Glycobiology 9, 1029-1035
18. Nyame, K. A., Leppanen, A., Bogitsh, B. J., and Cummings, R. D. (2000) Exp Parasitol 96, 202-212
19. Geijtenbeek, T. B. H., van Kooyk, Y., van Vliet, S. J., Renes, M. H., Raymakers, R. A. P., and Figdor, C. G. (1999) Blood 94, 754-764
20. Appelmelk, B. J., M. A. Monteiro, S. L. Martin, A. P. Moran, and C. M. Vandenbroucke-Grauls. 2000. Why *Helicobacter pylori* has Lewis antigens. Trends Microbiol 8:565-70.
21. Srivatsan, J., Smith, D. F., and Cummings, R. D. (1992) J Biol Chem 267, 20196-20203
22. Alvarez, C. P., F. Lasala, J. Carrillo, O. Muniz, A. L. Corbi, and R. Delgado. 2002. C-Type Lectins DC-SIGN and L-SIGN Mediate Cellular Entry by Ebola Virus in cis and in trans. J Virol 76:6841-4.
23. Geijtenbeek, T. B. H., van Duijnhoven, G. C. F., van Vliet, S. J., Krieger, E., Vriend, G., Figdor, C. G., and van Kooyk, Y. (2002) J Biol Chem 277, 11314-11320
24. Kudryashov, V., P. W. Glunz, L. J. Williams, S. Hintermann, S. J. Danishefsky, and K. O. Lloyd. 2001. Toward optimized carbohydrate-based anticancer vaccines: epitope clustering, carrier structure, and adjuvant all influence antibody responses to Lewis(y) conjugates in mice. Proc Natl Acad Sci USA 98:3264-9.
25. Keizer, G. D., J. Borst, C. G. Figdor, H. Spits, F. Miedema, C. Terhorst, and J. E. De Vries. 1985. Biochemical and functional characteristics of the human leukocyte membrane antigen family LFA-1, Mo-1 and p150,95. *Eur J Immunol* 15:1142-8.
26. Caligaris-Cappio, F., G. Pizzolo, M. Chilosi, L. Bergui, G. Semenzato, L. Tesio, L. Morittu, F. Malavasi, M. Gobbi, R. Schwarting, et. al. 1985. Phorbol ester induces abnormal chronic lymphocytic leukemia cells to express features of hairy cell leukemia. *Blood* 66:1035-42.
27. Negrini, R., L. Lisato, I. Zanella, L. Cavazzini, S. Gullini, V. Villanacci, C. Poiesi, A. Albertini, and S. Ghielmi. 1991.

Helicobacter pylori infection induces antibodies cross-reacting with human gastric mucosa. *Gastroenterology* 101: 437-45.
28. Sallusto, F. and A. Lanzavecchia. 1994. Efficient presentation of soluble antigen by cultured human dendritic cells is maintained by granulocyte/macrophage colony-stimulating factor plus interleukin 4 and downregulated by tumor necrosis factor alpha. *J Exp Med* 179:1109-18.
29. Hed, J., G. Hallden, S. G. Johansson, and P. Larsson. 1987. The use of fluorescence quenching in flow cytofluorometry to measure the attachment and ingestion phases in phagocytosis in peripheral blood without prior cell separation. *J Immunol Methods* 101:119-25.
30. Colmenares, M., A. Puig-Kroger, O. M. Pello, A. L. Corbi, and L. Rivas. 2002. Dendritic Cell (DC)-specific Intercellular Adhesion Molecule 3 (ICAM-3)-grabbing Nonintegrin (DC-SIGN, CD209), a C-type Surface Lectin in Human DCs, Is a Receptor for *Leishmania* Amastigotes. *J Biol Chem* 277:36766-9.
31. Chatterjee, D. and K. H. Khoo. 1998. Mycobacterial lipoarabinomannan: an extraordinary lipoheteroglycan with profound physiological effects. *Glycobiology* 8:113-20.
32. Redpath, S., P. Ghazal, and N. R. Gascoigne. 2001. Hijacking and exploitation of IL-10 by intracellular pathogens. *Trends Microbiol* 9:86-92.
33. Demangel, C., A. G. Bean, E. Martin, C. G. Feng, A. T. Kamath, and W. J. Britton. 1999. Protection against aerosol *Mycobacterium tuberculosis* infection using *Mycobacterium bovis Bacillus* Calmette Guerin-infected dendritic cells. *Eur J Immunol* 29:1972-9.
34. Henderson, R. A., S. C. Watkins, and J. L. Flynn. 1997. Activation of human dendritic cells following infection with Mycobacterium tuberculosis. *J Immunol* 159:635-43.
35. Inaba, K., M. Inaba, M. Naito, and R. M. Steinman. 1993. Dendritic cell progenitors phagocytose particulates, including bacillus Calmette-Guerin organisms, and sensitize mice to mycobacterial antigens in vivo. *J Exp Med* 178:479-88.
36. Tsuji, S., M. Matsumoto, O. Takeuchi, S. Akira, I. Azuma, A. Hayashi, K. Toyoshina, and T. Seya. 2000. Maturation of human dendritic cells by cell wall skeleton of *Mycobacterium bovis bacillus* Calmette-Guerin: involvement of toll-like receptors. *Infect Immun* 68:6883-90.
37. Geijtenbeek, T. B., G. C. van Duijnhoven, S. J. van Vliet, E. Krieger, G. Vriend, C. G. Figdor, and Y. van Kooyk. 2002. Identification of different binding sites in the dendritic cell-specific receptor DC-SIGN for intercellular adhesion molecule 3 and HIV-1. *J Biol Chem* 277:11314-20.
38. Bashirova, A. A., T. B. H. Geijtenbeek, G. C. F. van Duijnhoven, S. J. van Vliet, J. B. Eilering, M. P. Martin, L. Wu, T. D. Martin, N. Viebig, P. A. Knolle, V. N. KewalRamani, Y. van Kooyk, and M. Carrington. 2001. A dendritic cell-specific intercellular adhesion molecule 3-grabbing nonintegrin (dc-sign)-related protein is highly expressed on human liver sinusoidal endothelial cells and promotes hiv-1 infection. *J Exp Med* 193:671-8.
39. Geijtenbeek 2000 as provided elsewhere in this list.
40. Alvarez, C. P., F. Lasala, J. Carrillo, O. Muniz, A. L. Corbi, and R. Delgado. 2002. C-type lectins DC-SIGN and L-SIGN mediate cellular entry by Ebola virus in cis and in trans. *J Virol* 76:6841-4.

The invention claimed is:

1. A method for stimulating an immune response to a tumor antigen, the method comprising
   providing an isolated tumor antigen which is free of Lewis x antigen;
   conjugating, in vitro, the isolated tumor antigen which is free of Lewis x antigen to at least one non-sialylated Lewis x antigen to form a conjugate; and
   administering to an individual in need thereof a composition comprising the conjugate.

2. The method according to claim 1, wherein the tumor antigen is a peptide or glycolipid capable of being presented in the context of MHC class I or class II or C1b.

3. The method according to claim 1, wherein the non-sialylated Lewis x antigen targets the tumor antigen to a C-type lectin receptor on an antigen presenting cell of said individual.

4. The method according to claim 3, wherein said C-type lectin receptor is DC-SIGN.

* * * * *

```
SEQUENCE LISTING

<160> NUMBER OF SEQ ID NOS: 6

<210> SEQ ID NO 1
<211> LENGTH: 17
<212> TYPE: DNA
<213> ORGANISM: Artificial Sequence
<220> FEATURE:
<223> OTHER INFORMATION: Synthetic construct

<400> SEQUENCE: 1
agactgcgta ccaattc                                                      17

<210> SEQ ID NO 2
<211> LENGTH: 16
<212> TYPE: DNA
<213> ORGANISM: Artificial Sequence
<220> FEATURE:
<223> OTHER INFORMATION: Synthetic construct

<400> SEQUENCE: 2
gacgatgagt cctgag                                                       16

<210> SEQ ID NO 3
<211> LENGTH: 44
<212> TYPE: PRT
<213> ORGANISM: Artificial Sequence
<220> FEATURE:
<223> OTHER INFORMATION: Synthetic construct

<400> SEQUENCE: 3

Trp Met Gly Leu Ser Asp Leu Asn Gln Glu Gly Thr Trp Gln Trp Val
```

```
                1               5              10              15
Asp Gly Ser Pro Leu Leu Pro Ser Phe Lys Gln Tyr Trp Asn Arg Gly
                20                      25                      30

Glu Pro Asn Asn Val Gly Glu Glu Asp Cys Ala Glu
            35                      40

<210> SEQ ID NO 4
<211> LENGTH: 44
<212> TYPE: PRT
<213> ORGANISM: Artificial Sequence
<220> FEATURE:
<223> OTHER INFORMATION: Synthetic construct

<400> SEQUENCE: 4

Trp Met Gly Leu Ser Asp Leu Asn Gln Glu Gly Thr Trp Gln Trp Val
1               5                       10                      15

Asp Gly Ser Pro Leu Ser Pro Ser Phe Gln Arg Tyr Trp Asn Ser Gly
                20                      25                      30

Glu Pro Asn Asn Ser Gly Asn Glu Asp Cys Ala Glu
            35                      40

<210> SEQ ID NO 5
<211> LENGTH: 78
<212> TYPE: DNA
<213> ORGANISM: Artificial Sequence
<220> FEATURE:
<223> OTHER INFORMATION: Synthetic construct

<400> SEQUENCE: 5
atgttccaac ccctattaga cgccttcata gaaagcgctt ccattgaaaa aatggcctct      60
aaatctcccc cccccctaa                                                  78

<210> SEQ ID NO 6
<211> LENGTH: 84
<212> TYPE: DNA
<213> ORGANISM: Artificial Sequence
<220> FEATURE:
<223> OTHER INFORMATION: Synthetic construct

<400> SEQUENCE: 6
atgttccaac ccctattaga cgccttcata gaaagcgctt ccattgaaaa aatggcctct      60
aaatctcccc cccccctaaa aatc                                            84
```